(12) United States Patent
DiAngelo et al.

(10) Patent No.: US 8,308,481 B2
(45) Date of Patent: Nov. 13, 2012

(54) DENTAL FRAMEWORK

(75) Inventors: Denis John DiAngelo, Germantown, TN (US); Carl Walter Schulter, Germantown, TN (US); Andrew John Schulter, Germantown, TN (US)

(73) Assignee: Cagenix, Inc., Memphis, TN (US)

( * ) Notice: Subject to any disclaimer, the term of this patent is extended or adjusted under 35 U.S.C. 154(b) by 537 days.

(21) Appl. No.: 12/550,137

(22) Filed: Aug. 28, 2009

(65) Prior Publication Data

US 2009/0325125 A1    Dec. 31, 2009

Related U.S. Application Data

(63) Continuation-in-part of application No. 11/875,826, filed on Oct. 19, 2007, now Pat. No. 8,100,692.

(51) Int. Cl.
*A61C 11/00* (2006.01)

(52) U.S. Cl. ........................................ 433/213; 433/214
(58) Field of Classification Search .................. 433/172, 433/173, 174, 175, 176, 213, 214
See application file for complete search history.

(56) References Cited

U.S. PATENT DOCUMENTS

| | | | | |
|---|---|---|---|---|
| 5,857,853 | A * | 1/1999 | van Nifterick et al. | 433/213 |
| 6,142,782 | A * | 11/2000 | Lazarof | 433/174 |
| 6,558,162 | B1 * | 5/2003 | Porter et al. | 433/173 |
| 2006/0115795 | A1 * | 6/2006 | Marshall et al. | 433/218 |

* cited by examiner

*Primary Examiner* — Cris L Rodriguez
*Assistant Examiner* — Eric Rosen
(74) *Attorney, Agent, or Firm* — John Steckler Schwab

(57) ABSTRACT

A method of preparing a dental framework or mathematical model thereof includes creating a replica of a patient's mouth or a framework to be inserted into the patient's mouth, electronically scanning the replica or framework, electronically determining a surface model of a dental framework and manufacturing the framework.

35 Claims, 28 Drawing Sheets

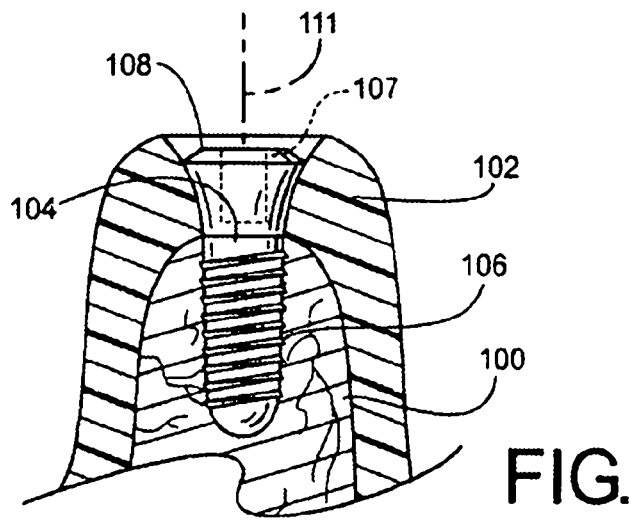
FIG. 1
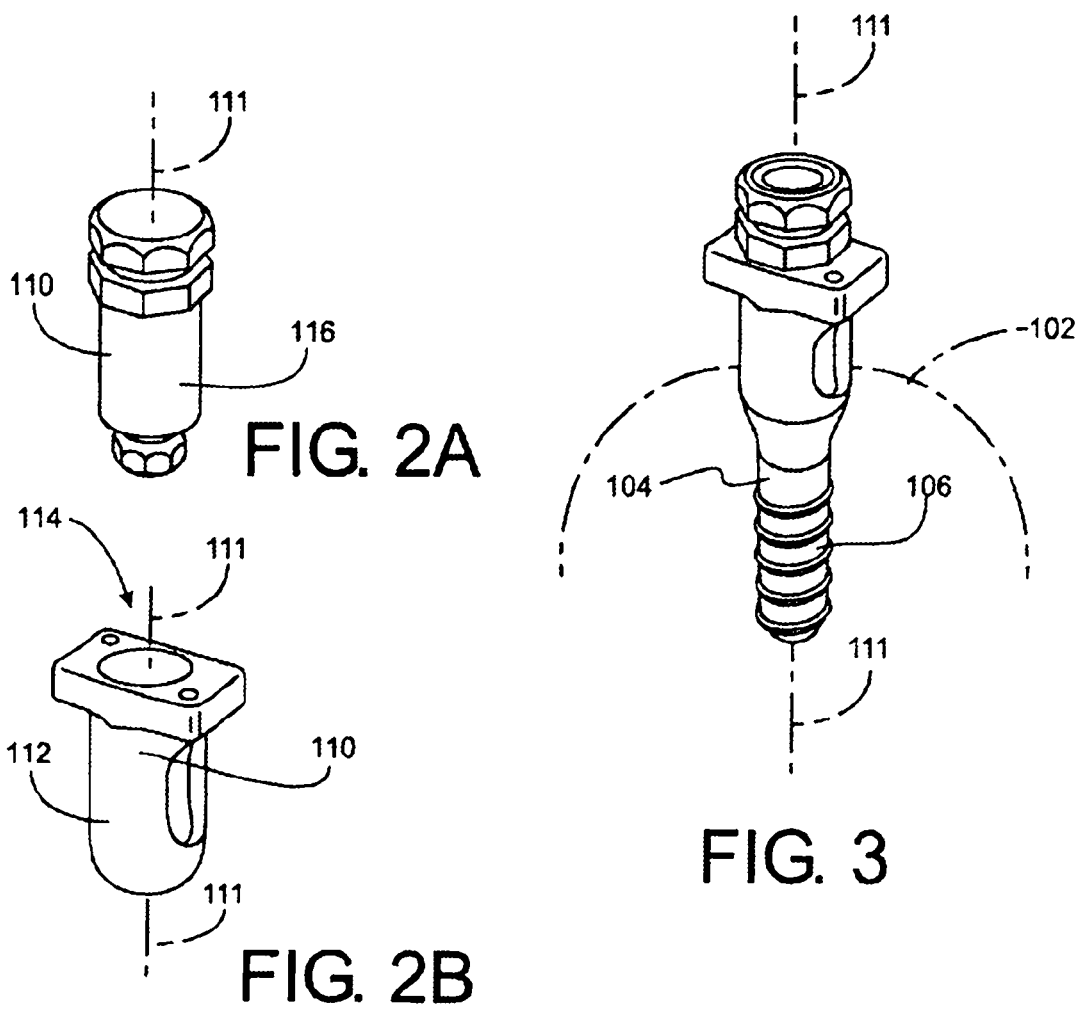
FIG. 2A
FIG. 2B
FIG. 3

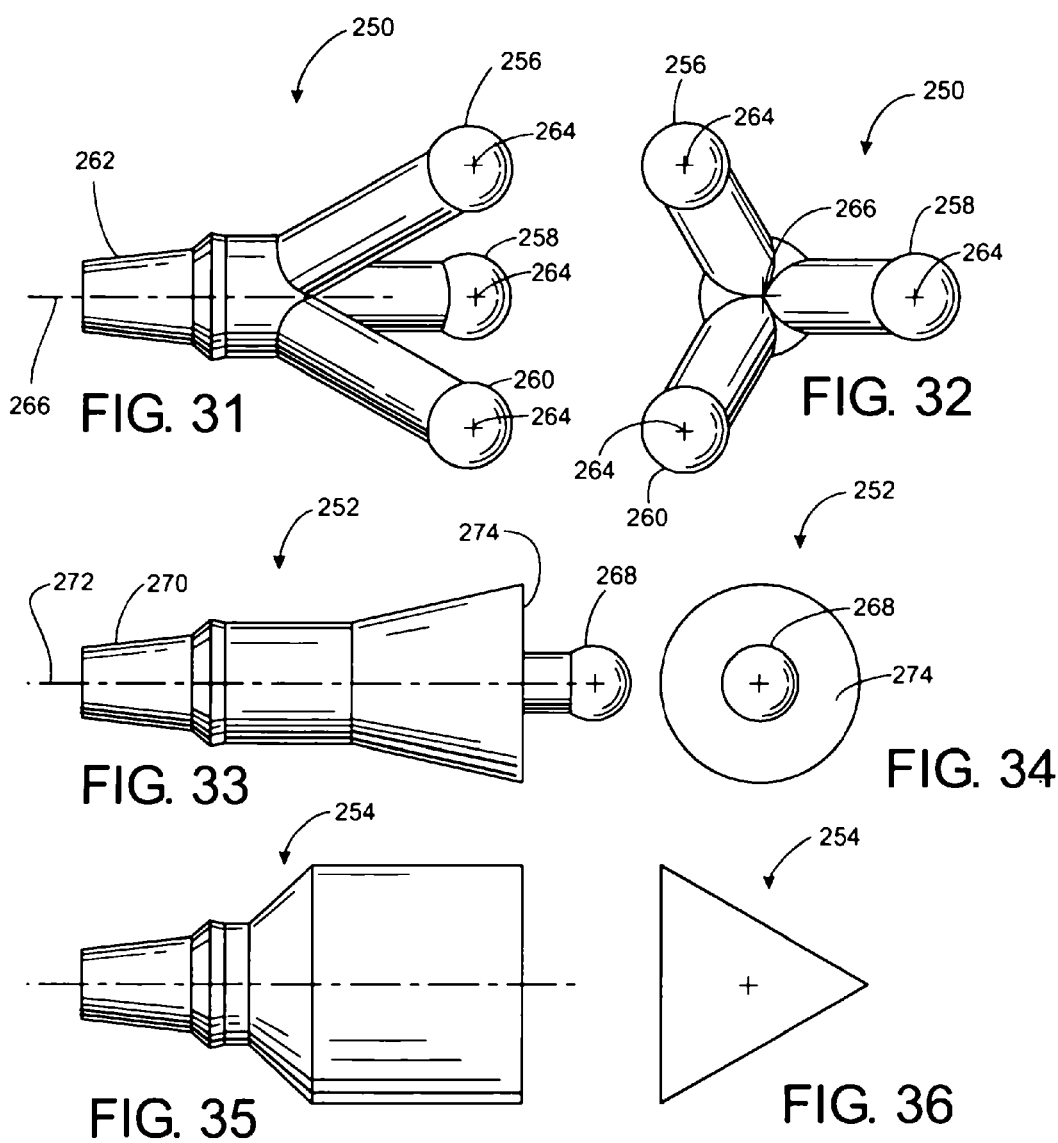

DENTAL FRAMEWORK

This invention is a continuation-in-part of applicant's U.S. patent application, Ser. No. 11/875,826 filed on Oct. 19, 2007 now U.S. Pat. No. 8,100,692 for A Dental Framework, herein incorporated by reference.

FIELD OF THE INVENTION

The invention relates generally to the creation of dental frameworks, and typically dental frameworks for dentures. More particularly it relates to computer implemented methods of manufacturing dental frameworks.

BACKGROUND OF THE INVENTION

Many different processes have been devised to make a dental framework. In the most common of these a dentist makes an impression of a patient's mouth in which copings are embedded that are attached to anchors in the patient's mouth to which the dental framework of the denture will be later attached.

The dentist then attaches analogs to the copings and casts a stone cast replica of the patient's mouth.

The dentist then forms a replica or model dental framework on top of the stone cast in the exact size and shape he wishes the actual dental framework. The dentist then lost wax casts the actual dental framework from the model dental framework.

Unfortunately these models are warped and distorted by the casting process and must be cut apart and soldered together until they fit properly.

What is needed is a method of manufacturing a dental framework that is more precise than these cast frameworks. It is an object of at least one aspect of this invention to provide such a dental framework. It is also an object of at least one aspect of this invention to provide a method for registering dental surfaces that have been digitally scanned in order to define a volume or space in which a computer-generated framework can be disposed. It is an object of at least one aspect of this invention to digitally create a dental framework that possesses a general shape exactly like that of the wax-up framework created by the dentist, while obtaining accurate mating geometries derived from the stone cast. It is also an object of at least one aspect of this invention to provide a method of manufacture that results in a digitally designed denture framework that follows the contour of gum tissue.

These and other objects of the invention will become clear upon examination of the various embodiments and methods described below.

SUMMARY OF THE INVENTION

In accordance with a first aspect of the invention, a method of preparing a dental framework for a dental prosthesis for a patient is provided, the patient having a plurality of anchors embedded in the patient's mandible or maxilla, comprising the steps of coupling a plurality of fittings to a plurality of analogs in a positive replica of a patient's mandible or maxilla; fixing the fittings together with a bridging structure to form a model dental framework; fixing a surface extension to each of the fittings; sequentially scanning a plurality of points on the surface of the model dental framework and the surface extensions to create a point cloud dataset; for each of the fittings represented in the point cloud dataset, deriving from the points scanned from the surface extension coupled to that fitting a desired location and orientation of a corresponding mount to engage the analog on which that fitting was mounted; generating a surface model of an actual dental framework from the derived desired locations and orientations of the mounts; and manufacturing the actual dental framework from the surface model.

The mounts may be configured to be fixed directly to anchors in a patient's mouth. The mounts may be configured to be fixed to intermediate structures that are in turn fixed to the anchors. Each of the surface extensions may have a longitudinal axis that is coaxial with a corresponding longitudinal axis of the fitting on which it is fixed.

In accordance with a second aspect of the invention, a method of preparing an actual dental framework for a dental prosthesis for a patient from a model framework is provided, wherein the model framework comprises a plurality of fittings configured to engage a plurality of corresponding anchors in the patient's mouth, and a bridging structure coupling the fittings together, the method comprising the steps of fixing surface extensions to each of the plurality of fittings; sequentially scanning a plurality of points on the surface of the model dental framework and the surface extensions to generate a point cloud dataset; for each of the fittings, deriving from the points scanned from the surface extension coupled to that fitting a desired location and orientation of a corresponding mount to engage the analog on which that fitting was mounted; and generating a surface model of an actual dental framework from the derived desired locations and orientations of the corresponding mounts.

The mounts may be configured to be fixed directly to anchors in a patient's mouth. The mounts may be configured to be fixed to intermediate structures that are in turn fixed to the anchors. Each of the surface extensions has a longitudinal axis that is coaxial with a corresponding longitudinal axis of the fitting on which it is fixed.

In accordance with a third aspect of the invention, a method of preparing a dental prosthesis for a patient is provided, comprising the steps of coupling a plurality of copings to a plurality of anchors or surmounted abutments embedded in a patient's mandible or maxilla; impressing a negative replica of the patient's mandible or maxilla; removing the negative replica and embedded copings; fixing surface extensions to each of the copings; scanning a plurality of points on the surface extensions; deriving from the plurality of points a desired location and orientation of mounts to engage the anchors or surmounted abutments on which the copings were mounted; generating a surface model of the dental prosthesis from the derived desired locations and orientations of the mounts; and manufacturing the dental prosthesis from the surface model.

The step of generating a surface model may include the step of generating a surface model of at least a portion of the mounts. The surface model of the at least a portion of the mounts may include a surface model of surfaces configured to engage the plurality of anchors or surmounted abutments. The step of generating a surface model may include the step of generating a surface model of a bridging structure that extends between and couples the mounts. The dental prosthesis may comprise a dental framework and further wherein the dental framework may comprise the mounts.

In accordance with a fourth aspect of the invention, a method of preparing a dental prosthesis for a patient from a negative replica of the patient's maxilla or mandible is provided, the negative replica including a plurality of copings configured to engage a corresponding plurality of anchors or surmounted abutments in the patient's maxilla or mandible, the method comprising the steps of fixing surface extensions to each of the copings; scanning a plurality of points on the surface extensions; deriving from the plurality of points a desired location and orientation of mounts configured to engage the anchors or surmounted abutments; and generating a surface model of the dental prosthesis from the derived desired locations and orientations of the mounts.

The step of generating a surface model may include the step of generating a surface model of at least a portion of the mounts. The surface model of the at least a portion of the mounts may include a surface model of surfaces configured to engage the plurality of anchors or surmounted abutments. The step of generating a surface model may include the step of generating a surface model of a bridging structure that extends between and couples the mounts. The dental prosthesis may comprise a dental framework and the dental framework may comprise the mounts. The dental prosthesis may be a denture.

In accordance with a fifth aspect of the invention, a method of preparing a dental prosthesis for a patient from a negative replica of the patient's maxilla or mandible is provided, the negative replica including a plurality of copings configured to engage a corresponding plurality of anchors or surmounted abutments in the patient's maxilla or mandible, the method comprising the steps of scanning a surface of the negative replica to provide a first point cloud dataset representing a surface of the negative replica; and generating a surface model of the dental prosthesis from the first point cloud dataset.

The surface of the negative replica may include surfaces of copings. The method may further include the steps of fixing surface extensions to the negative replica and scanning the surface extensions to provide a second point cloud dataset. The dental prosthesis may comprise a dental framework and the dental framework may comprise the mounts. The dental prosthesis may comprise a denture.

In accordance to a sixth aspect of the invention, a method of computer generating a digital model of a dental prosthesis for a patient is provided, the method comprising the steps of coupling a plurality of surface extensions to analogs or surmounted abutments embedded in a positive replica of the patient's mouth, the positive replica of the patient's mouth including a positive replica of the patient's mucosal tissues; sequentially scanning surfaces of the surface extensions and deriving therefrom a location of the analogs or surmounted abutments; sequentially scanning the replica of the patient's mucosal tissues to create a point cloud dataset indicating a surface of the patient's mucosal tissues with respect to the anchors or surmounted abutments; and computer-generating a digital model of a dental prosthesis, the digital model comprising model mounts configured to engage analogs or surmounted abutments in the patient's mandible or maxilla, the digital model also comprising model bridging structures extending between and coupling the model mounts, wherein the model bridging structures are computer-generated such that they do not intersect the surface of the patient's mucosal tissue as indicated by the point cloud dataset.

The bridging structure may comprise a dental framework. The bridging structure may comprise a component of a denture. The model bridging structure may comprise computer-generated to be spaced a predetermined distance away from the surface of the patient's mucosal tissue as indicated by the point cloud dataset.

In accordance with a seventh aspect of the invention, a method of creating a digital model of a dental prosthesis of a patient is provided, the method comprising making an impression of the patient's mouth; making a stone cast of the impression; forming a diagnostic wax-up on the stone cast; digitally scanning at least a first surface of the diagnostic wax-up to form a first point cloud dataset; digitally scanning at least a second surface of the impression to form a second point cloud dataset; and digitally registering the first and second point cloud datasets.

The step of digitally registering may comprise the steps of registering a portion of the first point cloud dataset with a portion of the second point cloud dataset; wherein the surface of the diagnostic wax-up, from which the portion of the first point cloud dataset was scanned, was formed by a portion of a common surface of the stone cast; and further wherein the portion of the second point cloud dataset was formed by a portion of a surface of the impression that formed the common surface of the stone cast. The step of digitally scanning at least a first surface of the diagnostic wax-up may comprise the step of digitally scanning both a first surface of the diagnostic wax-up and a first portion of the surface of the stone cast while said diagnostic wax-up is mounted on the stone cast to create the first point cloud dataset, which comprises at least a common point cloud dataset including points defined by the diagnostic wax-up and points defined by the surface of the stone cast. The step of digitally registering the first and second point cloud datasets may comprise the step of digitally registering the points defined by the surface of the stone cast in the common point cloud dataset, and points defined by the impression in the second point cloud dataset. A first impression surface may be formed the points defined by the impression in the second point cloud dataset, and the first impression surface may form the stone cast surface from which the points defined by the surface of the stone cast in the common point cloud dataset were scanned.

In accordance with an eighth aspect of the invention, a method of creating a digital model of a dental prosthesis of a patient from an impression taken of the patient's mouth, a stone cast made from the impression, and a diagnostic wax-up made on the stone cast is provided, the method comprising the steps of digitally scanning at least a first surface of the diagnostic wax-up to form a first point cloud dataset; digitally scanning at least a second surface of the impression to form a second point cloud dataset; and digitally registering the first and second point cloud datasets.

The step of digitally registering may comprise the steps of registering a portion of the first point cloud dataset with a portion of the second point cloud dataset; wherein the surface of the diagnostic wax-up from which the portion of the first point cloud dataset was scanned was formed by a portion of a surface of the stone cast that was formed by a common surface of the stone cast; and further wherein the portion of the second point cloud dataset was formed by a portion of a surface of the impression that formed the common surface of the stone cast. The step of digitally scanning at least a first surface of the diagnostic wax-up may comprise the step of digitally scanning both a first surface of the diagnostic wax-up and a first portion of the surface of the stone cast while said diagnostic wax-up is mounted on the stone cast to create the first point cloud dataset, which comprises at least a common point cloud dataset including points defined by the diagnostic wax-up and points defined by the surface of the stone cast. The step of digitally registering the first and second point cloud datasets may comprise the step of digitally registering the points defined by the surface of the stone cast in the common point cloud dataset, and points defined by the impression in the second point cloud dataset. A first impression surface may form the points defined by the impression in the second point cloud dataset, and further wherein said first impression surface may form the stone cast surface from which the points defined by the surface of the stone cast in the common point cloud dataset were scanned.

In accordance with a ninth aspect of the invention, a method of creating a digital model of a dental prosthesis of a patient is provided, comprising the steps of making an impression of the patient's mouth; making a stone cast of the impression; making a diagnostic wax-up on the stone cast; digitally scanning at least a first surface of the diagnostic wax-up to form a first point cloud dataset; digitally scanning at least a second surface of the stone cast to form a second point cloud dataset; and digitally registering the first and second point cloud datasets.

The step of digitally registering may comprise the steps of digitally registering a portion of the first point cloud dataset with a portion of the second point cloud dataset; wherein the portion of the first point cloud dataset was scanned from a portion of the diagnostic wax-up formed by a forming surface of the stone cast; and wherein the portion of the second point cloud dataset was scanned from the forming surface of the stone cast. The step of digitally scanning at least a first surface of the diagnostic wax-up may comprise the steps of digitally scanning both the first surface of the diagnostic wax-up and a first portion of the surface of the stone cast while said diagnostic wax-up is mounted on the stone cast; and creating a common point cloud dataset including points scanned from the first surface of diagnostic wax-up and points scanned from the first portion of the surface of the stone cast. The step of digitally registering the first and second point cloud datasets may comprise the step of digitally registering the points scanned from the first portion of the surface of the stone cast in the common point cloud dataset, and points scanned from the stone cast in the second point cloud dataset. A common portion of the stone cast surface may define both the points scanned from the surface of the stone cast in the common point cloud dataset and the points scanned from the stone cast in the second point cloud dataset. The step of digitally registering the first and second point cloud datasets may comprise the step of registering points in both the first and second point cloud datasets taken from the common portion of the stone cast surface.

In accordance with a tenth aspect of the invention, a method of creating a digital model of a dental prosthesis of a patient from an impression of the patient's mouth, a stone cast of the impression, and a diagnostic wax-up formed on the stone cast is provided, the method comprising the steps of digitally scanning at least a first surface of the diagnostic wax-up to form a first point cloud dataset; digitally scanning at least a second surface of the stone cast to form a second point cloud dataset; and digitally registering the first and second point cloud datasets.

The step of digitally registering may comprise the steps of digitally registering a portion of the first point cloud dataset with a portion of the second point cloud dataset; wherein the portion of the first point cloud dataset was scanned from a portion of the diagnostic wax-up formed by a forming surface of the stone cast; and wherein the portion of the second point cloud dataset was scanned from the forming surface of the stone cast. The step of digitally scanning at least a first surface of the diagnostic wax-up may comprise the steps of digitally scanning both the first surface of the diagnostic wax-up and a first portion of the surface of the stone cast while said diagnostic wax-up is mounted on the stone cast; and creating a common point cloud dataset including points scanned from the diagnostic wax-up and points scanned from the first portion of the surface of the stone cast. The step of digitally registering the first and second point cloud datasets may comprise the step of digitally registering the points scanned from the first portion of the surface of the stone cast in the common point cloud dataset, and points scanned from the stone cast in the second point cloud dataset. A common portion of the stone cast surface may define both the points scanned from the surface of the stone cast in the common point cloud dataset and the points scanned from the stone cast in the second point cloud dataset. The step of digitally registering the first and second point cloud datasets may comprise the step of registering points in both the first and second point cloud datasets taken from the common portion of the stone cast surface.

In accordance with an eleventh aspect of the invention, a method of creating a digital model of a dental prosthesis of a patient from an impression of the patient's mouth, a stone cast of the impression, a diagnostic wax-up formed on the stone cast, and a putty index formed on the diagnostic wax-up and the stone cast is provided, the method comprising the steps of digitally scanning at least a first surface of the putty index to form a first point cloud dataset; digitally scanning at least a second surface of the stone cast to form a second point cloud dataset; and digitally registering the first and second point cloud datasets.

The step of digitally registering may comprise the steps of digitally registering a portion of the first point cloud dataset with a portion of the second point cloud dataset; wherein the portion of the first point cloud dataset was scanned from a portion of the putty index formed by a forming surface of the stone cast; and wherein the portion of the second point cloud dataset was scanned from the forming surface of the stone cast. The step of digitally scanning at least a first surface of the putty index may comprise the steps of digitally scanning both the first surface of the putty index and a first portion of the surface of the stone cast while said putty index is mounted on the stone cast; and creating a common point cloud dataset including points scanned from the putty index and points scanned from the first portion of the surface of the stone cast. The step of digitally registering the first and second point cloud datasets may comprise the step of digitally registering the points scanned from the first portion of the surface of the stone cast in the common point cloud dataset, and points scanned from the stone cast in the second point cloud dataset. A common portion of the stone cast surface may define both the points scanned from the surface of the stone cast in the common point cloud dataset and the points scanned from the stone cast in the second point cloud dataset. The step of digitally registering the first and second point cloud datasets may comprise the step of registering points in both the first and second point cloud datasets taken from the common portion of the stone cast surface. The impression may comprise a plurality of copings. The method may further comprise the step of fixing a plurality of surface extensions to the plurality of copings. The step of digitally scanning at least the second surface may comprise the step of digitally scanning surfaces of the plurality of surface extensions. The stone cast may comprise a plurality of analogs. The method may further comprise the step of fixing a plurality of surface extensions to the plurality of analogs. The step of digitally scanning at least the second surface may comprise the step of digitally scanning surfaces of the plurality of surface extensions.

In accordance with a twelfth aspect of the invention, a method of preparing a denture for a patient is provided, the method comprising the steps of coupling a plurality of fittings to a plurality of analogs embedded in a stone cast of the patient's maxilla or mandible; forming a diagnostic wax-up on the stone cast in which the plurality of fittings are embedded; removing the diagnostic wax-up with embedded fittings from the stone cast; fixing surface extensions to each of the plurality of fittings; sequentially scanning a plurality of points on the surface of the diagnostic wax-up and on the surface extensions to generate a point cloud dataset; and, for each of the fittings represented in the point cloud dataset, deriving from the points scanned from the surface extension of that fitting a desired location and orientation of a corresponding mount configured to engage the analog on which that fitting was mounted.

In accordance with a thirteenth aspect of the invention, a method of creating a dental framework having a plurality of mating surfaces that are configured to engage corresponding plurality of anchors in a patient's mouth, is provided the method comprising the steps of: attaching a plurality of copings to the anchors; forming an impression in which the copings are embedded; attaching an analog to each of the plurality of copings; forming a stone cast in which the plurality of copings are embedded; attaching alignment posts having surface extensions to each of the analogs; digitally scanning the surface extensions to generate a point cloud dataset; deriving the relative positions and orientations of the mating surfaces from the point cloud dataset; generating a toolpath that is configured to generate the mating surfaces in their relative positions and orientations; and making the framework in accordance with the toolpath.

The alignment posts may be attached to surfaces of the analogs that correspond to the plurality of mating surfaces on the anchors. The framework may further comprise a bridging structure that extends between and couples the plurality of mating surfaces together, and the step of generating a toolpath may further comprise the step of generating a toolpath configured to generate the bridging structure. The step of digitally scanning the surface extensions may further comprise the step of scanning the surface extensions with a laser scanner at a plurality of locations on each surface extension to produce a plurality of three dimensional datapoints, said point cloud dataset comprising the three dimensional datapoints. The step of deriving the relative positions and orientations may further comprise the step of electronically fitting datapoints scanned from the surface extensions to a predetermined three dimensional geometry of the surface extensions stored in a computer memory.

In accordance with a fourteenth aspect of the invention, a method of generating a toolpath for manufacturing a dental framework for a patient's mouth is provided, the patient's mouth comprising a plurality of anchors embedded in the patient's mandible or maxilla, the framework being made from a stone cast with embedded analogs, the stone cast being made from an impression having embedded copings, the impression being taken directly from the patient's mouth, wherein the framework further comprises a plurality of mating surfaces that are configured to engage the plurality of anchors, the method comprising the steps of: attaching alignment posts having surface extensions to each of the analogs embedded in the stone cast of the patient's mouth; digitally scanning the surface extensions to generate a point cloud dataset; deriving the relative positions and orientations of the mating surfaces from the point cloud dataset; and generating a toolpath that is configured to generate the mating surfaces in their relative positions and orientations.

In accordance with a fifteenth aspect of the invention a method of creating a dental framework having a plurality of mating surfaces that are configured to engage a corresponding plurality of anchors in the patient's mouth is provided, the method comprising the steps of: attaching a plurality of copings to the anchors; forming a stone cast in which the copings are embedded; attaching an analog to each of the plurality of copings; forming a stone cast in which the plurality of analogs are embedded; attaching a fitting to each of the plurality of analogs; coupling the fittings together with a bridging structure to hold them in their relative positions thereby forming a model framework; removing the fittings and bridging structure from the copings; attaching alignment posts having surface extensions to each of the fittings; digitally scanning the surface extensions to generate a point cloud dataset; deriving the relative positions and orientations of the mating surfaces from the point cloud dataset; generating a toolpath that is configured to generate the mating surfaces in their relative positions and orientations; and making the framework in accordance with the toolpath.

The alignment posts may be attached to surfaces of the fittings that correspond to the plurality of mating surfaces on the anchors. The step of digitally scanning further may comprise the step of digitally scanning the surface of the bridging structure to generate the point cloud dataset, and the step of generating a toolpath may comprise the step of generating a toolpath configured to generate the bridging structure from datapoints scanned from the surface of the bridging structure. The step of digitally scanning the surface extensions may comprise the step of scanning the surface extensions with a laser scanner at a plurality of locations on each surface extension to produce a plurality of three dimensional datapoints, the point cloud dataset comprising the three dimensional datapoints. The step of deriving the relative positions and orientations may comprise the step of electronically fitting datapoints scanned from the surface extensions to a predetermined geometry of the surface extensions stored in a computer memory.

In accordance with a sixteenth aspect of the invention, a method of creating a dental framework having a plurality of mating surfaces that are configured to engage a corresponding plurality of anchors in the patient's mouth, the method comprising the steps of: attaching a plurality of copings to the anchors; forming a stone cast in which the copings are embedded; attaching an analog to each of the plurality of copings; forming a stone cast in which the plurality of analogs are embedded; attaching a fitting to each of the plurality of analogs; coupling the fittings together with a bridging structure to hold them in their relative positions thereby forming a model framework; removing the fittings and bridging structure from the copings; attaching alignment posts having surface extensions to each of the fittings; digitally scanning the surface extensions to generate a point cloud dataset; deriving the relative positions and orientations of the mating surfaces from the point cloud dataset; generating a toolpath that is configured to generate the mating surfaces in their relative positions and orientations; and making the framework in accordance with the toolpath.

In accordance with the seventeenth aspect of the invention, a method of locating a dental appliance with respect to dental surfaces is provided, the method comprising the steps of: scanning a first dental surface to create a first point cloud dataset; scanning a second dental surface to create a second point cloud dataset; registering the first and second point cloud datasets by aligning points in each dataset taken from the overlapping surface portions; and using non-overlapping portions of both point cloud datasets to define the location of the dental appliance.

The first dental surface and the second dental surface may be selected from the group comprising an impression, a stone cast, a diagnostic wax-up, a facial index and a dental framework. The second dental surface is selected from the group comprising an impression, a stone cast, a diagnostic wax-up, a facial index, and a dental framework. The first point cloud dataset may comprise both points scanned from a surface of a diagnostic wax-up disposed on a stone cast and points scanned from a surface of the stone cast while the diagnostic wax-up is disposed on it, and the second point cloud dataset may comprise points scanned from the surface of the stone cast and points scanned from a surface of the stone cast that was covered by the diagnostic wax-up when the diagnostic wax-up was scanned to create the first point cloud dataset, and the portions of the stone cast common scanned to both point cloud datasets may constitute the overlapping portions of both point cloud datasets. A facial index may have a first surface formed in abutment to a diagnostic wax-up and a second surface formed in abutment to a third surface of a stone cast, the first point cloud dataset may comprise points scanned both from the first surface and the second surface, and the second point cloud dataset may comprise points scanned from the third surface and points scanned from a fourth surface of the stone cast adjacent to the third surface, and the overlapping portions of both point cloud datasets may comprise points scanned from the second surface in the first point cloud dataset and points scanned from the third surface in the second point cloud dataset.

In accordance with an eighteenth aspect of the invention a method of creating a dental framework having a plurality of mating surfaces configured to engage a corresponding plurality of anchors in the patient's mouth and having an exterior shape that is nearly exactly the same as a prior constructed wax up framework, the method comprising the steps of; digitally scanning the prior constructed wax-up framework to generate a first digital representation; digitally scanning the stone cast with surface extensions attached to generate a second digital representation; digitally scanning the wax-up framework coupled to the stone cast to generate a third digital representation; aligning the digital representations; deriving to position and orientation of the mating surfaces from the aligned digital representations; generating a surface model of the final framework and manufacturing the framework in accordance with said toolpath.

In accordance with a nineteenth aspect of the invention a method of creating a dental framework in accordance with the above mentioned methods of manufacture having a gum confronting surface that follows the contours of the surfaces inside the patient's mouth confronting the framework. This confronting surface of the framework may follow the exact contours of the soft tissues, or may generally follow the contours and not follow each undulation. The contoured framework may possess a cross section that is elliptical, round, chamfered, or of a free form shape chosen by the operator. The contoured framework may be straight cut. Straight cutting is a shaping of the contoured framework confronting surface to follow the general contours along the length of each bridging structure, the confronting surface having a cross section that is generally perpendicular to the sides of the bridging structure, or having a cross section that is elliptical, round, chamfered or a free form shape of a desired geometry.

BRIEF DESCRIPTION OF THE DRAWINGS

The invention is illustrated by the accompanying drawings, in which:

FIG. 1 is a fragmentary cross sectional view of an anchor embedded in a mandible.

FIGS. 2A and 2B are perspective views of a two piece coping to be attached to the anchor of FIG. 1.

FIG. 3 is a perspective view of anchor with coping attached.

FIGS. 31-36 are side and end views of alternative alignment posts.

DETAILED DESCRIPTION OF THE PREFERRED EMBODIMENTS

Figure 4:
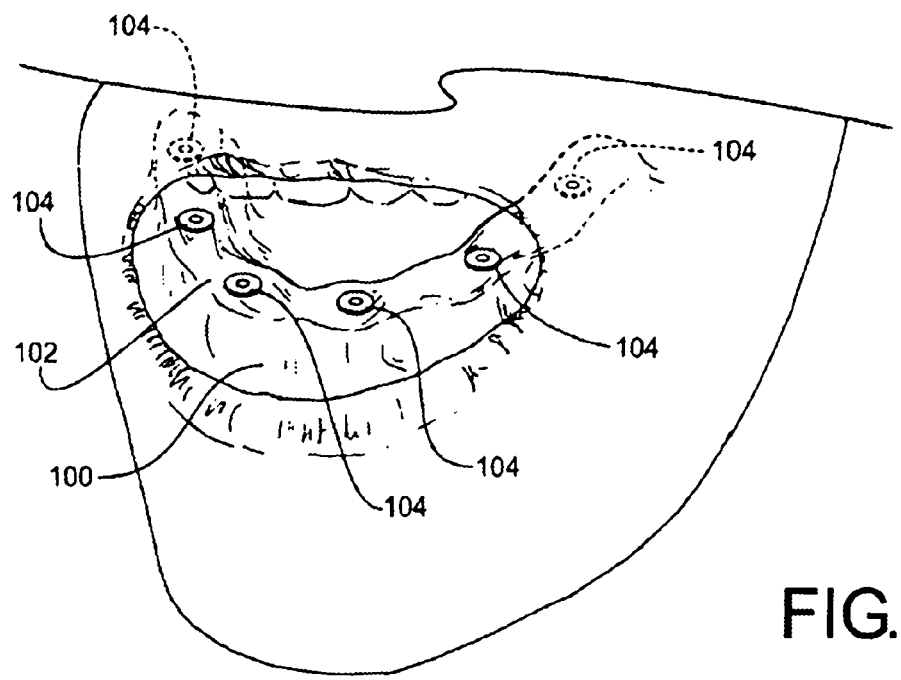
FIG. 4 is a fragmentary perspective view of a patient's open mouth with the anchors embedded in the patient's mandible.

In FIG. 1, the patient's jaw or mandible 100 can be seen overlaid with soft mucosal tissue 102 (known commonly as "gum tissue"). An anchor 104, also known as an "implant" or "fixture" is shown embedded into the patient's mandible 100. This anchor is retained within the mandible by a screw thread 106. It is driven into the mandible 100 by coupling a wrench or similar device to the top of the anchor 104 and rotating the wrench to drive the anchor into the jaw bone just as one would drive a screw into a piece of wood. In an alternative embodiment, the anchor 104 is press fitted into a hole formed with a drill, reamer, broach, osteotome, or similar device.

FIG. 1 illustrates the first step in the process, that of forming an opening in the mandible of the patient and fixing an anchor therein, while leaving a top surface of the anchor exposed above mucosal tissue 102 for mating (coupling) to and supporting a dental prosthesis or restorative component such as a denture, bridge, crown, framework, abutment, healing cap, or coping (hereinafter referred to as "denture"). Note that while the process illustrated herein describes and illustrates a mandible for illustration purposes, the same process is performed to embed anchors 104 into the patient's maxilla and create dental prostheses for the maxilla.

To attach anchors 104, the dentist first makes an incision in the mucosal tissue 102 where a missing tooth or teeth would normally extend from the mandible where it is embedded, through the gum, and into the oral cavity. Once the incision is made, the dentist makes a hole (which may include such processes as drilling, broaching or reaming) in the mandible 100 in the same general direction and location as the missing tooth. The dentist then fixes an anchor 104 into the hole thus created and sutures the incision, typically leaving mating surface 108 of anchor 104 exposed while the bone osseointegrates to the outer surface of anchor 104. Alternatively, the dentist may attach a healing cap to the anchor 104 and suture the gum around or over the top of the anchor 104 and the healing cap, permitting the gum to heal around or over the top of the anchor 104 as it osseointegrates. In this alternative process, once the anchor has osseointegrated, the dentist incises the mucosal tissue 102 extending over the top of the now-integrated anchor 104 and retracts the mucosal tissue to each side, exposing the mating surface 108 of anchor 104 and permitting the mucosal tissue to heal.

The anchor 104 has a central longitudinal aperture 107 in the top which is configured to receive an impression coping 110 (FIG. 2) (or a fastener configured to mount the impression coping 110) that is affixed to the anchor 104. This coping transfers the size, shape, location or orientation of the mating surface 108 of the anchor (and preferably all four) to the stone cast (see below). It is the mating surface 108 that is oriented to the finished denture, and hence the mating surface 108 from which the structures of the denture that mount to the anchors are derived. For convenience of illustration in FIG. 1 only a single anchor 104 is shown. In practice, anywhere from one to twelve of these anchors are embedded in the maxilla and are provided as mounting points for the denture. In an alternative configuration, anchor 104 may have a variety of configurations on its mating surface 108 including threaded or unthreaded protrusions or recesses that are configured to engage a denture. The use of an anchor 104 having a central aperture and internal threads for engaging a coping is a matter of convenience herein and should not suggest that the process is limited to an anchor having this configuration.

FIGS. 2A, 2B and 3 illustrate an impression coping 110 that is configured to be fixed on to the mating surface 108 of anchor 104. In the second step of the process, the dentist fits anchor 104 with a coping 110 that is aligned to surface 108 (FIG. 1). Mating surface 108 is typically the surface on which the denture will be mounted or a surface having a predetermined position with respect to that surface on which the denture will ultimately be mounted. The coping 110 is configured to engage surface 108 and surrounding structures of anchor 104 (if any) such as holes that extend into (or protrusions that extend above) the surface 108.

These interengaging surfaces of coping 110 and anchor 104 serve to align the coping and the anchor in predetermined positions with respect to each other when fixed together, such that if one knows the position and orientation of surfaces on the coping one can know the position and orientation of corresponding structures on the anchor 104 and more preferably when a scanner (see below) determines the position and orientation of structures on copings 110 it can mathematically determine the position and orientation of corresponding structures on anchors 104. Anchor 104 is preferably cylindrical and has a longitudinal axis 111, as does coping 110. In a typical arrangement, when the coping 110 is fixed in its predetermined position with respect to anchor 104, a longitudinal axis 111 of the coping is coaxial with the longitudinal axis of the anchor 104. The coping 110 and the anchor 104 are preferably threadedly engaged to permit surfaces on the coping to be drawn down tightly against mating surface 108 for precise alignment of their interengaging surfaces. Alternatively, the coping 110 and anchor 104 to which it is coupled may be equipped with interengaging snap fastening connecting surfaces that hold the coping in the proper orientation with respect to anchor 104.

FIG. 2A shows a tubular central portion 116 of coping 110 that is configures to be received in an outer sleeve portion 112 of the coping having a central longitudinal hole 114 shown in FIG. 2B.

Sleeve portion 112, as shown in FIG. 3, abuts the soft mucosal tissue surrounding the mating surface 108 of anchor 104, preventing the tissue from covering mating surface 108. Tubular central portion 116 extends through outer sleeve portion 112 and is engaged to the central longitudinal aperture 107 formed in the end of anchor 104 (see FIG. 1). This is the preferred form of the coping 110, and the preferred means for attaching the coping to anchor 104. It is not the only means, however.

FIG. 4 illustrates the mandible 100 of FIGS. 1, 2A, 2B, and 3, with all the anchors 104 implanted in the mandible, and ready for the next step in the process. In this FIGURE, the edentulous mandible 100 has six anchors 104 affixed therein in a spaced-apart relation extending from the front of mandible 100 around each side. The anchors 104 are disposed in a generally upright and parallel relation extending into the top surface of mandible 100. The dentist attaches corresponding copings 110 to the top of each anchor 104 and extends upward in a generally upright and parallel relation to the other copings 110. The application illustrated herein shows the use of six anchors configured to support a denture. Other applications with more or fewer anchors 104 are possible. Furthermore, the mandible need not be edentulous (shown here), but may have, and often does have, a few natural teeth remaining in the maxilla or mandible between which the anchors 104 are embedded to support one or more dentures (such as fixed or removable partial dentures) to fill the gap or gaps between the existing natural teeth. In this case, the anchors would not be spaced evenly about the mandible, as shown here, but would be spaced irregularly in the gaps created by the absence of natural teeth.

Figure 5:
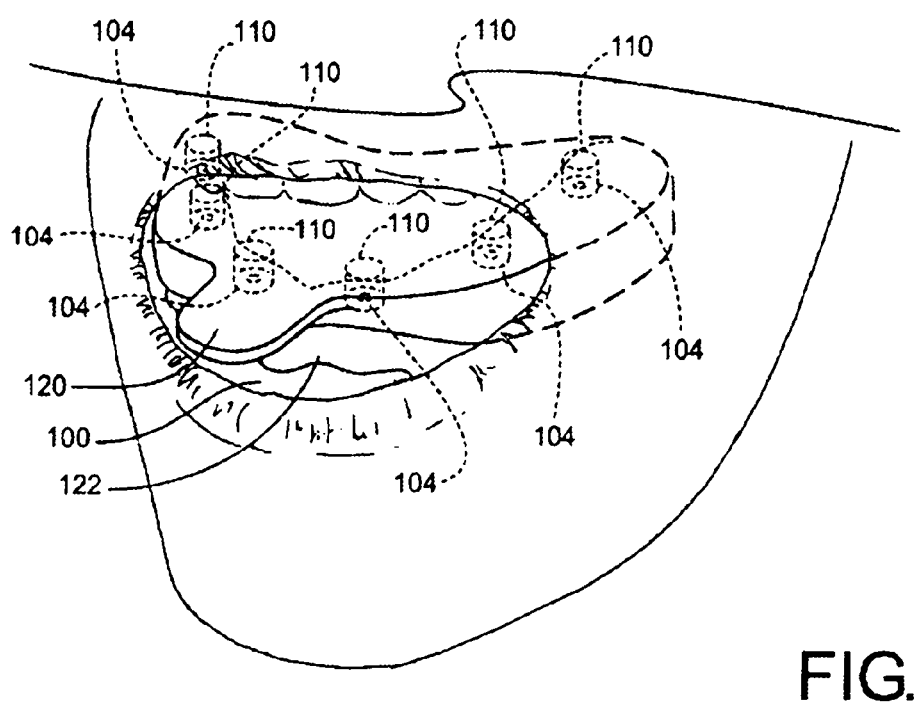
FIG. 5 is a fragmentary perspective view of the patient's open mouth with several copings attached to the anchors and an impression tray with impression material surrounding the patient's mucosal tissue and submerging the copings.

FIG. 5 illustrates the next step in the process of creating a denture, the step of creating an impression of the patient's mandible. This figure shows an impression tray 120 filled with flexible impression material 122. The tray is a semi-flexible plastic structure that holds the impression material 122 in position around the patient's teeth (if any) and mucosal tissue. FIG. 5 shows a tray 120 for the lower teeth surrounding teeth, mucosal tissue, and mandible of the patient.

The copings 110 previously attached by the dentist to the anchors 104 are completely submerged by the dentist in impression material 122 such that the entire outer surfaces of the copings 110 extending above the surface of the mucosal tissue on the patient's mandible 100 are completely covered. The impression material is left in this position to cure. Once cured, the individual copings 110 are fixed with respect to each other in the same position and orientation that the anchors 104 are fixed with respect to each other. The curing process fixes the copings in this position and thereby permits the copings to be collectively removed together with the impression material while preserving their orientation.

In the next step of the process, the dentist flexes the tray 120 and the now-cured impression material 122 and removes them from the patient's mouth. Enough impression material 122 is placed in the tray and disposed around the patient's mandible 100 to cover any still-existing teeth of the mandible and the mucosal tissue 102 of the mandible as well as the copings 110.

When the tray 120 and impression material 122 are removed, the copings are removed with them, embedded in the now-cured impression material 122. The process of removal disconnects the copings 110 from the anchors 104, permitting the copings to be removed while still embedded in the impression material 122. If the copings include a threaded portion that holds them to the anchors, this threaded portion is unthreaded from the anchors. If the copings are fastened to the anchors with a snap fastening portion, the snap fastening portions are unsnapped from each other. The now-cured impression material 122 that couples the copings 110 to each other preserves the relative positions and orientations of the mating surfaces of all the copings 110 and hence relative positions and orientations of the mating surfaces 108 of all the anchors 104 with respect to each other. This relationship is preserved in the relative positions and orientations of the surfaces of copings 110 that were connected to the mating surfaces 108 of anchors 104. The impression material 122 in which copings 110 are embedded also preserves the surface contours of the mucosal tissue and the remaining teeth (if any) in the mandible and their relative positions with respect to the mating surfaces of copings 110 and anchors 104. The surface of the impression material 122, once removed from the patient's mouth, is a negative replica of the soft tissue and teeth. The surfaces of copings 110, now separated from anchors 104 and exposed on the inside surface of the impression material 122, are a negative replica of surfaces 108 of anchors 104 to which they were coupled. The now-cured impression material 122 is therefore a negative replica of all the free surfaces, including teeth, mucosal tissue, and the surfaces of the copings embedded in the impression material are a negative replica of the mating surfaces 108 of anchors 104. The cured impression material with embedded copings is commonly called an "impression" and identified in the figures herein as item 123.

Figure 6:
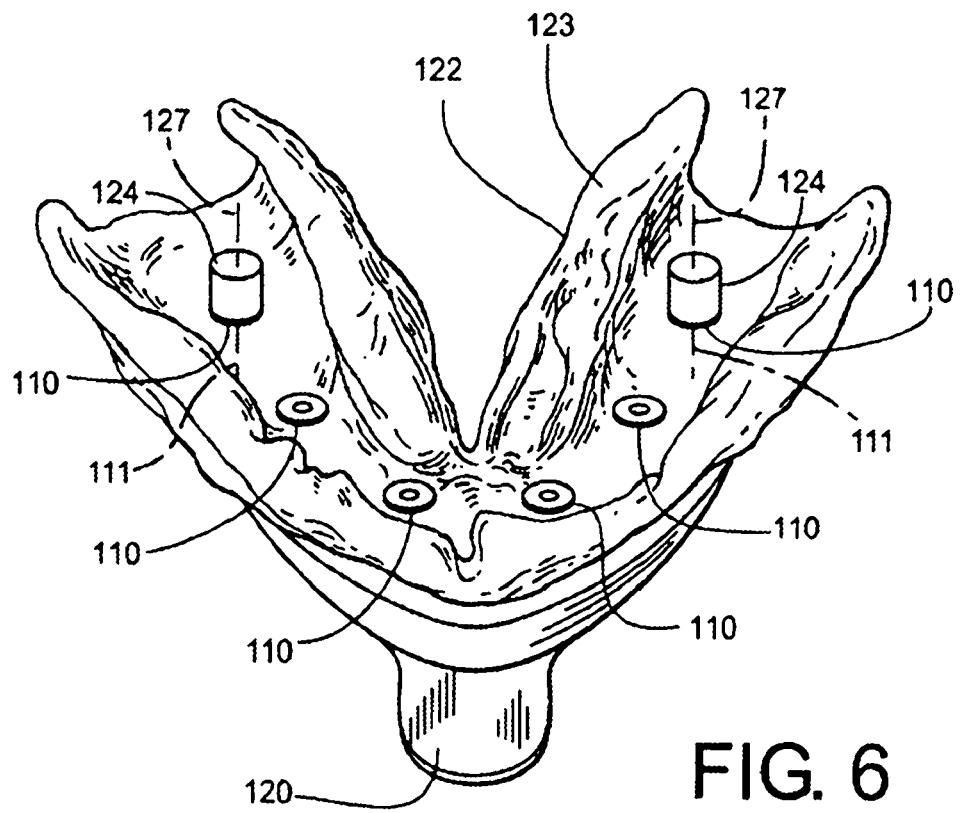
FIG. 6 is a perspective view of the impression of FIG. 5 inverted and removed from the patient's mouth with two analogs attached to two of the copings.

FIG. 6 shows the impression 123 inverted and removed from the patient's mouth. In this embodiment, there are six copings 110 embedded in the impression 123. The bulk of the copings 110 are embedded in the impression 123. Only the very ends of the copings 110 extends upward and out of the impression 123 (in this inverted orientation).

In FIG. 6 the dentist has begun the next step of the process, that of attaching analogs 124 to the exposed surfaces of all of the copings 110. Analogs 124 are structures that replicate the anchors 104. As in the case of the copings themselves, each analog 124 preferably comprises a generally cylindrical body with a longitudinal axis 127 that is coaxial with the longitudinal axis 111 when attached to coping 110.

The end surfaces of analogs 124 are configured to abut and mate with the free surfaces of the copings 110 that were previously coupled to anchors 104. The surfaces of analogs 124 replicate the position and orientation of mating surfaces 108 of anchors 104. In effect, the spacing and orientation of anchors 104 was transferred to the copings 110, and transferred back again to analogs 124, which have the same spacing and orientation as the anchors 104. Thus, each analog 124 is coaxial with and is disposed in the same position as anchor 104.

Figure 7:
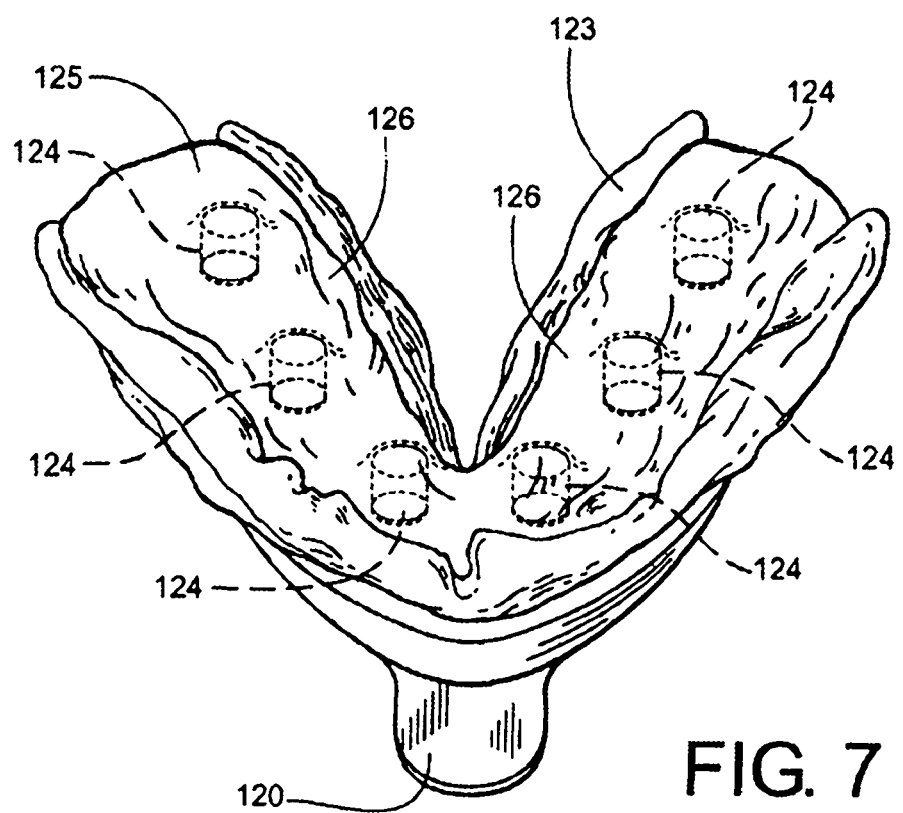
FIG. 7 is the same perspective view of FIG. 6, but with all the analogs attached to all the copings, and the impression filled with dental stone material and all the analogs submerged in the dental stone material.

In the next step of the process, illustrated in FIG. 7, the dentist pours a mixed dental stone material 126 into the cavity in impression 123 that was formed by the patient's mandible, submerging all of the analogs 124. Stone material 126 covers the exposed portion of the analogs 124 as well as the surfaces of impression 123 formed by the patient's mucosal tissues and teeth. Once filled into impression 123, the stone material 126 is then permitted to harden to a rock-like consistency, creating a structure that is called a "stone cast" 125.

Figure 8:
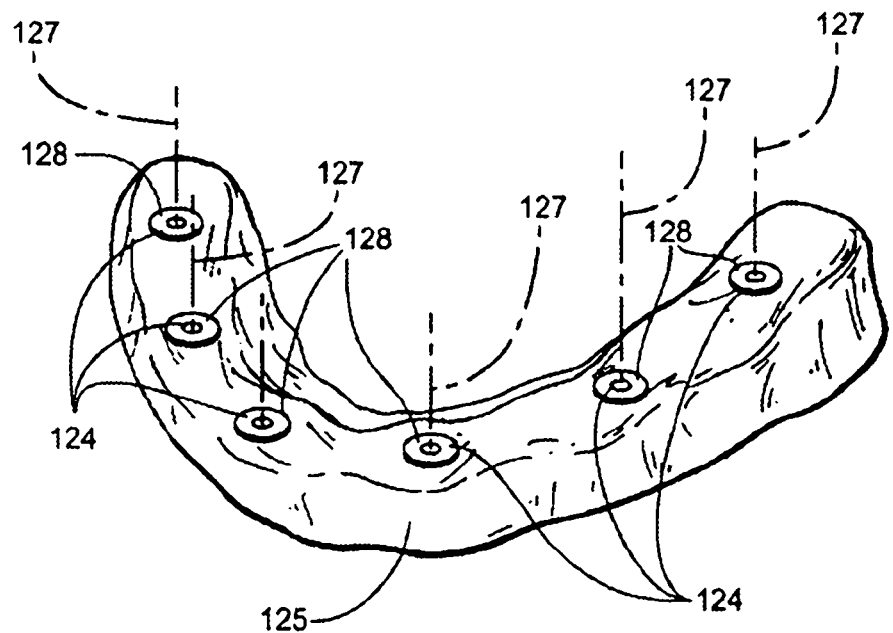
FIG. 8 is a perspective view of the stone cast formed by the dental stone material poured in the impression of FIG. 7 in its hardened state, inverted, and with the impression removed showing the analogs with the analog surfaces that mated with the copings in FIG. 7 now exposed.

FIG. 8 represents the next step of the process which the dentist performs once the stone material 126 has hardened. The dentist removes impression 123 from the stone cast 125, leaving the stone cast 125 with the analogs embedded therein. The stone cast 125 positively replicates the position and orientation of mating surfaces 108 of anchors 104, which are represented in the stone cast 125 by the mating surfaces 128 of the analogs 124 that were fixed to the free ends of copings 110 (FIG. 6). The portions of the stone cast 125 surrounding analogs 124 positively replicates the surface of the mucosal tissues of the mouth, which were transferred from the mucosal tissues of the mouth to the impression as a negative replica and then back to the stone cast as a positive replica of those tissues. The stone cast 125 also replicates the surface of the patient's existing teeth (not shown). When the patient has existing teeth, the position and orientation of the surfaces of the teeth are transferred first to the impression as a negative replica and then to the stone cast as a positive replica. In the present embodiment, the mandible 100 is edentulous and therefore there are no existing teeth.

As will be explained later, teeth that are replicated in impression 123 and stone cast 125 provide a precise reference to indicate the location of the jawbone. The soft tissues that are replicated in the impression 123 and stone cast 125 can change their position due to swelling, edema, injury, irritation, or damage to the mouth. Teeth, since they are much harder and are embedded in the jawbone, provide a more stable reference, over time, of the position of the jawbone and thus indirectly, of the position and orientation of anchors 104.

The impression molding and stone casting processes described above provide accurate replicas of the position and orientation of the mating surfaces 108 of anchors 104, the mucosal tissues, and the teeth.

In the preferred embodiment, the mating surfaces 108 of anchors 104 are exactly duplicated by the mating surfaces 128 of the analogs 124: they are in exactly the same position and at exactly the same orientation. In an alternative embodiment, the mating surfaces 128 on the analogs may be offset slightly or configured slightly differently than the mating surfaces 108 of anchors 104. In some cases, manufacturers choose to make analogs or other connecting components that have mating surfaces slightly different from the mating surfaces 108 of the anchors 104 for example to permit the copings 110 to be more easily attached to anchors 104 or to permit analogs 124 to be more easily attached to copings 110. Any slight difference in position such as this is intentional, however, and is eliminated later in the process when the denture is created so that the mating surfaces of the denture are precisely oriented to mate properly with surfaces 108 of anchors 104 in the patient's mouth.

Further, the anchors 104 in the patient's mouth may not be connected directly to the dental framework. Abutments may be mounted on the anchors 104 (i.e. the anchors have sur-mounted abutments). The dental framework may be mounted to these abutments, and thus indirectly mounted to anchors 104. When the dental framework being designed is intended to be mounted on abutments mounted on anchors 104, the analogs 124 may be provided with surmounted abutments, i.e. the analogs may include the abutment design incorporated into it, to replicate the mating structure of the abutment to the framework.

While the mating surfaces 128 of the analogs 124 and the mating surfaces 108 of anchors 104 may be slightly differently configured, the longitudinal axes of each of the anchors 104 and the analogs 124 are preferably identically oriented and spaced apart, each pair of corresponding analog and anchor sharing a common longitudinal axis (i.e. they are coaxial). Considered differently, if the surface of the stone cast representing the soft tissues and teeth of the patient's mouth could be superimposed on top of the patient's mucosal tissues 108 that formed the stone cast 125, all the longitudinal axes defined by the analogs would be superimposed on (i.e. simultaneously coaxial with) all the corresponding axes defined by the anchors. The longitudinal axes 127 of the analogs 124 and the surfaces of the stone cast 125 defined by the mucosal tissues 108 the patient are positive replicas of the longitudinal axes 111 of anchors 104 and the surfaces of mucosal tissues 108.

The replica of any teeth formed in the surface of the stone cast are formed with respect to one another and with respect to the analogs such that they duplicate the position of any existing real teeth in the patient's mouth with respect to one another and with respect to mating surfaces 108 and longitudinal axes of the anchors 104 in the patient's mandible. The replica of the mucosal tissues formed in the surface of the stone cast are in generally the same position on the stone cast as they are in the patient's mouth including the replication in the stone cast 125 of the junction between the mucosal tissue and any existing teeth and anchors 104, as well as a replication in the stone cast of all the mucosal tissue that will be covered by the denture.

Once the dentist has created the stone cast 125, which is a positive replica of the patient's jaw, including replication of existing teeth, mucosal tissue, and anchors, the dentist then proceeds to the next step in the process: designing and creating the denture that will be fitted to the patient's mouth (in this case, the patient's jaw).

The dentist manually creates a diagnostic wax-up 130 of the desired denture teeth position and occlusal orientation, using flexible molding materials such as wax, acrylic, and other polymers.

The diagnostic wax-up 130 is created to verify the proper location of the denture mucosal tissue and denture teeth with respect to the patient's actual mouth to ensure proper tooth orientation, and to ensure that the location and placement of the denture within the patient's mouth restores form, fit and function. In short, the diagnostic wax-up 130 is a model of and looks like the denture that is ultimately produced, but is made of softer materials to permit it to be adjusted and adapted until the patient and dentist are pleased with its form, fit and function.

The dentist creates the wax-up 130 on the stone cast, building it up on the patient's replica mucosal tissue. When the dentist is finished making the wax-up 130, he removes the wax-up 130 from the stone cast 125, and places it into the patient's mouth so the patient can see, firsthand, what the denture will look like when it is finished. If the wax-up 130 fits, the patient can bite properly, and the patient is pleased with the appearance of the wax-up 130, the dentist then proceeds to manufacture the denture.

Figure 9:
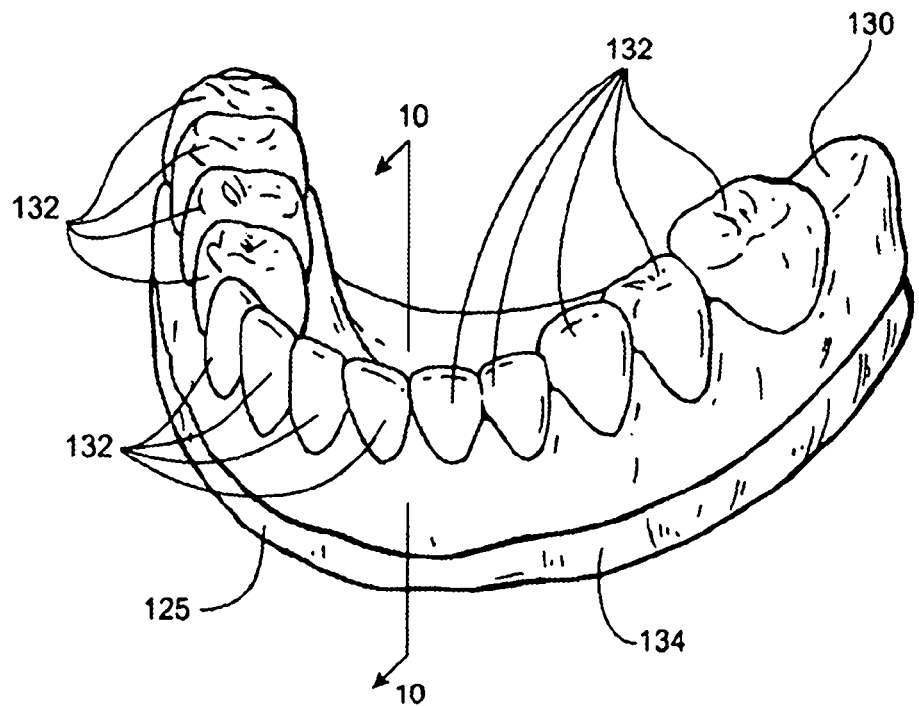
FIG. 9 is a perspective view of the stone cast of FIG. 8 with the dentist's manufactured diagnostic wax-up that was previously built up on the top of the mandible now disposed on the stone cast and abutting the analogs.
Figure 10:
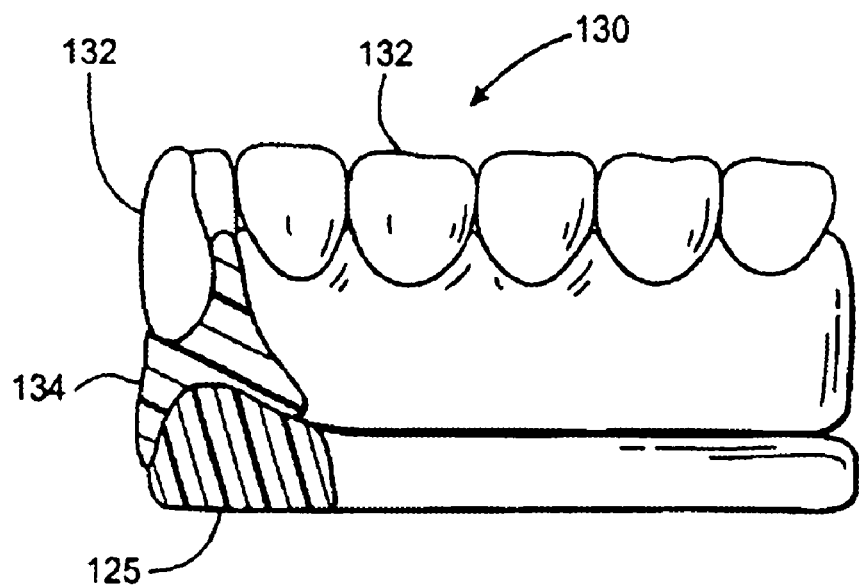
FIG. 10 is a cross-sectional view of the stone cast of FIG. 9 taken at section line 10-10 in FIG. 9.

FIGS. 9-10 illustrate the process of creating a wax-up, showing the stone cast 125 as it would appear with a wax-up 130 modeled on its outer surface. In FIG. 9, the stone cast 125 is shown covered with the wax-up 130 which comprises the denture teeth 132 embedded in wax 134 which the dentist has molded directly to the surface of the stone cast 125. FIG. 10 is a cross-sectional view through the stone cast 125 plus wax-up 130 assembly shown in FIG. 9. This cross-section is taken at section line 10-10 in FIG. 9.

Figure 11:
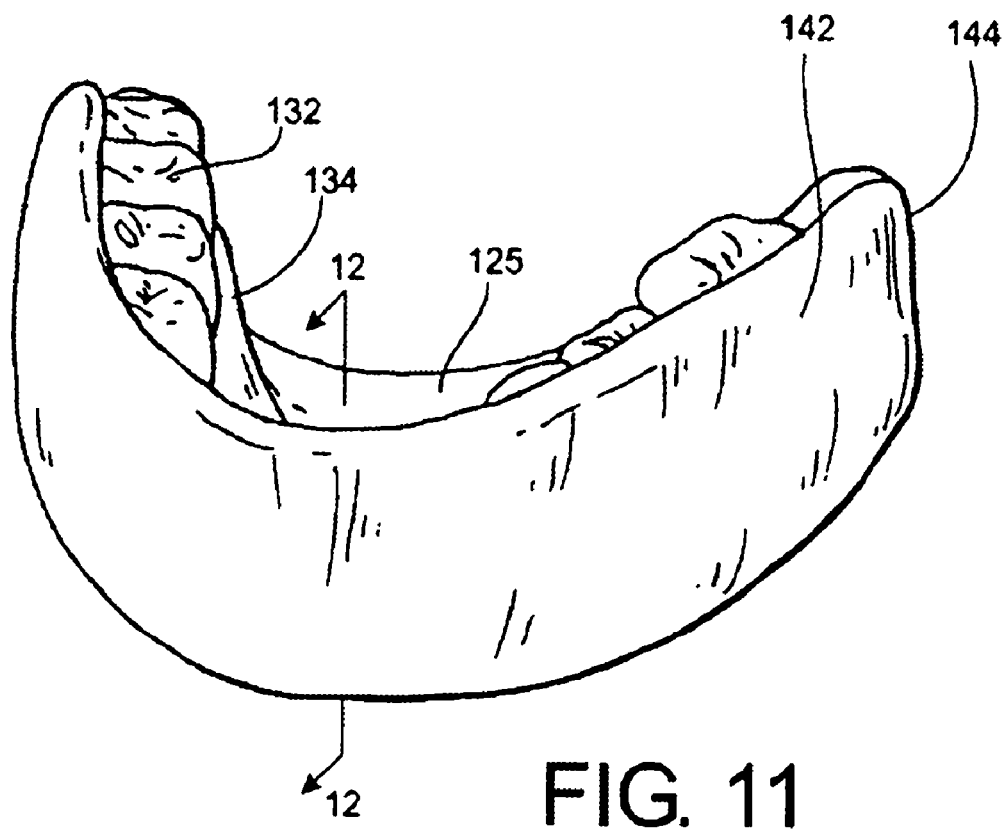
FIG. 11 is a perspective view of the stone cast of FIGS. 8-10, with a putty index molded to the facial aspect of the diagnostic wax-up.
Figure 12:
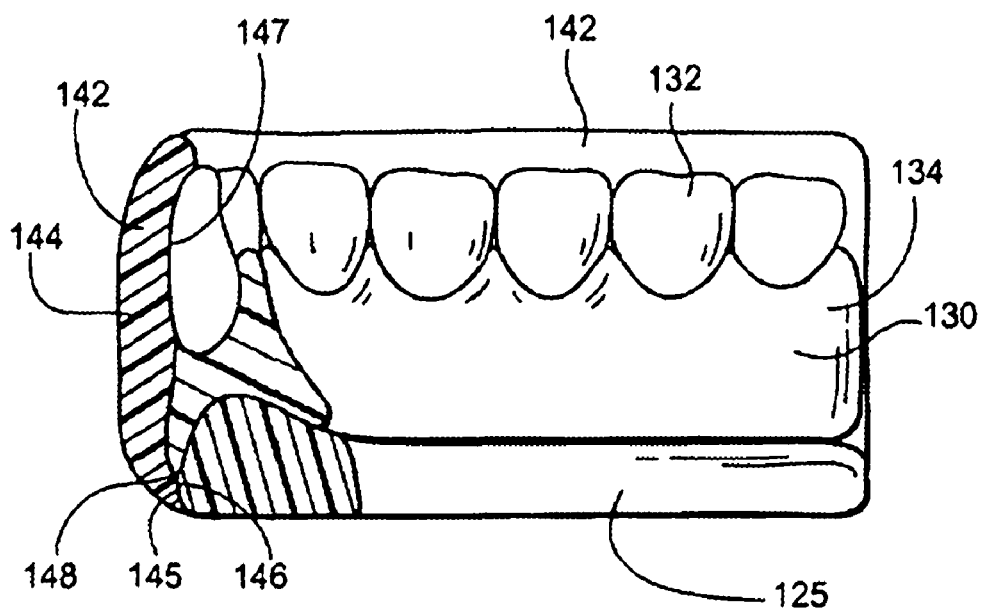
FIG. 12 is a cross sectional view of the stone cast of FIGS. 8-11 taken at section line 12-12 in FIG. 11.

Once the dentist has created the wax-up 130 and has verified the fitting of the wax-up 130 in the patient's mouth, he then proceeds to the next step in the process, which is illustrated in FIGS. 11-12. In this step, he removes the wax-up 130 from the patient's mouth, and places it back on stone cast 125. He then creates a negative replica 142 of the facial form of wax-up 130 called a "putty index" (or as it is alternatively and equivalently called: a "facial index").

To create the putty index 142, the dentist molds silicone putty 144 directly to the facial surface of wax-up 130 including the teeth 132 and the wax 134 that represents the artificial mucosal tissue portion of the denture. This silicone putty 144 extends beyond the edges of wax-up 130 to the adjacent surfaces of stone cast 125.

FIG. 11 shows the silicon putty, already solidified, surrounding the wax-up 130 on stone cast 125. FIG. 12 is a cross-section through the stone cast/wax-up/silicon putty of FIG. 11, taken at section line 12-12 in FIG. 11. Referring now to FIG. 12, we can see that silicon putty 144 has been manually molded on to the surface of the stone cast 125 adjacent to wax-up 130, at junction 145, for example.

Figure 12B:
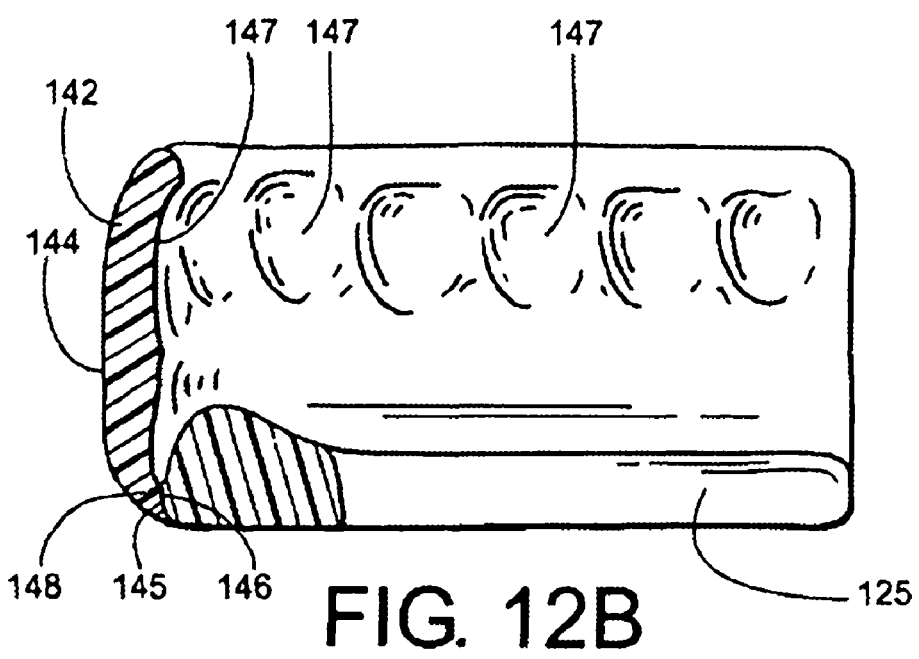
FIG. 12B is a cross sectional view of the stone cast of FIGS. 8-12 with the diagnostic wax-up removed to show the inner surface of the putty index and the impression of the facial aspect of the diagnostic wax-up formed on the inner surface of the putty index.

In the next step, the dentist removes the now-solidified silicon putty 144 (i.e. putty index 142) from the stone cast 125 and wax-up 130, removes the wax-up 130 from the stone cast 125 and replaces the putty index 142 on the stone cast 125 in its original position, as shown in FIG. 12B.

This removal creates an outline form 147 formed on the inner surface of the putty index 142 that is the exact size and shape of the facial aspect of the wax-up 130. Outline form 147 is a negative replica of the teeth 132 of wax-up 130, the mucosal tissue formed in wax 134 that surrounds and supports the teeth 132.

When forming the putty index 142, the dentist extends the silicone putty 144 beyond the edge of the wax-up at junction 145 and abuts the stone cast 125 to form a direct junction between the putty index 142 and the stone cast 125. This abutting relationship molds the two surfaces together and permits the dentist to orient the putty index 142 in its as-formed position with respect to stone cast 125. The dentist does this by aligning surfaces 146 of the putty index 142 that were molded in abutment to surfaces 148 of the stone cast 125. Surface 148 is a negative replica of surface 146.

As in the case of many irregular surfaces, such as the mating broken edges of two pieces of pottery, a surface portion of stone cast 125 mates with the surface on putty index 142 on which it was formed to define a very precise assembled orientation that is easy to recreate once wax-up 130 is removed.

Figure 13A:
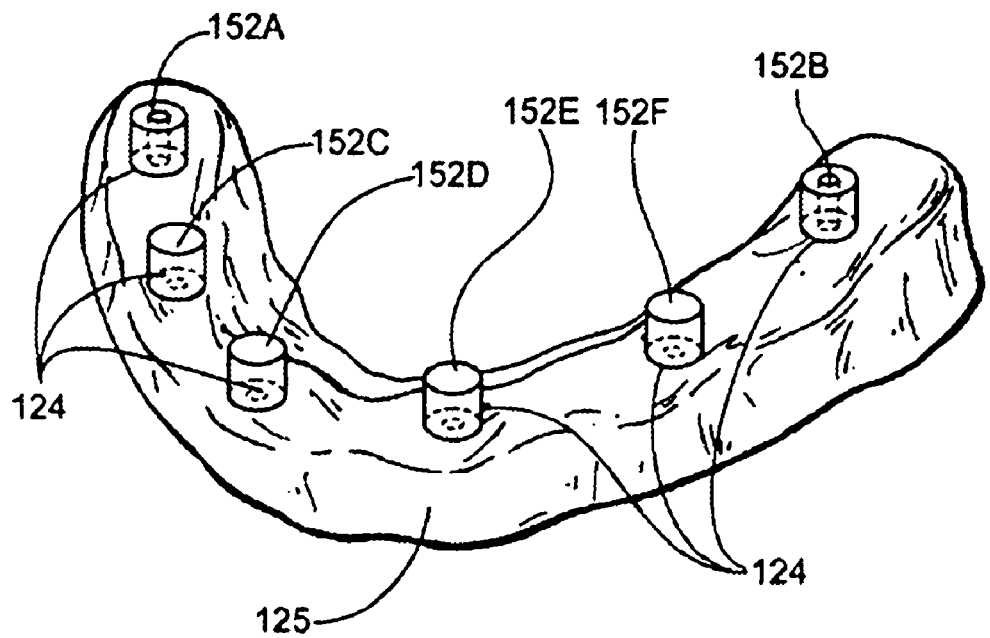
FIG. 13A is a perspective view of the stone cast of FIGS. 8-12B with six fittings, one fitting attached to each of the six analogs.
Figure 13B:
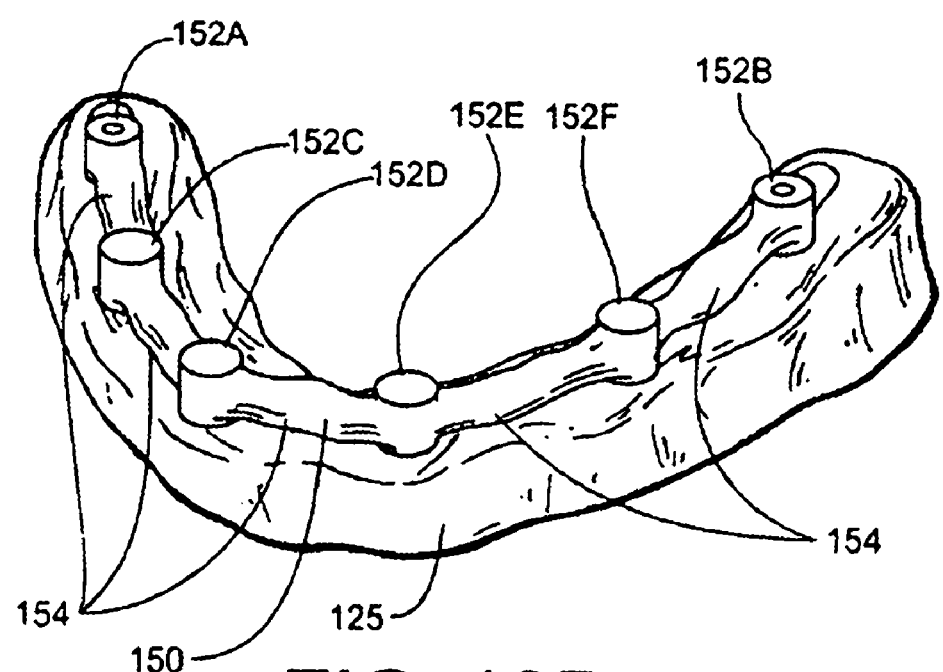
FIG. 13B is a perspective view of the stone cast of FIGS. 8-13A with bridging structures fixed to and between each of the six fittings to form a wax-up framework mounted on the six analogs.

With the putty index 142 created, the dentist can proceed to the next step in the process, illustrated in FIGS. 13A, 13B, in which the dentist molds a wax-up framework 150. Wax-up framework 150 is later duplicated in metal and embedded in the plastic body of the denture to support the denture on anchors 104 in the patient's mouth.

With the putty index 142 removed, the dentist fixes precision copings or fittings 152 that are typically provided by the manufacturer of analogs 124 and are configured to mate with the analogs. These are shown in the figures as items 152A-152F and are attached to the mating surfaces 128 of analogs 124 extending from stone cast 125 (FIG. 13A). The analogs 124 embedded in stone cast 125 orient fittings 152 precisely with respect to one another to replicate the position and orientation of anchors 104. In short, the stone cast holds fittings 152 in the same position with respect to each other in which they would be held by anchors 104 if they were inserted into the patient's mouth instead of being fastened to the analogs 124.

Referring now to FIG. 13B, once the dentist has attached fittings 152 to analogs 124, he then proceeds to create a bridging structure 154 of the framework 150. Bridging structure 154 is typically formed from a moldable wax/acrylic material. The dentist manipulates this material and extends it as a narrow band adjacent to the surface of stone cast 125 until each of the fittings 152 are coupled together with bridging structure 154 (FIG. 13B) to form a single structure.

The dentist must verify the wax-up framework 150 before he can cast it in metal, however. In order to verify the wax-up framework 150, the dentist must fit the putty index 142 (whose outline form 147 negatively replicates the position and orientation of the facial surface of diagnostic wax-up 130 and thus the facial surface of the denture) to ensure that wax-up framework 150 is enclosed within the putty index where desired, and therefore will be embedded within the denture material when the denture is finally created. Portions of the wax-up framework 150 may be deliberately designed to extend outside of the denture and reach remote anchors 104 to provide additional stability. Typically, however, the framework is completely embedded within the denture material that replicates the mucosal tissue. By testing the shape of the framework (typically by repeatedly placing and removing the putty index from the stone cast 125 in front of the wax-up framework 150) as the dentist builds the framework, the dentist can build and adjust the bridging structure 154 of the framework until it is disposed well back from the outline form 147 of the putty index in a position where it will provide the most support for the denture teeth and the denture gum material that supports the denture teeth.

FIG. 13B illustrates stone cast 125 with wax-up framework 150 including bridging structure 154 extending across the surface of the stone cast 125 and coupling together all of the fittings 152 coupled to the mating surfaces 128 of analogs 124 that extend outward from the stone cast 125. In the next step, the dentist detaches the wax-up framework 150 from stone cast 125.

Figure 13C:
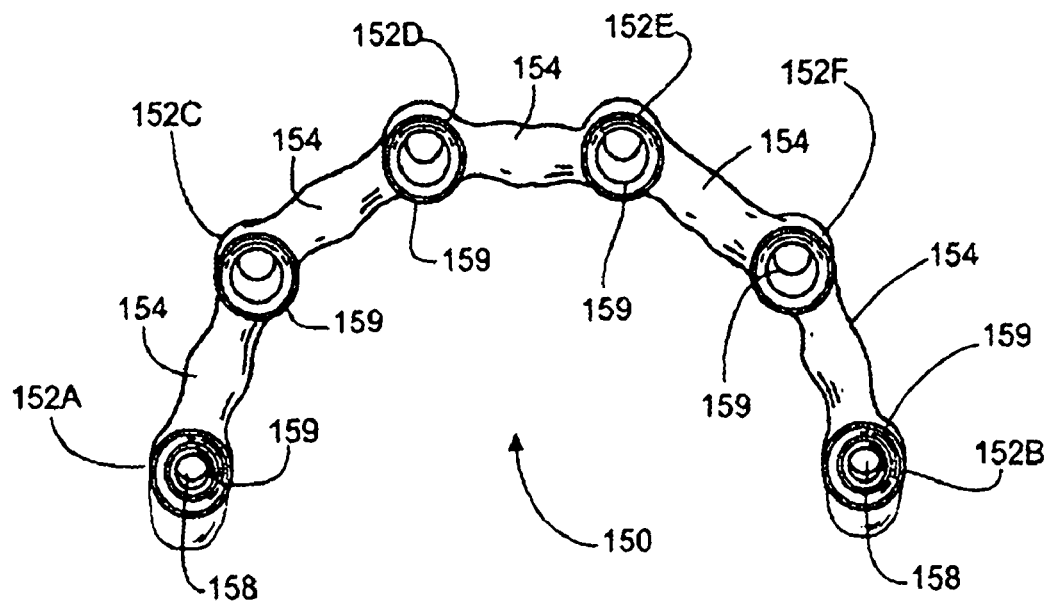
FIG. 13C is a bottom view of the wax-up framework of FIGS. 13A-13B as it would appear when removed from the stone cast and inverted.

FIG. 13C illustrates wax-up framework 150 as it would appear detached from stone cast 125 and inverted, exposing surfaces of fittings 152 that mate with analogs 124. Fittings 152 include two fittings 152A, 152B that have cylindrical or frusto-conical recesses 159 with apertures 158 extending completely through fittings 152 and wax-up framework 150. Apertures 158 are configured to receive screws that are attached to anchors 104 in the patient's jaw. The other four fittings 152C, 152D, 152E, 152F do not have apertures 158 but do have cylindrical or frusto-conical recesses 159 common to all the fittings 152. They are configured to be supported on mating cylindrical or frusto-conical posts (not shown) that will be an integral part of anchors 104 or that will be attached to the anchors 104. In the illustrated embodiment the two rear fittings 152A, 152B are configured to be fixed to anchors with screws passing though apertures 158. In an alternative embodiment, any of the other fittings 152 (or none, or all) may be provided with apertures or other means for attaching the fittings 152 to anchors 104.

It should be remembered that wax-up framework 150, fittings 152 and bridging structure 154 are never intended to be mounted to anchors 104 in the patient's mouth. Instead, a duplicate is made of wax-up framework 150 out of much stronger materials that is inserted in the patient's mouth. It is the duplicates of fittings 152 in the final framework that actually mount to anchors 104.

For that reason, in order for the duplicates of fittings 152 formed in the final framework to mount properly to anchors 104 in the patient's mouth, fittings 152 themselves must be configured to mount to anchors 104. If they are not configured to mount to anchors 104, then their duplicates in the final framework will not mount to anchors 104.

To configure the fittings 152 for mounting to the patient's jaw, each of fittings 152 illustrated in the figures has at least one surface portion configured to mate with anchors 104. Thus, the final framework can be fixed to analogs 124. Since analogs 124 are mounted to and axially oriented to copings 110 (FIG. 13A), and since copings 110 were initially fixed to and coaxial with anchors 104, fittings 152 are configured to be fixed to and coaxial with anchors 104

Each mating surface on fittings 152 is symmetric about a longitudinal axis that extends through that fitting and are coaxial with the analogs 124 on which they are mounted. In this case, the surfaces are those interior to frusto-conical recesses 159. This should not suggest that the mating surfaces must have any particular shape or orientation. Generally speaking, the mating surfaces may be concave or convex, they may be conical, cylindrical, circular, or parabolic. Regardless of their shape, each fitting 152 has at least one mating surface that preferably defines a longitudinal axis, and more preferably each of the mating surfaces is a surface that is symmetric about that longitudinal axis. It is these surfaces when duplicated to create the metal framework that orient the metal framework with respect to anchors 104. Hence the longitudinal axes defined by the mating surfaces of fittings 152 replicate the longitudinal axes of anchors 104.

Once the dentist has created the wax-up framework 150, he sends the wax-up framework 150 to a laboratory for further processing.

Figure 14:
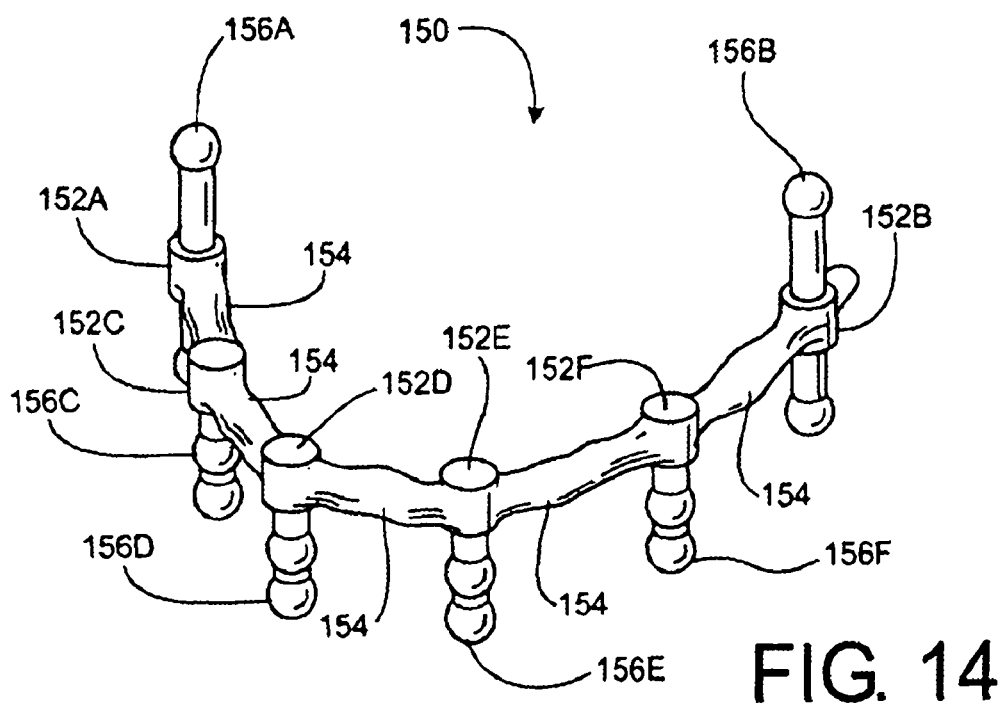
FIG. 14 is a perspective view of the removed wax-up framework of FIG. 13C with an alignment post attached to each of the six fittings.

In the next step of the process, and referring to FIG. 14, a technician inserts alignment posts 156 (shown in the figures as items 156A, 156B, 156C, 156D, 156E, 156F) into fittings 152. Alignment posts 156 engage the surfaces of fittings 152 that are configured to engage surfaces 108 of anchors 104. Alternatively, they are inserted such that they abut other surfaces of fittings 152 that are not configured to engage anchors 104 but are in a known pre-determined position and orientation with respect to surfaces 108 of anchors 104. Alignment posts 156 have a longitudinal axis that is preferably coaxial with fittings 152 when they are mounted to fittings 152. Since they are coaxial with fittings 152, they are also coaxial with anchors 104. As described in the process above, anchors 104 transfer their position and orientation to copings 110, which transfer their position and orientation to analogs 124, which transfer their position and orientation to fittings 152, which transfer their position and orientation to posts 156. Thus posts 156 are coaxial with fittings 152, analogs 124, copings 110 and anchors 104.

In the next step of the process, the surfaces of wax-up framework 150 and the alignment posts 156 are electronically scanned, preferably by a laser scanner or alternative devices such as an optical, light, touch probe, or CT scanner.

The scanner is configured to generate a plurality of three-dimensional position data or points that represent the three-dimensional coordinates of each scanned point on the surface of wax-up framework 150 and alignment posts 156. The scanning process need not scan all points on the surface of wax-up framework 150, nor does it need to determine each point on the surface with the same accuracy. The particular location of points on the surface of bridging structure 154 may not be as critical as points on the surfaces of the fittings 152. Points on the surfaces of fittings 152 represent points on the surfaces of the metal framework made from the wax-up framework 150, including points that will mate with mating surfaces 108 of anchors 104. The relative position of the mating surfaces of fittings 152 ultimately determine the quality of the denture fit and the loads placed on anchors 104. In contrast to this, some error in determining the surface of bridging structure 154 can be tolerated more easily, since any errors in determining the surface of bridging structures 154 will be accommodated when the denture material is processed around the outside of the metal framework.

The alignment posts 156 are used to provide a more accurate determination of the position and orientation of the surfaces of fittings 152 that, when duplicated in metal will engage mating surfaces 108 of anchors 104. The alignment posts provide several extension surfaces that have a predetermined orientation and location with respect to the mating surfaces of fittings 152 (and hence with respect to mating surfaces 108 of anchors 104). The surface extensions provided on posts 156 preferably have a larger surface area than the mating surfaces of fittings 152 to which they are coupled. The surface extensions provided on posts 156 preferably have a well-defined geometry that, when scanned, provide scanner position data bearing a known spatial relationship to the mating surfaces on posts 156 that can be easily processed by a digital computer to generate a much more accurate estimation of the position of the mating surfaces of fittings 152 (and hence mating surfaces 108 of anchors 104 on which the denture will be mounted) than can be provided by directly scanning those surfaces of posts 156 directly with the scanner.

Each of anchors 104, and its corresponding copings 110, analogs 124, and fittings 152 preferably share a common longitudinal axis about which their respective mating surfaces, whatever their shape, are revolved. To determine the orientation and position of the surfaces, and particularly to determine the orientation of the surfaces on fittings 152 that are configured to mate with mating surfaces 108 of anchors 104, the scanner, or the computer processing the data provided by the scanner, determines (1) the orientation of that longitudinal axis in three dimensions, and the particular point along that longitudinal axis where the mating surfaces are located. The mating surfaces may have slightly different profiles, they may have slightly different surface contours, they may be disposed at different positions along the longitudinal axis. Nonetheless, they all bear a distinct, repeatable, and predetermined position and orientation with respect to each other.

Figure 15:
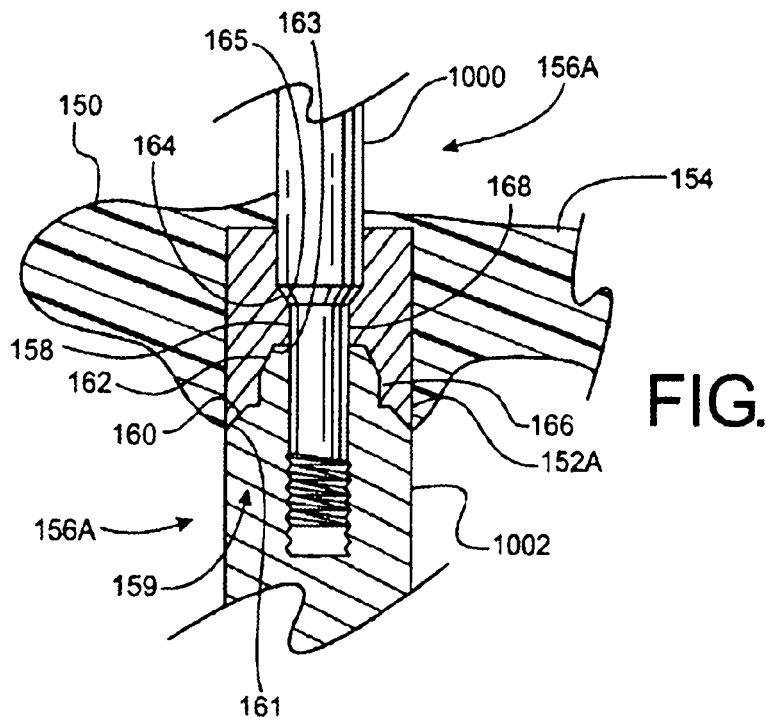
FIG. 15 is a cross sectional view of the wax-up framework of FIG. 14 with alignment posts attached taken along the longitudinal axis of either one of the two end alignment posts and its associated fitting.

In FIG. 15, alignment post 156A is preferably made of two separate structures (shown as post portions 1000, 1002) that are inserted into opposite sides of aperture 158. Post portions 1000, 1002 of alignment post 156A, abut surfaces on opposite sides of wax-up framework 150. In the preferred embodiment, post portion 1000 of alignment post 156A extends into aperture 158 in fittings 152A, and is threadedly engaged to post portion 1002 of alignment post 156A extending into aperture 158 from the other side of the wax-up framework 150. Pin portion 1000 has external threads that are coupled to and engage mating internal threads of pin portion 1002.

Fitting 152A (FIG. 15), has several surfaces that engage alignment post 156A. These include frusto-conical sections 160, 162, 164 as well as cylindrical sections 166, 168. Frusto-conical sections 160, 162 engage matching frusto-conical portions 161, 163 of the shank of post portion 1002. Frusto-conical section 164 engages a matching frusto-conical section 165 of the shank of post portion 1000. Tightening post portions 1000, 1002 by threading one into the other through aperture 158 causes the compressive forces exerted on the frusto-conical and cylindrical sections 160, 162, 164, 166 and 168 to align the longitudinal axes of post portions 1000, 1002 coaxial with each other and coaxial with the longitudinal axis of fitting 152A to which they are attached.

When tightened, the relative position of alignment post 156A indicates the location in three dimensions of the mating surfaces of fitting 152A and the angular alignment of those mating surfaces in three dimensions. They indicate the position and longitudinal axis of fittings 152A. Post 156A self-aligns with respect to fitting 152A in a predetermined relative orientation when post 156A is tightened on fitting 152A.

For convenience and economy of illustration, only fitting 152A and alignment post 156A are illustrated herein. Since fittings 152A and 152B are identical to each other, and since alignment posts 156A and 156B are identical to each other, the description above of fitting 152A and its alignment post 156A applies equally to fitting 152B and its alignment post 156B.

There are four other fittings 152 comprising wax-up framework 150. They are identified as fittings 152C, 152D, 152E, and 152F. These fittings are identical as are their corresponding alignment posts 156C, 156D, 156E, and 156F.

Figure 16:
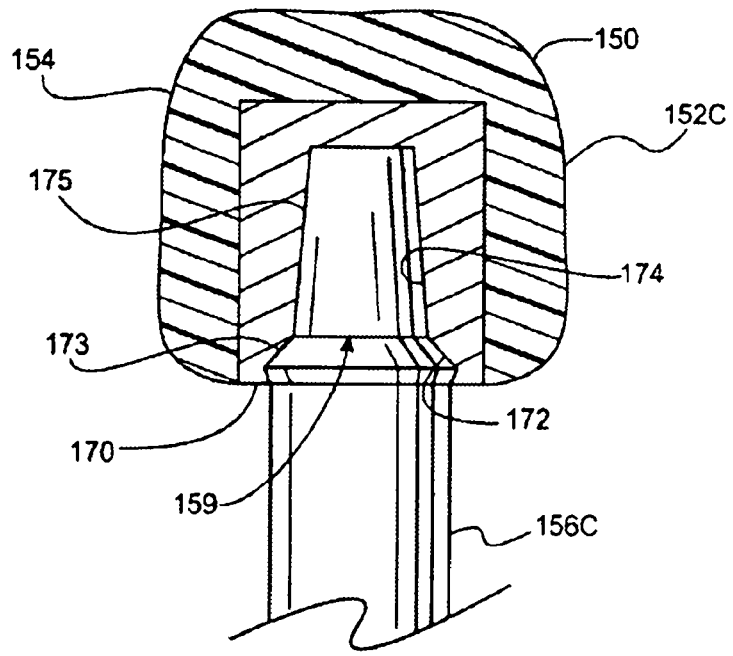
FIG. 16 is a cross sectional view of the wax-up framework of FIG. 14 with alignment posts attached taken along the longitudinal axis of any one of the four central alignment posts and its associated fitting.

For convenience and economy of illustration, only fitting 152C is shown in axial cross section in FIG. 16, coupled to its associated alignment post 156C. It should be understood that the other fittings and their corresponding alignment posts are identically configured and arranged and that the description below of fitting 152C and alignment post 156C applies equally to fittings 152D, 152E, 152F and alignment posts 156D, 156E, 156F.

Fitting 152C differs from fitting 152A in that it has no aperture 158 extending through the fitting. Instead, fitting 152C is generally cylindrical having a cylindrical or frusto-conical recess 159 with a generally flat bottom.

Recess 159 has two frusto-conical surface portions 172, 174 that engage mating frusto-conical surface portions 173, 175, respectively, on alignment post 156C. Surface portions 172, 174 are the surfaces that, when duplicated in the metal framework, mate with mating surfaces 108 of anchors 104 (or an intermediary component attached to anchor 104). These mating pairs of frusto-conical surface portions on the alignment post and on the fitting orient the alignment post with respect to the fitting such that the longitudinal axis of the fitting and the alignment post are the same. The position and orientation of alignment post 156C therefore indicates the position and longitudinal axis of fitting 152C. Since post 156C is fixed directly to fitting 152C, it represents the position and orientation of fitting 152C, and not the position and orientation of the bridging structure 154 that is fixed to and surrounds fitting 152C. Alignment post 156C is held in place in fitting 152C by frictional or snap engagement of an inwardly facing and flexible lip 170 that captures a flange extending outward from the periphery of alignment post 156C. This mechanical inter-engagement prevents post 156C from being withdrawn from fitting 152C without significant mechanical force being applied, however this mechanical engagement could be replaced by a screw retainment mechanism. It also holds post 156C in its proper and predefined (preferably coaxial) orientation with respect to fitting 152C. Post 156C is configured to self-aligns with fitting 152C in a predetermined relative orientation when it is attached. Fitting 152C is configured to hold post 156C in a specific alignment with respect to the fitting when assembled.

Figure 17:
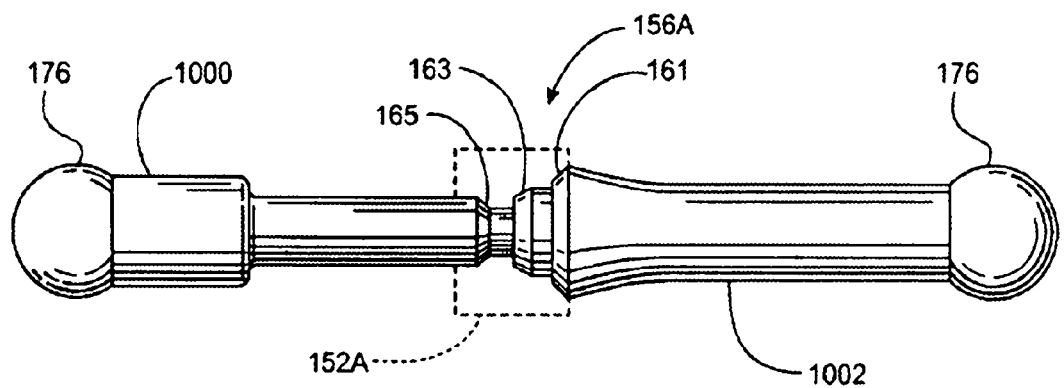
FIG. 17 is a side view of either one of the two end alignment posts (two-piece) of FIGS. 14-15 showing the fitting in which it is fitted in phantom lines.

FIG. 17 illustrates alignment post 156A in greater detail as it is aligned when tightened with fitting 152A (shown in phantom lines). As shown in FIG. 17, both of post portions 1000, 1002 of alignment post 156A are threaded together in a coaxial relationship as are when engaged and aligned to fitting 152A. Each of post portions 1000, 1002 is in the form of an elongated body having a predefined surface geometry (here shown as spherical outer surface portions 176) at one end of the post portion 1000, 1002 and the frusto-conical surfaces 161, 163, 165 disposed at the other end.

The spherical outer surface portions 176 on each of the alignment post portions 1000, 1002 of alignment post 156A (FIG. 17) are configured to have centers disposed on the longitudinal axes of each of the alignment post portions 1000, 1002 and are also concentric with the longitudinal axis of fitting 152A. The threads on alignment post portions 1000, 1002 are concentric as well. Furthermore, the cylindrical and frusto-conical surfaces on each alignment post portion are symmetric surfaces of revolution about the common longitudinal axis. Alternatively, other alignment posts with concentric geometrical shapes or even known irregular shapes can be used to identify the position and orientation of the fittings 152A.

As a result of this arrangement, when alignment post portions 1000, 1002 are threadedly attached to each other through aperture 158 in fitting 152A, the center points of each of the spherical outer surface portions 176 are disposed on the longitudinal axis of fitting 152A in which they are mounted. Furthermore, portions 176 are located at a predetermined distance apart from each other, and at a predetermined distance from the mating surfaces of the fitting 152A.

Figure 18:
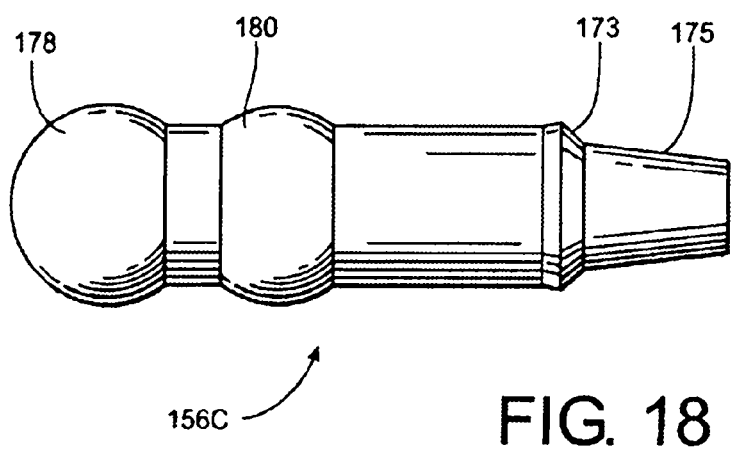
FIG. 18 is a side view of any one of the four central one-piece alignment posts of FIGS. 14, 16.

FIG. 18 illustrates alignment post 156C. This alignment post includes two spherical surface portions 178, 180. Spherical portion 178 is disposed at one end of the elongate alignment post 156C, and the two frusto-conical portions 173, 175 are disposed at the other end. Second spherical portion 180 is spaced apart from spherical portion 178, disposed partway between the two ends of post 156C. Both spherical surface portions 178, 180 have centers that are disposed on the longitudinal axis of post 156C. Frusto-conical surfaces 173, 175 are both symmetric surfaces of revolution about the longitudinal axis of post 156C. Alternatively, other alignment posts with concentric geometrical shapes or even known irregular shapes can be used to identify the position and orientation of the fittings 152C.

Figure 19:
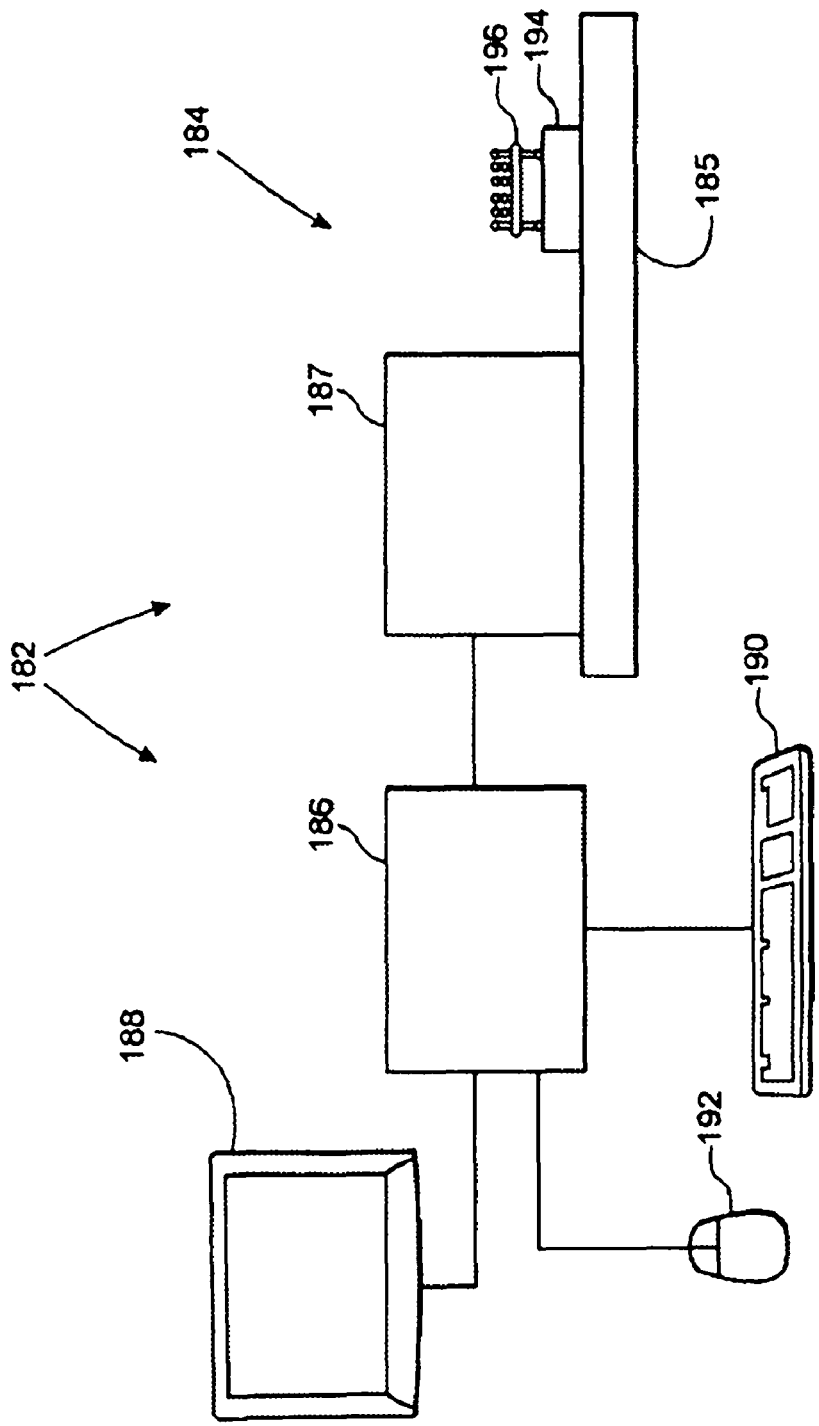
FIG. 19 is a schematic diagram of the scanner and the wax-up framework and alignment posts of FIG. 14 that it is scanning.

Referring now to FIG. 19, a scanner 182 including a scanning unit 184 having a chassis 185 and a laser probe 187, a digital microprocessor-based computer 186, a display screen 188, a keyboard 190, and a digitizer 192 are illustrated, together with wax-up framework/alignment post assembly 196 (see also FIG. 14) which is coupled to and supported on scanning unit 184 by a jig 194 mounted on chassis 185. Preferably a NEXTEC WizProbe.

Computer 186 is configured to control the scanning process and to interact with each of the other components, including the scanning unit, display screen, keyboard, and digitizer. Computer 186 includes a program that is configured to scan the surface of the framework/alignment post assembly 196 (comprising wax-up framework 150 and alignment posts 156) and to store coordinates of each point it scans on the surface of assembly 196 in its internal memory. The coordinates stored for each point are three-dimensional coordinates, sufficient to represent the position of each point in three dimensions. These positions may be absolute, or they may be relative with respect to a known position.

Scanning unit 184 is configured to scan assembly 196 under the control of computer 186 to which it is coupled. Scanning unit 184 preferably includes programmable mechanical positioning stages configured to change the relative position of the laser probe 187 with respect to the assembly 196 thus permitting scanner 182 to gather position data from the surface of assembly 196 from all sides. In addition, jig 194 may include mechanical positioning stages from which it can change the relative position of assembly 196 in relation to the laser probe 187.

The operator interacts with scanner 182 using display screen 188, keyboard 190, and digitizer 192 which are coupled to computer 186. Using keyboard 190 and digitizer 192 (preferably a mouse or digitizer pad), the operator enters commands that direct scanner 182 to perform the operations described herein. Display screen 188 is coupled to computer 186 to permit the operator to view the collected scanned surface point coordinates (point clouds) in three dimensions, to select various points of the point clouds for mathematical manipulation, to remove particular points from the point cloud, and to instruct the scanner 182 how to scan assembly 196.

Figure 20:
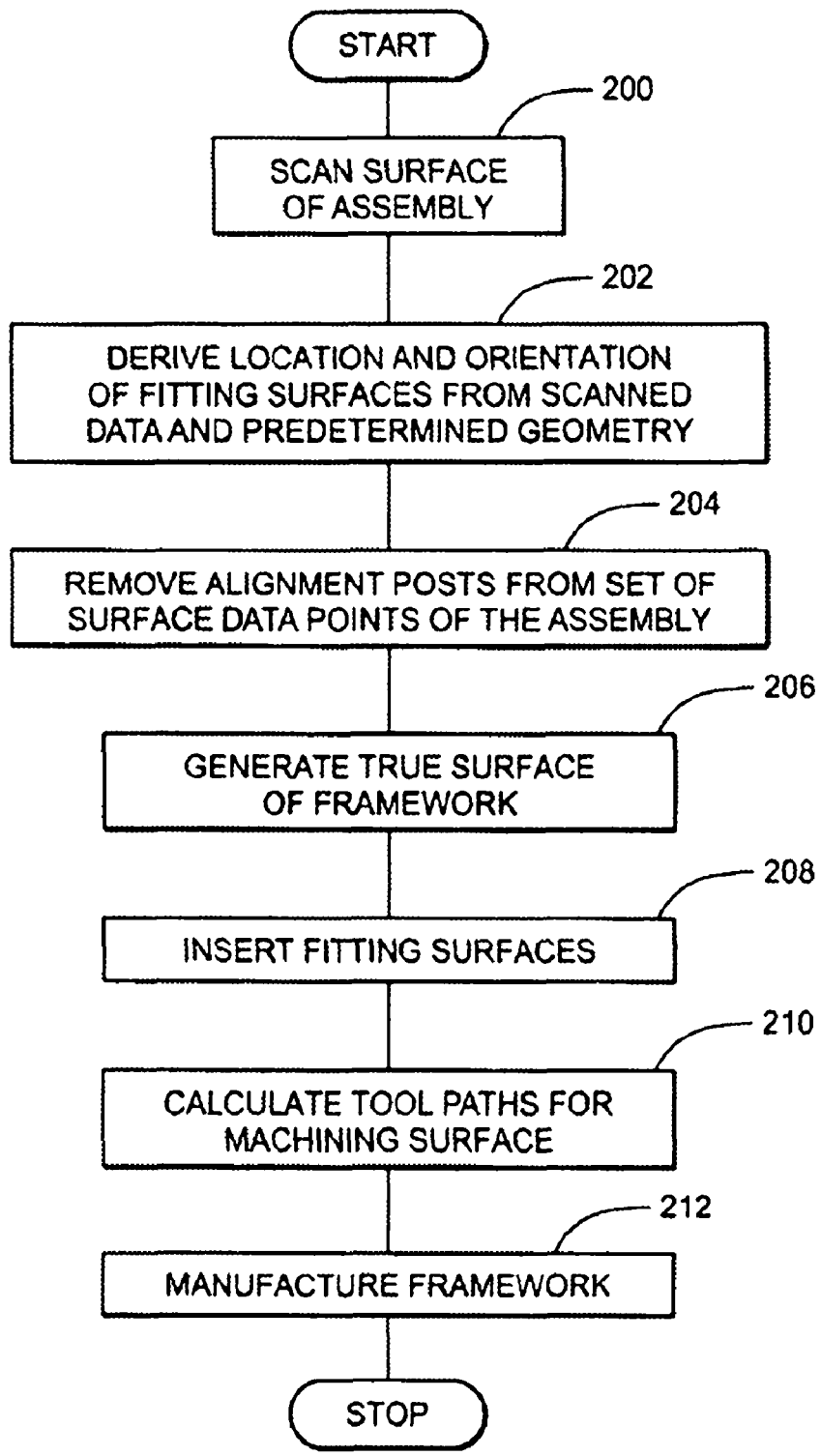
FIG. 20 is a flow chart of the process of scanning and manufacturing the framework of FIGS. 13A-14 with alignment posts attached as shown in FIGS. 14-16.

The process of manufacturing a dental framework from the wax-up framework 150, is shown in FIG. 20. The first steps of this process, described below, are the steps performed by the scanner 182 under the control of the scanner operator and computer 186. The computer instructions that configure the computer to perform these steps are stored in a digital memory of the computer 186.

In general, and as described below in greater detail, the process includes scanning the surface of the assembly 196 to determine the general overall shape of the wax-up framework 150. This shape, represented as a point cloud dataset, is a surface model of the wax-up framework in a preliminary form. This surface model is then further modified and refined by removing the points in the point cloud dataset representing the alignment pins and adding surface structures (typically in parameterized form and not as individual points) representing the surface of fittings 152 that will attach to anchors 104. This complete surface model is then used in subsequent manufacturing processes such as computer numeric controlled multi-axis machining, to create the framework for the denture.

In the first step of the framework manufacturing process, step 200, the computer 186 signals scanning unit 184 to scan the surface of assembly 196. Scanning unit 184 responsively scans the surface and transmits the coordinates of each point on the surface of the assembly 196 to computer 186. As necessary, computer 186 directs the scanning unit to reposition laser probe 187 with respect to assembly 196 in order to scan substantially the entire surface of assembly 196.

In the next step in the process, step 202, computer 186 derives the location of fitting surfaces from the predetermined geometry of the fittings 152 and the alignment posts 156 In the preferred embodiment, in order to determine the position of the mating surfaces of fittings 152 (and hence their position with respect to anchors 104 to which the final framework will be coupled), computer 186 is configured to use the geometry of the alignment posts 156 and the fittings 152 together with the coordinates of the point scanned on the surface of the alignment posts 156 to determine the precise location of the fitting 152 surfaces with greater accuracy than computer 186 could do if it scanned the fitting surfaces 152 surfaces directly.

Computer 186 is programmed to derive the center of each of the spherical surface portions 176, 178, 180 on each of the alignment posts from the coordinates of each point on spherical surface portions 176, 178, 180 that it previously stored. Each of the datum points in the point cloud dataset that were scanned from the surface of the alignment posts (including spherical surface portions 176, 178, 180) have an associated position error. Due to this error, directly scanning the cylindrical and frusto-conical surfaces of fittings 152 may not be sufficiently accurate to determine the orientation and position of the mating surfaces of the fittings 152 to which anchors 104 are coupled (in the metal duplicate of wax-up framework 150). To reduce this error, alignment posts 156 are provided with the spherical surface portions 176, 178, 180 which have larger surface areas than the mating surfaces of fittings 152 to which they are coupled. These spherical surface portions 176, 178, 180 have known predetermined geometrical shapes and orientations with respect to the fittings 152. These shapes and orientations are programmed into computer 186, which employs algorithms incorporating this predetermined geometry to derive a more accurate position and orientation for the mating surfaces of fittings 152.

In particular, computer 186 is programmed with the diameter (or radius) of each of the spherical surfaces 176, 178, 180 as well as the distances between the centers of the spherical surfaces 176, 178, 180 and the fittings 152, as well as the particular shape and orientation of the frusto-conical and cylindrical surfaces of the fittings 152 themselves. Computer 186 is configured to fit the set of data points for each spherical surface 176, 178, 180 of alignment posts 156 to an ideal sphere having the same diameter (or radius). It is therefore configured with the geometric parameters (in this case the diameter) of geometric surfaces (spherical surface portions 176, 178, 180) on alignment posts 156 and applies these parameters to points gathered from a scan of the geometric surfaces to derive other geometric parameters (in this case the center of spherical surface portions 176, 178, 180). In the preferred embodiment, the technician uses the digitizer to select data points by selecting regions on the screen that show portions of the point cloud dataset having the predetermined geometry. Once selected, the technician signals the computer to calculate the parameters of a predetermined geometry that best fits the selected data points of the point cloud dataset. The computer 186, in turn sequentially fits a surface of the predetermined geometry to the selected data points until it determines the parameter of a geometry having a best fit to the data points. In the preferred example, the computer 186 fits the data points to a sequence of spheres having different diameters and center locations until it finds a diameter and center point of a sphere that fits the data points best. The computer 186 then saves the center point of this sphere for later use in determining the location of the surfaces of the fittings in the manner described below.

In a preferred embodiment, computer 186 is configured to find the center of the spherical surface portions by using an algorithm incorporating error minimizing mathematical methods. In the example given here, computer 186 is configured to calculate the root mean square (RMS) error of all the data points scanned from the spherical surface portions 176, 178, 180 (and selected by the technician) with respect to the closest data points on the surface of the ideal sphere and vary the diameter and center of the ideal sphere to minimize this error until computer 186 determines a center having the smallest RMS error. The results of this calculation are coordinates for the center of the sphere that is closest to the centers of the spherical surface portion.

Computer 186 is configured to repeat this process of fitting data points of a spherical surface portion to an ideal sphere having the same diameter for data points scanned from each spherical surface portion. In this manner, computer 186 derives the coordinates of the centers of each of the spherical surface portion 176, 178, 180 for all of the alignment posts 156.

In its digital memory, computer 186 stores the geometry of each of the alignment posts 156 and the position and orientation of alignment posts 156 with respect to fittings 152 when they are coupled together. In particular, computer 186 stores the distance between the spherical surface portions 176, 178, 180 of the alignment posts 156 and the distances between these centers and the mating surfaces of fittings 152. Once computer 186 calculates the centers of spherical surface portions 176, 178, 180 using the method above, and since spherical surface portions 176, 178, 180 are aligned on the longitudinal axis of the alignment posts 156, computer 186 can easily calculate the location and orientation of fittings 152 linearly interpolating between the previously calculated centers of spherical surface portions 176, 178, 180. By combining this geometric distance information with the previously determined centers of each of the spherical surface portions, computer 186 can determine the precise location and angular orientation of fittings 152, particularly, the cylindrical and frusto-conical surfaces on the fitting 152 to which the posts 156 having those centers are fixed. It is these surfaces on fittings 152 (in the metal duplicate of wax/acrylic framework 150) to which mating surfaces 108 of anchors 104 are mounted.

In this manner, even though the mating surfaces of fittings 152 are hidden by the alignment posts 156 during scanning, computer 186 is able to determine their precise location and orientation using stored data indicating parameters of the predetermined geometric shapes (diameter/radius of the spherical surface portions 176, 178, 180, distance from the centers to the fittings 152, and shape of the mounting surfaces on the fittings, etc.) comprising alignment posts 156 and their predetermined relationship to fittings 152 when properly attached to the fittings. In this manner, a scanner can determine with much greater accuracy the shape, position, and orientation of surfaces that it could not determine directly by scanning those surfaces.

One reason this method is an improvement is due to the difference in surface area between the mating surfaces on fittings 152 as compared to the spherical surface portions 176, 178, 180 of alignment pins 156. The mating surfaces 160, 162, 164 on fittings 152 are relatively small and difficult to scan.

While it is possible to scan the mating surfaces of fittings 152 (e.g. the surfaces to which anchors 104 will be fixed), nonetheless due to their small size any position measurements taken using current technology would not give the accuracy of position and orientation required to insure a precise fit between the denture and the anchors. The supplemental or extension surfaces on the alignment posts 156 (e.g. spherical surface portions 176, 178, 180) are much larger and thus can be scanned to generate many more data points (i.e. data scanned on the spherical surface portions 176, 178, 180) that, combined with knowledge of supplemental surfaces geometry, provides more data points and permits a more accurate determination of the location of fittings 152 thereby effectively increasing the accuracy of the derived datum point, in particular the radius (or diameter) and the center point of the spherical surface portion.

At this step in the process, computer 186 has determined the longitudinal axes of each of the alignment pins 156 and hence the longitudinal axes of each of fittings 152. Computer 186 has also determined the location along each of the longitudinal axes where the fitting 152 associated with the axis is located. This calculated axial orientation and position information comprise a vector that defines the location and angular orientation of the mating surfaces of each fitting 152.

In the next step of the process, step 204 (FIG. 20), computer 186 is configured to remove the alignment posts 156 from the set of surface data points of the assembly 196—i.e. the point cloud dataset created from the coordinate data scanned from the surface of assembly 196 by scanner 182. The reduced dataset produced by the operation is shown schematically in FIG. 21.

Figure 21:
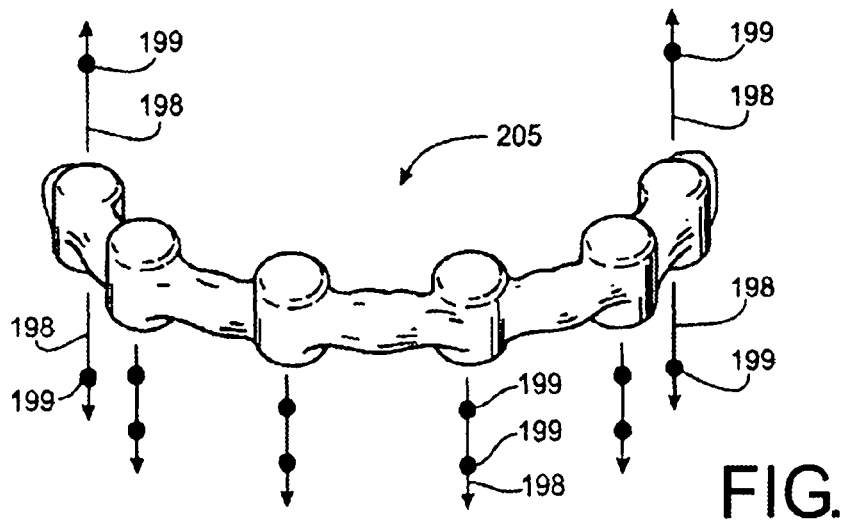
FIG. 21 is a graphical representation of the surface model scanned from the wax-up framework plus alignment post assembly of FIGS. 14 and 19 with the alignment posts subsequently digitally removed.

In FIG. 21 the point cloud dataset 205 (i.e. the preliminary surface model of the wax-up framework 150) is shown with alignment posts 156 removed and replaced symbolically with vectors 198 and circle center points 199. The eight vectors 198 represent the longitudinal axes of alignment pins 156 and fittings 152. The circle centers 199 represent the centers of the spherical surface portions 176, 178, 180 of alignment pins 156 derived as described above. The data points scanned from the surface of the alignment pins 156 are not shown in FIG. 21, but have been removed by computer 186.

In the next step of the process, step 206, computer 186 further modifies the surface model 205 of the framework by combining the remaining portion of the point cloud dataset (i.e. with the alignment pins removed) with a surface model of flat surfaces or pads 207 defining an exposed surface of each fitting 152. These parameterized flat surfaces or pads are stored in a digital electronic memory of the computer 186. This process is preferably done by Boolean union.

Figure 22:
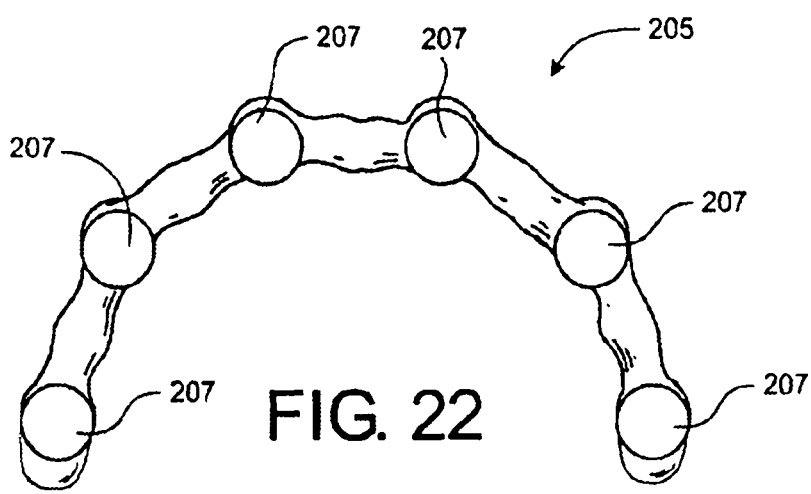
FIG. 22 is a graphical representation of the surface model of FIG. 21 with pads.

These flat surfaces or pads represent the surface of the fittings that face the patient's mucosal tissue. Computer 186 previously determined the orientation and location of each of the fittings 152 (and thus pads 207) based upon the computer's calculation of the center points of the spherical surface portions of posts 156. Computer 186 also stores a parametric representation of the shape, location and orientation of the surfaces of each fitting 152. In the preferred embodiment, computer 186 stores numerical models of fittings that the user selects and inserts into the surface model of wax-up framework 150. FIG. 22 shows the surface model 205 of FIG. 21 after computer 186 has modified it with the addition of pads 207.

Figure 23:
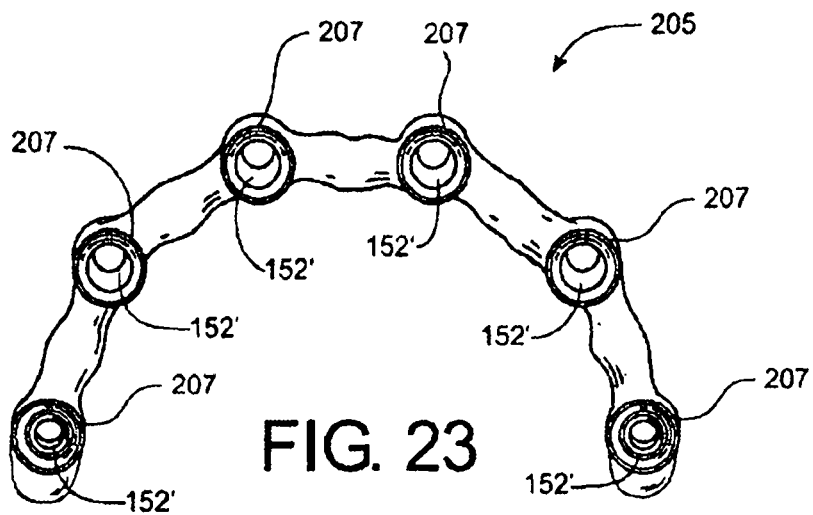
FIG. 23 is a graphical representation of the surface model of FIG. 22 with parameterized fitting sunk into the pads configured to be mounted to the anchors.

In the next step in the process, step 208 (FIG. 20), computer 186 is configured to insert fitting surfaces—particularly the surfaces of the fittings that mate with mating surfaces 108 of anchors 104. The computer 186 has determined the orientation and location of each fitting 152 (step 202) to determine the location of the fitting. Digital parameterized fittings 152' are digital models of the mating surfaces of actual fittings 152 that are configured to engage anchors 104 or surmounted abutments. These digital parameterized fittings are stored in a digital electronic memory of the computer 186. In the preferred embodiment, the computer 186 performs a Boolean subtraction thereby combining the appropriate selected digital parameterized fittings 152' with the surface model 205 to insert the mating surfaces of the fitting into the surface model. In the illustrated embodiment this removes portions of the surface model 205 underneath the surface of pads 207 to the appropriate depth, leaving the sunken mounting surfaces surrounded by a surrounding portion of pads 207. The surface model 205 as it exists before the Boolean subtraction is shown in FIG. 22. The surface model 205 after the Boolean subtraction and insertion of the mounting surfaces of fittings 152' is shown in FIG. 23

In the next step of the process, step 210, computer 186 calculates the tool paths for manufacturing the actual dental framework from the surface model 205. There are a variety of processes by which the actual denture framework can be manufactured and hence a variety of tool paths that can be generated. For example, the calculated tool paths can describe the path of a single or multiaxis CNC cutting tool such as a multi-axis milling machine, the path of an EDM electrode, or the path of a material deposition device such as stereolithography, rapid prototyping, 3D printing, or laser sintering machines. Even further, the tool path may comprise several tool paths for different machines and processes that are performed in succession to manufacture the denture framework from surface model 205. Even further, the tool path can define the path of a tool used to manufacture a mold in which the denture framework (or a precursor thereto) is cast.

In the final step in the process, step 212, the tool path is used to manufacture the denture framework. Typically the tool path is loaded in digital form into a computer numeric controlled (CNC) machine that drives a tool such as a material removal tool to remove excess material or a material deposition tool to build up material. The framework may be machined in a single process or in a series of processes on several machines. In the preferred embodiment, the denture framework is preferably manufactured by a multiaxis computer numeric controlled (CNC) milling machine. In an alternative process, the bridging structures 154 of the framework 150 are manufactured from the surface model 205 using one process, such as a milling machine, and recessed portions, such as the mounting (mating) surfaces of the fittings 152, are manufactured using another process, such as wire electrodischarge machining (EDM) or plunge EDM. In another alternative process, the milling machine, stereolithography, rapid prototyping, 3D printing, or laser sintering machines or EDM can be used to manufacture the mold in which the denture framework (or a precursor thereto) is cast.

The framework is preferably manufactured from titanium, zirconia, alumina, or other ceramic material having mechanical strength characteristics similar to titanium. If it is a ceramic material, the material can be machined in its fully sintered state or in a partially green or fully green state in which the ceramic material is only partially sintered, or has not been sintered at all. A ceramic (e.g. zirconia) may be cast in a mold that has been machined using the surface model and then sintered to form the final part. Alternatively, the ceramic may be cast in a mold that only approximates the shape of the final framework indicated by the surface model and then subsequently machined to the final dimensions using machining tools employing tool paths generated from the surface model.

Once the final framework has been made, it is returned to the dentist together with the stone cast 125 and the wax-up framework 150. The dentist then verifies the accurate manufacture of the final framework and then follows his traditional procedures in manufacturing a denture from the final framework.

One of the reasons this process above is recommended is because of the unfamiliarity of dentists with the technology and the need to, at least initially, permit them to have the greatest degree of control in the denture manufacturing process. As they become more comfortable with the process, however, the dentist can dispense with additional dentist-performed steps, such as the creation of the stone cast, the putty index, and the wax-up framework can be dispensed with by scanning the dentist's handiwork earlier in the process. This is beneficial because it reduces the possibility of error and inaccuracies by eliminating several of the replication steps. In the process proposed above, the dentist would first make a negative replica of the mandible (or the maxilla) with an impression. The dentist would then use the impression to make a positive replica of the mandible (or the maxilla) with a stone cast. The dentist then uses the stone cast to define the mating surface locations of the framework, and then the wax-up framework itself is scanned. Each of these transfer steps generates a small amount of error, which can be eliminated once dentists are comfortable with the accuracy of the final framework that is manufactured using the scanning technology.

In a first alternative process for manufacturing the final framework, the dentist will manufacture the stone cast 125 as described above, but will not manufacture the framework, leaving the design and manufacture of the framework to the laboratory. This first alternative process is shown in FIG. 24.

The first steps of this alternative process are performed exactly as they are in the process described above: the dentist places anchors in the patient's mouth, waits for them to heal, takes an impression of the patient's mouth, and makes a stone cast from that impression. Once the stone cast has been created, however, the dentist does not manufacture the wax-up framework. Instead, the dentist sends the stone cast directly to the laboratory and the laboratory scans the stone cast, then designs and manufactures the final framework from the stone cast. In the discussion of this process below, the stone cast is referred to as stone cast 125 since it is made in exactly the same manner as the stone cast 125 in the example above: it is configured to receive a framework having six fittings that include two fittings 152A, 152B with through holes and four fittings 152C, 152D, 152E, 152F without through holes.

Figure 24:
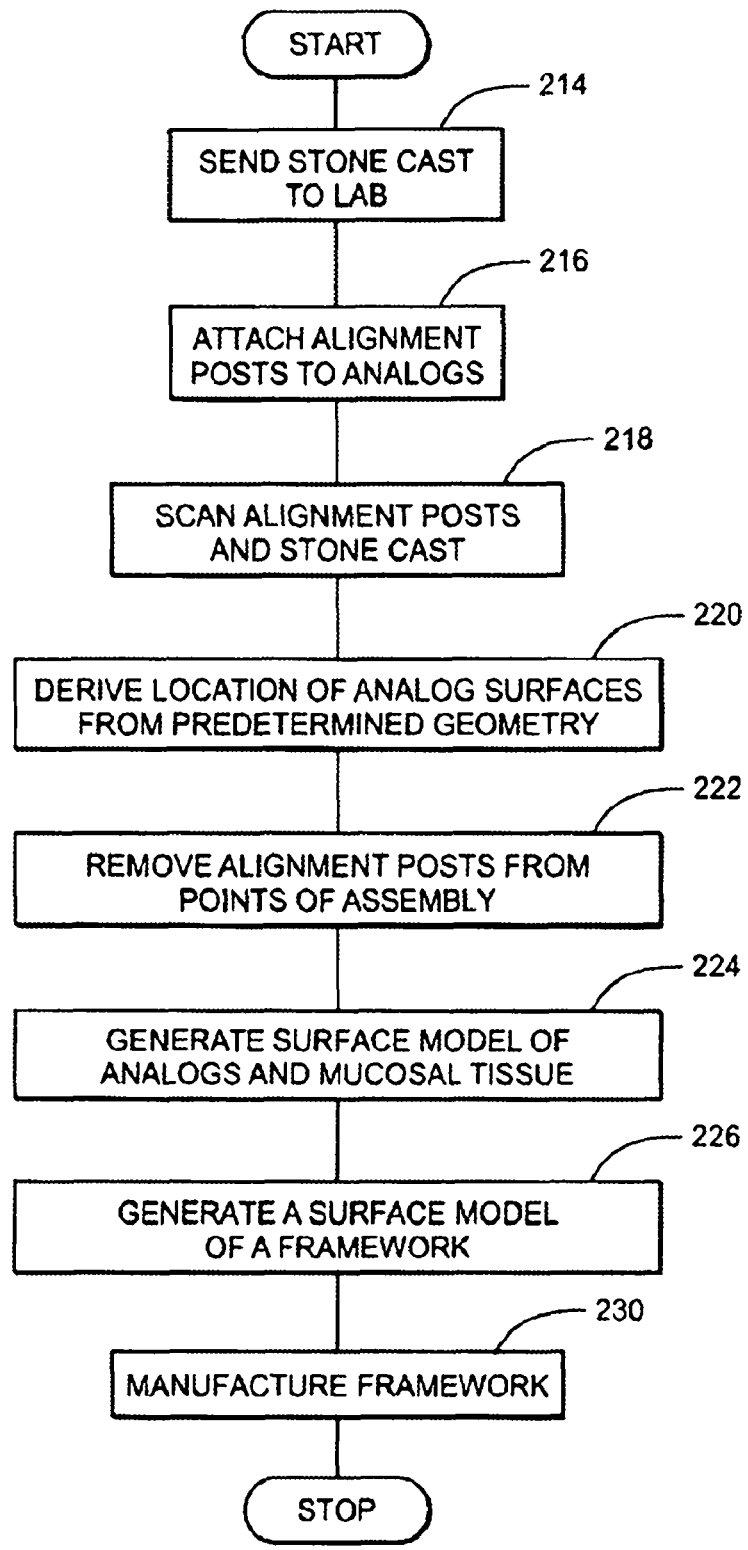
FIG. 24 is a flow chart of the process of manufacturing a denture framework from a scan of the stone cast shown in FIGS. 8-13B but with alignment posts attached to it—and optionally a scan of the diagnostic wax-up and/or the putty index of FIGS. 9-12B.

This first alternative process is shown in FIG. 24. In step 214 of the first alternative process, the dentist sends the stone cast 125 to the laboratory. The dentist may also send a diagnostic wax-up 130 or putty index 142 of the denture.

In step 216, the laboratory inserts six alignment posts 156 into the analogs 124 embedded in the stone cast 125. These alignment posts 156 are the same as the alignment posts shown in FIGS. 14-18 with one difference: their mating surfaces are configured to engage the mating surfaces of analogs 124 and hold the alignment posts coaxial with the longitudinal axis of analogs 124. They may have differently shaped flat, frusto-conical and cylindrical surfaces configured to engage with the mating surfaces of analogs 124 instead of the fittings 152. As in the case of alignment posts 156 described above in the first process, the alignment posts 156 used in this first alternative process have two spherical surfaces comprising centers coaxial with coping 110. Since they are mounted to analogs 124 on the stone cast, all six of the alignment posts 156 mounted on stone cast 125 are of the style identified above as 156C-F, comprising a single post portion having two spherical surface portions. As in the first process described above, these fittings need not have a spherical surface portions, but may have any predetermined geometric shape. Further, and as described above, the alignment posts 156 can be dispensed with in this step of the first alternative process and the analog surfaces can be scanned directly by scanner 182 if scanner 182 is of sufficient accuracy that it can scan and determine the position and orientation of the mounting surfaces of analogs 124 without the need of attaching a supplemental surface to those mounting surfaces, such as the alignment posts 156.

The shape and orientation of the mounting surfaces on the alignment posts 156 in this alternative process are not configured to engage mating surfaces on fittings 152 in the wax-up framework 150, but are configured to engage with exposed mating surfaces on the analogs 124 in the stone cast 125. As in the case of the alignment posts 156 attached to fittings 152, the mating surfaces on the alignment posts and the mating surfaces on the analogs 124 interengage to cause the alignment posts 156 to be aligned coaxial with analogs 124. The alignment posts 156 cover the free ends of the analogs 124.

In step 218, once the alignment posts 156 have been attached to the analogs 124, the scanner 182 is configured to scan the alignment posts and the soft tissue replica of the patient's mouth formed in the surface of the stone cast 125, and the alignment posts 156. This scanning is done in the same manner as described above in conjunction with FIG. 20. The surfaces of stone cast 125 that are scanned by scanner 182 include the surfaces of the stone cast that replicate the mucosal tissue in the patient's mouth. Scanner 182 stores in the memory of computer 186 a first point cloud dataset of the stone cast 125 with alignment posts 156 attached. In step 218, scanner 182 also scans the surface of diagnostic wax-up 130 and the surface of stone cast 125 (preferably when they are assembled) and saves a second point cloud dataset collectively representing the scanned surface of the diagnostic wax-up 130 and stone cast 125. Alternatively, the operator can scan the diagnostic wax-up 130 separately from the stone cast and later register the point cloud dataset of the stone cast 125 and the diagnostic wax-up 130. As a further alternative, instead of scanning the diagnostic wax-up 130 scanner 182 can scan the putty index 142.

When the diagnostic wax-up 130 is scanned, it can be scanned either in its proper position on the stone cast 125, or it can be scanned separately.

If it is scanned on the stone cast 125, the scan preferably includes data points taken from all the exposed external surfaces of the diagnostic wax-up 130 (i.e. the outwardly facing surfaces that model the gum and the teeth) as well as surfaces of the stone cast 125 adjacent to the diagnostic wax-up 130. The surfaces of the stone cast 125 adjacent to the diagnostic wax-up that are scanned in the second point cloud dataset are also preferably scanned in the first point cloud dataset and thus there is some overlap in surface contours in both the first and the second point cloud datasets—both datasets include data points scanned from the same surfaces of stone cast 125. This permits later registration of the first and second point cloud datasets.

If the diagnostic wax-up 130 is scanned when it is separate from the stone cast 125, it is preferably scanned so that the second point cloud dataset includes data points taken from all the exposed external surfaces of the diagnostic wax-up 130 (i.e. the outwardly facing surfaces that model the gum and the teeth) as well as surfaces of the diagnostic wax-up 130 that would abut stone cast 125 if the diagnostic wax-up 130 was mounted on the stone cast. Since the diagnostic wax-up 130 was formed by molding a plastic material to the surface of the stone cast 125, the scanned surface contour of the diagnostic wax-up 130 that abut the stone cast are a mirror image of surface contours of the stone cast 125.

In the preferred embodiment these abutting stone cast 125 surfaces were scanned previously and are a part of the first point cloud dataset. Thus, the first and second point cloud datasets include a subset of data points taken from mirror image surface contours—surface contours common to both the first and second point cloud datasets—common to the diagnostic wax-up 130 and to the stone cast 125. This permits later registration of the first and second point cloud datasets.

In a further alternative, the putty index 142 may be scanned instead of the diagnostic wax-up 130. When the putty index 142 is scanned, it can be scanned either in its proper position on the stone cast 125, or it can be scanned separately.

If the putty index 142 is scanned while on the stone cast 125, the scan preferably includes data points taken from all the exposed external surfaces of the putty index 142 (i.e. the inwardly facing surfaces of the putty index that were molded to the outwardly facing surfaces of the diagnostic wax-up 130 (i.e. the facial aspect, including the outwardly facing teeth 132 and gum 134 of the diagnostic wax-up 130) as well as surfaces of the stone cast 125 adjacent to the putty index 142 when it is fitted on the stone cast 125. The surfaces of the stone cast 125 adjacent to the putty index 142 that are scanned in the second point cloud dataset are also preferably scanned in the first point cloud dataset and thus there is some overlap in surface contours in both the first and the second point cloud datasets—both datasets include data points scanned from the same surfaces of stone cast 125. This permits later registration of the first and second point cloud datasets.

If the putty index 142 is scanned when it is separate from the stone cast 125, it is preferably scanned so that the second point cloud dataset includes data points taken from all the exposed external surfaces of the diagnostic wax-up 130 (i.e. the outwardly facing surfaces that model the gum and the teeth) as well as surfaces of the putty index 142 that abut stone cast 125 when the putty index 142 is mounted on the stone cast. Since the putty index 142 was formed by molding a plastic material to the surface of the stone cast 125 and to the facial aspect of the diagnostic wax-up 130, the scanned surface contour of the putty index 142 that abut the stone cast are a mirror image of surface contours of the stone cast 125.

In the preferred embodiment, these abutting stone cast 125 surfaces were scanned previously and are a part of the first point cloud dataset. Thus, the first and second point cloud datasets include a subset of data points taken from mirror image surface contours—surface contours common to both the first and second point cloud datasets—common to the putty index 142 and to the stone cast 125. This permits later registration of the first and second point cloud datasets.

In step 220, computer 186 is configured to derive the location and orientation of the mating surfaces of the analogs from the predetermined geometry of the alignment posts 156, in the same manner as it determined the location and orientation of the mating surfaces of the fittings in step 202 (FIG. 20).

In step 222, computer 186 is configured to remove the data points corresponding to the alignment posts from the first point cloud dataset in the same manner as it removed the alignment posts in step 204.

In step 224, computer 186 is configured to generate a first surface model of the stone cast 125 from the first point cloud dataset. This surface model includes the analogs as they would appear uncovered, with alignment posts 156 removed, and the surface of stone cast 125 that replicates the patient's mucosal tissue. The first surface model includes the mating surfaces of the analogs 110, which represent the anchors 104 in the patient's mouth. Further in step 224, computer 186 generates a second surface model of diagnostic wax-up 130 (or alternatively putty index 142) from the second point cloud dataset.

The first surface model and the second surface model include surface contours that are common to both the first and second point cloud datasets: they include data points in each model that were scanned from a common surface, preferably a portion of stone cast 125 that was scanned into both the first and the second point cloud datasets, or they include data points of abutting surfaces in the first and second point cloud datasets.

In step 226, computer 186 is configured to generate a surface model of a dental framework 228 (FIGS. 25-27) from the first surface model of the stone cast 125 that was generated in step 224. Computer 186 is first configured to generate the fittings of the dental framework, in particular, the surfaces of the fittings in the final framework that mate with mating surfaces 108 of anchors 104. The computer 186 refers to an internal library of digital parameterized fittings 152" which define in parametric form the location and orientation of the mounting surfaces of the actual fittings. The digital parameterized fittings 152" are digital models of the surfaces of the actual fittings that are configured to engage anchors 104. These digital parameterized fittings can be pre-designed, modified by the user, derived from existing alignment post CAD geometries, or free form designed. These digital parameterized fittings 152" are stored in a digital electronic memory of the computer 186.

Computer 186 electronically stored at least one and preferably a plurality of different digital parameterized fittings 152" (shown in FIGS. 25, 26, 27 as items 152"A, 152"B, 152"C, 152"D, 152"E, and 152"F) in its internal library between which it can select. These digital parameterized fitting 152" have surfaces that are configured to mate with the analog 124 surfaces in the first surface model of the stone cast 125 that were derived in step 220.

In step 220, above, computer 186 determined the location and orientation of the six analogs 124 in the stone cast 125 in the first point cloud dataset of the first alternative process. Computer 186 sequentially selects a digital parameterized fitting 152" from its internal library for each of the analogs and aligns the mating surface (or surfaces) and axis of the selected digital parameterized fitting 152" with the surface (or surfaces) and axis of one of the analogs whose location and orientation it determined in step 220. Computer 186 repeats this process for each of the six analogs 124 whose location and orientation were determined in step 220, until it has built up a surface model of dental framework 228 comprising the six digital parameterized fittings 152" (shown in FIGS. 25-27 as items 152"A, 152"B, 152"C, 152"D, 152"E and 152"F).

As in the case of the digital parameterized fittings 152' in FIG. 20, these fittings are configured to engage mating surfaces 108 of anchors 104. The digital parameterized fittings 152" mathematically represent the structures that will be coupled to the anchors 104 in the final denture framework that is mounted in the patient's mouth.

Figure 25:
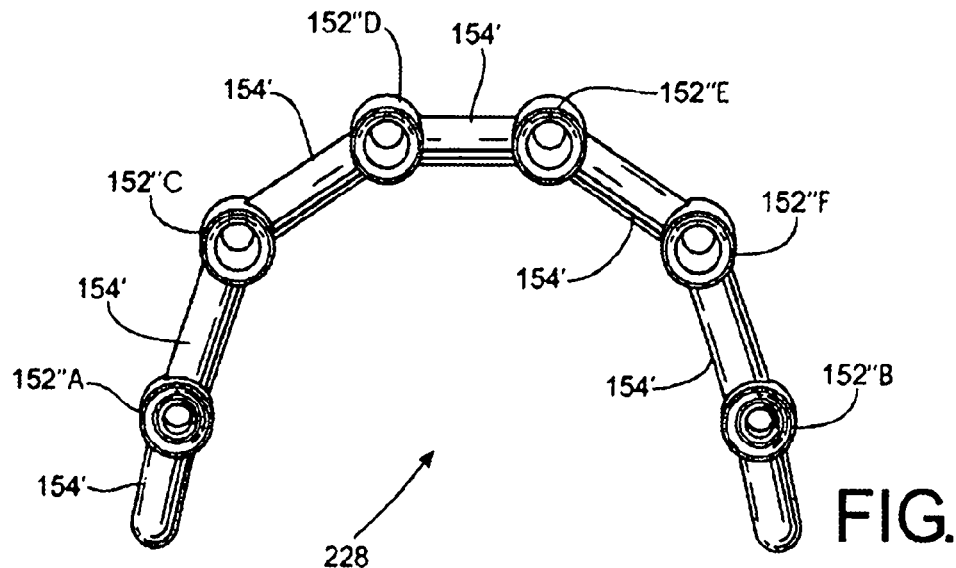
FIGS. 25-27 are three different perspective views of a mathematical surface model of a denture framework generated by the scanner of FIG. 19.
Figure 26:
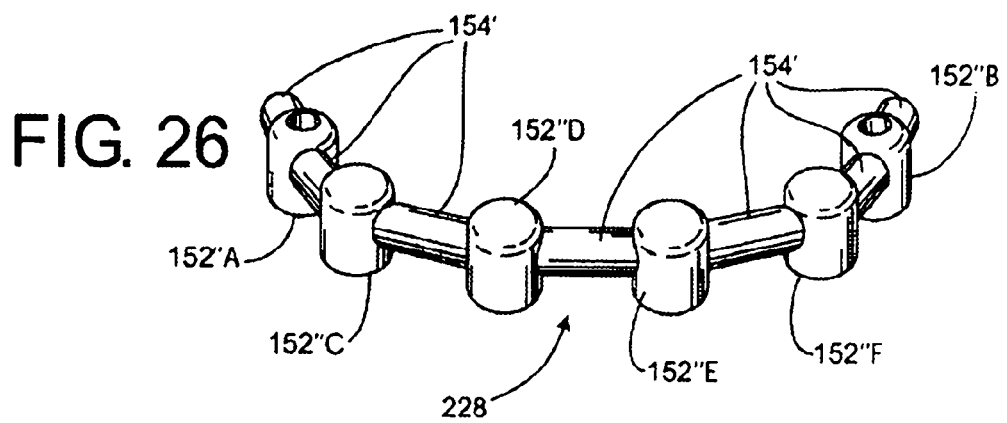
Figure 27:
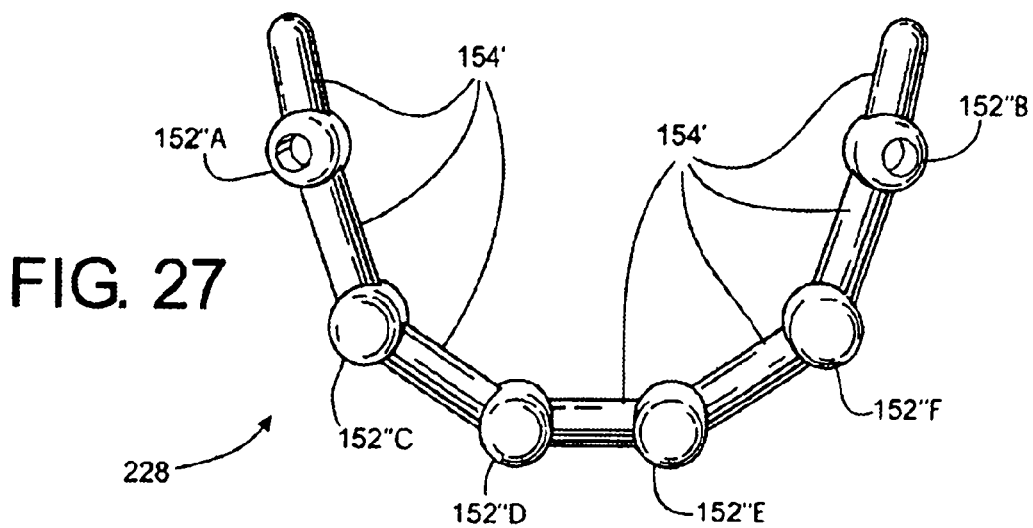

Further in step 226, the computer 186 is configured to generate a surface model of bridging structure 154' (FIGS. 25-27) that will join the six digital parameterized fittings 152". This includes the computer 186 determining the cross-sectional shape, length and location of the bridging structures as described below. This surface model of this bridging structure 154' extends between and joins the six digital parameterized fittings 152" and thereby completes the surface model of the dental framework 228. Bridging structure 154' also comprises the portions 155 that extend away from the end digital parameterized fittings 152"A and 152"B and are supported only at one end. One form of the bridging structure is shown in FIGS. 25-27 as a simple elongated member having a predetermined cross section.

To generate bridging structure 154', computer 186 determines the shape, length, and location of the individual portions of the bridging structure between each of adjacent digital parameterized fittings 152". It is further configured to determine the shape length and location such that the individual portions will not intersect the first surface model (i.e. the surface model of the stone cast 125 provided in step 222). Since the surface of the stone cast represents the exposed surfaces (including mucosal tissue) in the patient's mouth, this reduces the likelihood that the physical framework created from the surface model will contact and damage the patient's mucosal tissue. Computer 186 is configured to provide a separation distance between the surface model of the stone cast and the bridging structures. In one arrangement the computer 186 is configured to place the bridging structures a predetermined minimum distance from the surface model of the stone cast. In another arrangement the computer is configured to permit the operator to select a desired minimum distance between the bridging structure and the surface model of the stone cast. In another arrangement, the computer is configured to offer to and/or accept from the operator only a certain range or number of minimum separation distances, such minimum separation distances preferably ranging between 1 mm and 5 mm.

Computer 186 is configured to create the bridging structure extending from or between each of the digital parameterized fittings by providing a pre-designed list of bridging structure forms (e.g., pontic form, abutment/tooth form, bar form wherein the bar form is e.g. a cylinder, circle, ellipse, square, polygon or other geometric shape) that have been previously stored in the electronic memory of the computer. In one configuration, the computer is configured to automatically select the cross sectional dimensions of each form (diameter, radius, major and minor diameter, height, width, etc.). In another configuration the computer is configured to present the user with a list of pre-set values or defined by the user among which the user can select preferred dimensions. In yet another configuration, the computer is configured to prompt the user to enter specific numeric values for these dimensions. The form of the bridging structures can also be defined by the user.

Computer 186 is configured to determine the proper location of the bridging structure 154' extending from each of the digital parameterized fittings 152" by locating the beginning and end of each structure according to position information for the fitting that is derived from the scanned point cloud dataset.

In another arrangement, the computer 186 is configured to determine the location of the bridging structure 154' extending from each of the digital parameterized fittings 152" by locating the beginning and end of each structure according to reference points and axes assigned to the digital parameterized fittings 152" by the computer program from a list of pre-set values or defined by the user. For example, each digital parameterized fitting which is placed in the model may have only certain types of bridging structures to which it can be connected, and may only connect to those bridging structures at certain locations one the digital parameterized fitting. This information. Is stored in the electronic memory of computer 186 in association with each digital parameterized fitting. When a particular fitting is inserted into the model, computer 186 is configured to the type and location information associated with the inserted fitting and locate (or permit the operator to locate) bridging structures of the type and at the locations compatible with those digital parameterized fittings. In another arrangement computer 186 is configured to locate the bridging structure 154' (e.g., pontic form, abutment/tooth form, bar form) between each of the digital parameterized fittings 152" by locating the beginning and end of each structure according to free form features selected by the user between each of the digital parameterized fittings 152".

In the case of distal extensions 155, computer 186 is configured to cantilever them off the digital parameterized fittings 152" and extend them distally along the arch of the patient's mouth. These distal extensions 155 are preferably 20 mm in overall length or less. They are also selected as described above.

Computer 186 is configured to conduct a mechanical design analysis of the distal extensions 155 that validates shear and bending strength limits for those geometries relative to their chosen material and shapes. Computer 186 is configured to apply the appropriate shear, tensile and compressive stress analysis techniques to the chosen geometries automatically or from a pre-determined list of tests chosen by the user. Upon successful analysis of the distal extension designs, the extensions are verified or accepted by the user.

As part of the step of generating the bridging structure 154' computer 186 is configured to determine a location for the bridging structure 154' that will not intersect the second surface model (i.e. the surface model of diagnostic wax-up 130). This insures that the bridging structure 154' of the final denture framework will not stick through, but will be disposed within, the body of the denture. Computer 186 first aligns or registers the first point cloud dataset (representing the stone cast 125 surfaces) with respect to the second point cloud dataset (representing the diagnostic wax-up 130 surfaces), thereby mathematically determining the three-dimensional volume defined by the diagnostic wax-up 130. This volume defined by the intersection of these two datasets is the volume of the denture as the dentist has designed it.

To align or register these two volumes, computer 186 is configured to identify the overlapping portions common to both the first and second point cloud datasets, i.e. the portions of both datasets that have the same (i.e. matching) surface contours. A preferred program for performing these functions is Raindrop Geomagic Studio Suite (by Geomagic of Research Triangle Park, N.C., USA).

In the first instance, the stone cast 125 is scanned to generate the first point cloud dataset, and the diagnostic wax-up 130 is mounted on the stone cast 125 and both are scanned to create the second point cloud dataset. The overlapping portions of the two point cloud datasets comprise the data points of the stone cast 125 for surfaces of the stone cast 125 that were scanned in both the first point cloud dataset and the second point cloud dataset.

In the second instance, the stone cast 125 is scanned to generate the first point cloud dataset and the diagnostic wax-up 130 is not mounted on the stone cast 125 but is scanned separately to create the second point cloud dataset. The overlapping portions of the two point cloud datasets comprise the surface of the stone cast 125 that abuts the diagnostic wax-up 130 in the first point cloud dataset, and the surface of the diagnostic wax-up 130 that abuts stone cast 125 when it is mounted on the stone cast 125 in the second point cloud dataset. Since the two abutting portions were formed by pressing the diagnostic wax-up 130 material against the stone cast when soft, the two abutting surfaces have identical surface contours that can be matched one to the other, and in that sense overlap.

In the third instance, the stone cast 125 is scanned to generate the first point cloud dataset, and the putty index 142 is mounted on the stone cast 125 and both are scanned to create the second point cloud dataset. The overlapping portions of the two point cloud datasets comprise the data points of the stone cast 125 for surfaces of the stone cast 125 that were scanned in both the first point cloud dataset and the second point cloud dataset.

In the fourth instance, the stone cast 125 is scanned to generate the first point cloud dataset and the putty index 142 is not mounted on the stone cast 125 but is scanned separately to create the second point cloud dataset. The overlapping portions of the two point cloud datasets comprise the surface of the stone cast 125 that abuts the putty index 142 in the first point cloud dataset, and the surface of the putty index 142 that abuts stone cast 125 when it is mounted on the stone cast 125 in the second point cloud dataset. Since the two abutting portions of the stone cast 125 and the putty index 142 were formed by pressing the putty index 142 material against the stone cast 125 when soft, the two abutting surfaces have identical surface contours that can be matched one to the other, and in that sense overlap.

In the third and fourth instances (that use the putty index 142), the computer 186 locates the bridging structure 154' by locating the bridging structure behind the portion of the second point cloud dataset that was scanned from the inner surface of the putty index 142 that was formed by pressing it against the facial aspect of the diagnostic wax-up 130. This portion of the second point cloud dataset in the third and fourth instance has the same surface contours as the facial aspect of the diagnostic wax-up 130, which is a replica of the front of the body of the denture when made.

By locating the bridging structure 154' behind the inner surface of the putty index 142 in the second point cloud dataset, the computer insures that the surface model of the denture framework thus created will not protrude through the front of the denture body.

By locating the bridging structure 154' above the surface of the first point cloud dataset (i.e. stone cast 125) that represents the surface of the mucosal tissue the computer 186 insures that the surface model of the denture framework 228 thus created will not extend through the lower surface of the denture body and abut the mucosal tissues of the patient.

Computer 186 digitally assembles each of the short bridging sections of the bridging structure 154' and the digital parameterized fittings 152" into the surface model of denture framework 228. Computer 186 thereby generates the locations of the digital parameterized fittings 152", and the location of the bridging structures 154' coupling the digital parameterized fittings 152".

A graphic example of the surface model of the denture framework 228 generated by the computer in this manner can be seen in FIGS. 25-27, which illustrate a bottom view, front perspective view, and top view, respectively, of the surface model of the denture framework 228 and showing the digital parameterized fittings 152" and bridging structure 154'.

In the illustrated embodiment, each section of bridging structure 154' has a constant cross-sectional area (in this case a circular cross section) designed to minimize manufacturing time of the final framework. In an alternative embodiment, computer 186, when placing the bridging structure 154', is configured to customize the joints between the digital parameterized fittings 152" and the sections of bridging structure 154' by providing stress reduction factors such as radiused intersections between the digital parameterized fittings 152" and bridging structure 154'.

In the final step of this alternative process, step 230, the framework is manufactured in the same manner as described above in accordance with step 212.

Above were described two processes for manufacturing a dental framework. In the first process an impression 123, then a stone cast 125, then a wax-up framework 150 was made before anything was scanned. In the first alternative process an impression 123 and then a stone cast 125 was made before anything was scanned. This second process eliminated the need for creating a wax-up framework 150 and used a computer to generate the framework from an internal stored library of digital parameterized fittings 152". By eliminating additional replication steps, the possibility for error as well as the cost and time of manufacture is further reduced.

In a second alternative process for manufacturing a denture framework, the step of creating a stone cast 125 is eliminated and the impression 123 is used as the stone cast 125 was used in the first alternative process of FIGS. 24-27. The dentist may, of course, make a stone cast 125 on which to create his diagnostic wax-up 130, but the stone cast 125 in this second alternative process is not required for making a denture framework.

In the second alternative process, the dentist makes impression 123 as described in the first process and first alternative process (above) and sends it to the laboratory. The laboratory then mounts alignment posts 156 to the copings 110 located in the impression 123.

Scanner 182 is configured to scan the interior surface of the impression 123, which is a negative replica of the patient's mucosal tissues. This scan produces a first point cloud dataset that indicates the surface contours of the patient's mandibular mucosal tissues. The alignment posts 156 are coupled to the mating surfaces of the copings 110 embedded in the impression material.

The surfaces to which the alignment posts 156 are coupled are the surfaces that previously mated to the surfaces 108 of anchors 104. This second alternative process is substantially the same as the first alternative process. The dentist can optionally send a diagnostic wax-up 130 of the desired denture as well.

In the second alternative process, alignment posts 156 are attached to copings 110 embedded in impression 123. The impression 123 is a negative replica of the patient's mandible. The impression-plus-alignment-posts assembly is then fixed to jig 194.

Scanner 182 then scans the inside surface of impression 123 formed by the patient's mandible, which includes the patient's mucosal tissue and any existing dentition and edentulous areas. Scanner 182 also scans the surface of the alignment posts 156, which in this case are attached to the copings 110. The alignment posts are preferably as shown in FIG. 18, however the frusto-conical portions 173 and 175 may be configured differently to be fixed to the coping in a coaxial relationship in the same manner described above for the first process and the first alternative process.

Computer 186 is configured to save the three-dimensional data points of the interior surface of the impression formed by the patient's mandible and the alignment posts 156 as a point cloud dataset, to derive the location of the surfaces of copings 110 from the predetermine geometry, to remove the alignment posts 156 from the point cloud dataset of the impression-plus-alignment-posts assembly, to generate a surface model of the patient's mucosal tissue and the copings 110, and to generate a surface model of a dental framework 228 in the same manner described above in conjunction with the first alternative process.

In the final step of the second alternative process, the surface model of the framework 228 is manufactured as in step 212.

In a third alternative process, the surface model of a dental framework 228 can be generated from the diagnostic wax-up 130 itself.

Figure 28:
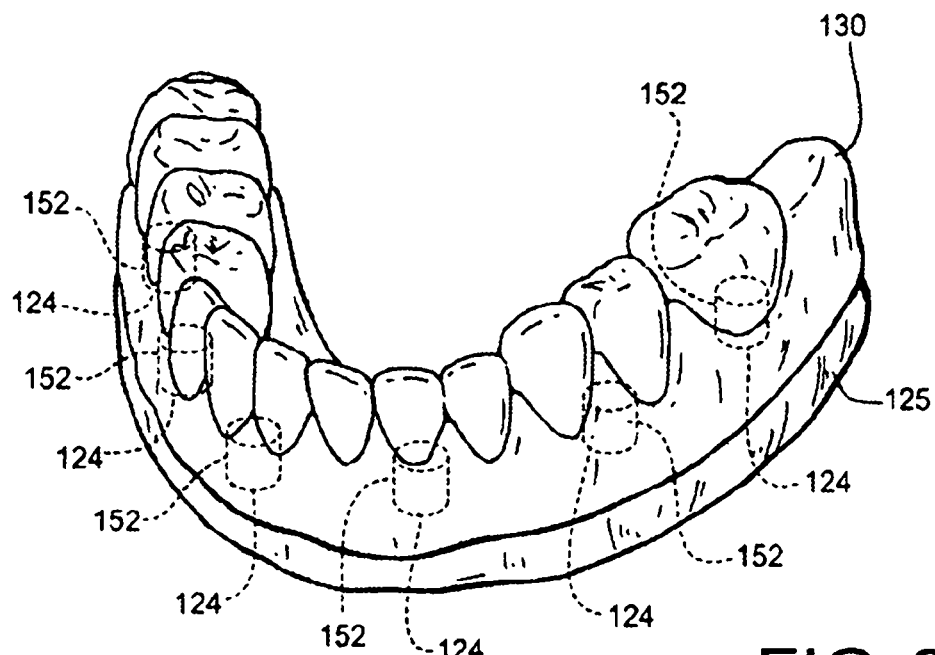
FIG. 28 is a perspective view of a diagnostic wax up formed on the surface of a stone cast with embedded fittings.
Figure 29:
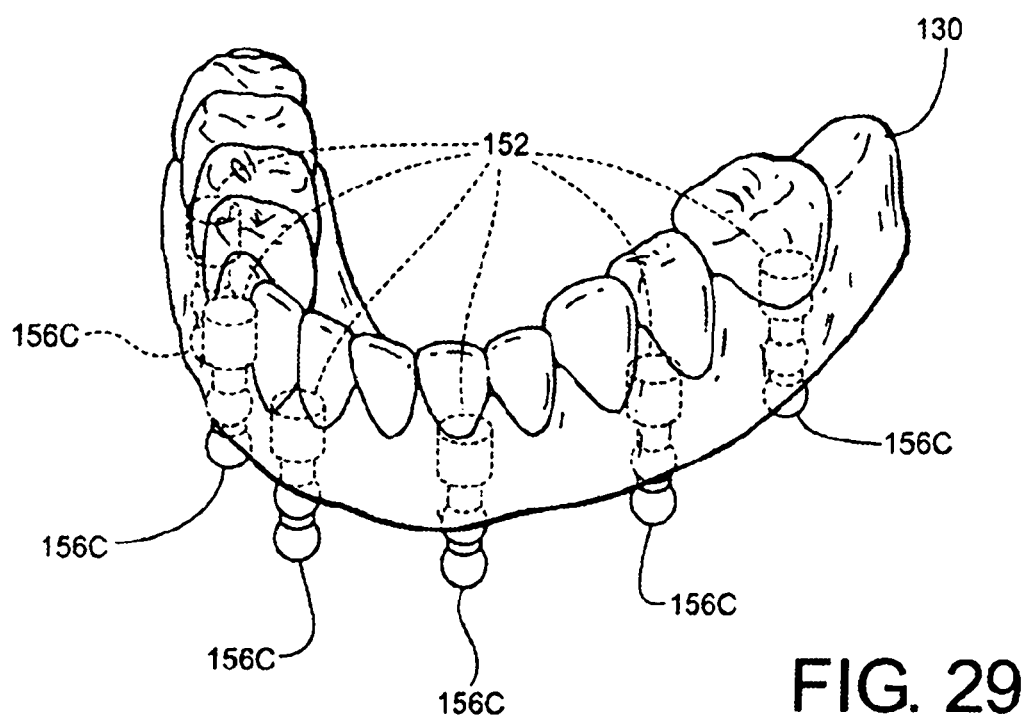
FIG. 29 is a perspective view of the wax-up of FIG. 28 removed from the stone cast with the fittings embedded in the diagnostic wax-up and alignment posts fixed to the now-free surfaces of the fittings.

In this process, shown in FIGS. 28-29, the dentist first mounts fittings 152 on the analogs 124 embedded in the stone cast 125 in the same manner as described in the above processes.

In the next step, the dentist forms the diagnostic wax-up 130 on the stone cast 125. The dentist molds the wax-up material to the surface of the stone cast 125 to capture the contours of the mucosal tissue as described above. The dentist also molds the wax-up material to the fittings 152, embedding the fittings 152 in the wax-up material.

The competed diagnostic wax-up 130 supported on the stone cast 125 with the fittings 152 embedded in the diagnostic wax-up 130 are shown in FIG. 28.

The dentist then removes the diagnostic wax-up 130 from the stone cast 125 and sends it to the laboratory.

Once at the laboratory, a technician fixes alignment posts 156 (preferably alignment posts 156C, D, E or F, since they extend from only one side of the fitting 152 to which they are coupled) to the now-exposed mating surfaces of the fittings 152. This arrangement is shown in FIG. 29.

The technician then mounts the assembly of diagnostic wax-up 130 with alignment posts 156 to scanner 182 and directs the scanner to scan the assembly in the same manner as described above for scanning wax-up framework 150 with alignment posts 156.

This scan produces a point cloud dataset representing the contours of the diagnostic wax-up 130 and the alignment posts 156.

As in the previous examples, the technician directs computer 186 to determine the location of the centers of the spherical surface portions of the point cloud dataset, and ultimately the location and orientation of the mating surfaces of the fittings 152.

Computer 186 then generates a surface model of a framework 228 that will be enclosed within the diagnostic wax-up 130. Computer 186 inserts digital parameterized fittings 152" into the surface model of a denture framework 228 that correspond to fittings 152. Computer 186 then inserts the bridging structure 154' and distal extensions 155 into the surface model of a denture framework 228.

To generate bridging structure 154', computer 186 determines the shortest distance between each of the adjacent digital parameterized fittings 152" that will not intersect the surface model of the diagnostic wax-up 130, but will be contained completely within the contours of the diagnostic wax-up 130. Computer 186 already has the surface contours of the diagnostic wax-up 130 because it already scanned the surface of the diagnostic wax-up 130 in the point cloud dataset. This insures that the actual bridging structure of the denture framework (created from the model of the bridging structure 154') will not protrude through, but will be disposed within, the body of the denture.

Figure 30:
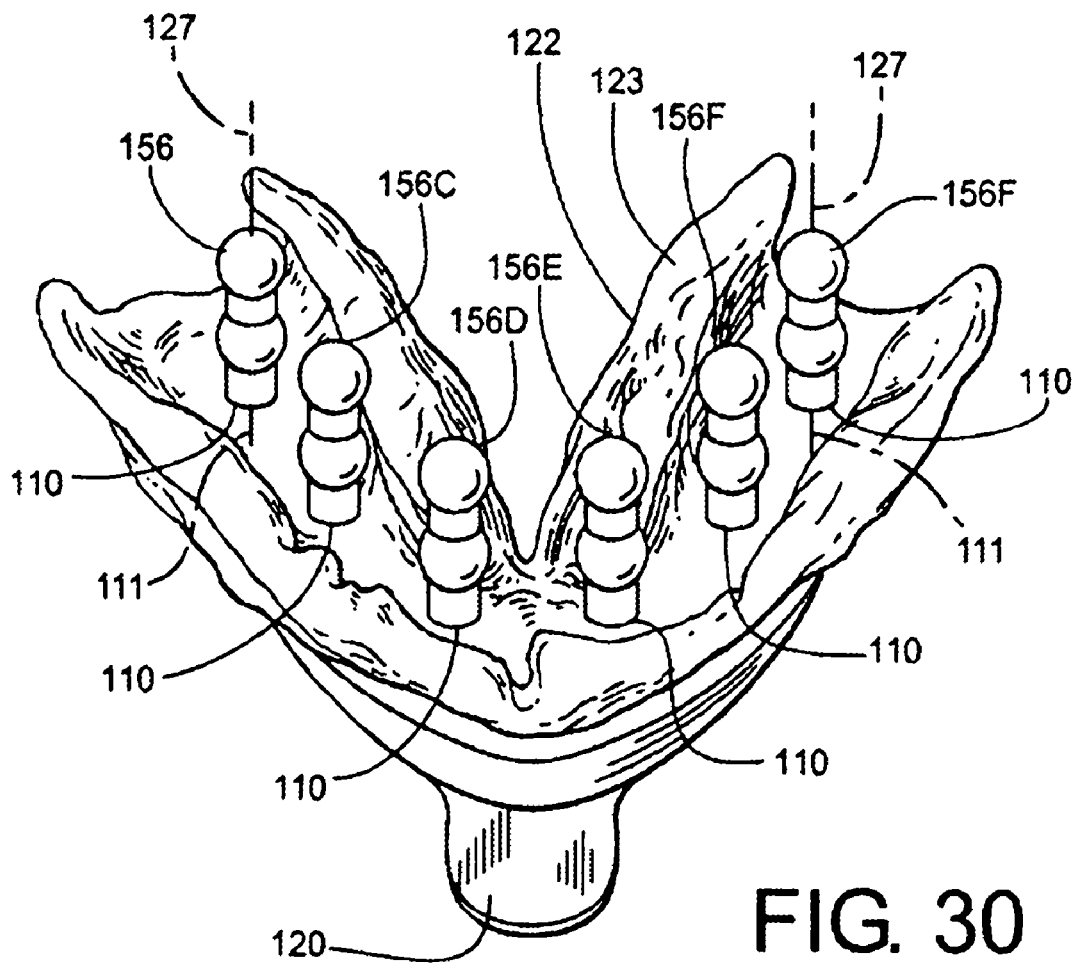
FIG. 30 is a perspective view of an impression with coping extending therefrom to which alignment posts have been attached.

In a fourth alternative process, illustrated in FIG. 30, the dentist fixes the alignment posts 156 directly to the copings 110. The alignments posts are suitably modified to mate with the copings 110 in a predetermined position, preferably coaxial with the copings, such that the surface extensions of the alignment posts can, as in the previous examples, be scanned and the location and orientation of the copings determined with some accuracy just as in the previous processes the surface of the fittings to which the alignment posts were attached was determined accurately using the surface extensions on the alignment posts.

A fifth alternative process for manufacturing the final framework provides for a more accurate determination of the position and orientation of the fitting mating surfaces 160, 162, 164, 166, 172, 174, as shown in FIG. 15 and FIG. 16, by using scan data from the stone cast 125, while allowing the dentist or laboratory technician to create a wax-up framework 150 and thereby participate in the design of the final framework. The wax-up framework generally is comprised of a material that can easily be formed into a desired shape using flexible molding materials such as wax, acrylic, and other polymers. When the alignment posts 156 are attached directly to wax-up framework 150, the weight of the alignment posts 156 may place flexural pressure on the wax-up framework 150 and may distort the placement of the fittings 152 relative to one another. This distortion may be great enough to noticeably affect the position and orientation of the mating surfaces of the manufactured final framework.

This fifth alternative process is advantageous because the stone cast 125 better withstands flexural pressure placed upon it from the weight of the alignment posts 156 and accurately retains the position and orientation of the fittings 152 relative to one another resulting in a more accurate fit of the final framework. Such accuracy creates an ideal fit of the framework in the patients mouth the first time the framework is made, thereby saving the patient and dentist time and money. This alternative process is also advantageous because the dentist and/or laboratory technician may participate in the final framework design through the physical creation of a desired framework configuration by means of building a traditional wax-up framework 150.

In the fifth alternative process, the dentist creates a stone cast 125 of the patient's mouth and a wax-up framework 150 compatible with the framework manufacturer's process as described above. Similar to the first alternative process, alignment posts are attached to the stone cast 125 and scanned by an acceptable means. The wax-up framework 150 is scanned, capturing the contours of the fittings 160, 162, 164, 166, 172, 174 and bridging structure 154 designed by the dentist or dental laboratory technician to capture a digital representation 205 in the form of a point cloud dataset 150'. Next the alignment posts are removed from the stone cast 125 and the wax-up framework 150 is placed upon the stone cast 125. Each fitting 152 of the wax-up framework 150 is coupled to each corresponding analog 124 such that the wax-up framework 150 is in a proper mated configuration to the stone cast 125. The wax-up framework 150 and stone cast 125 are then scanned together. These scans may be made in any order preferred by the operator. These scans are then aligned using shared features of the stone cast 125 and wax-up framework 150. Such features include, but are not limited to, surface contours, vertices, planes, lines, curves, or points. Once the scans are aligned, an accurate determination can be made of the position and orientation of the mating surfaces 160, 162, 164, 166, 172, 174 of the wax-up framework 150. Scan alignment aids used in the art of digitally scanning objects to assist in alignment of the scan data may be used in the scanning process. Such alignment aids include, but are not limited to window pane fixtures, alignment posts, and calibration fixtures.

Figure 37:
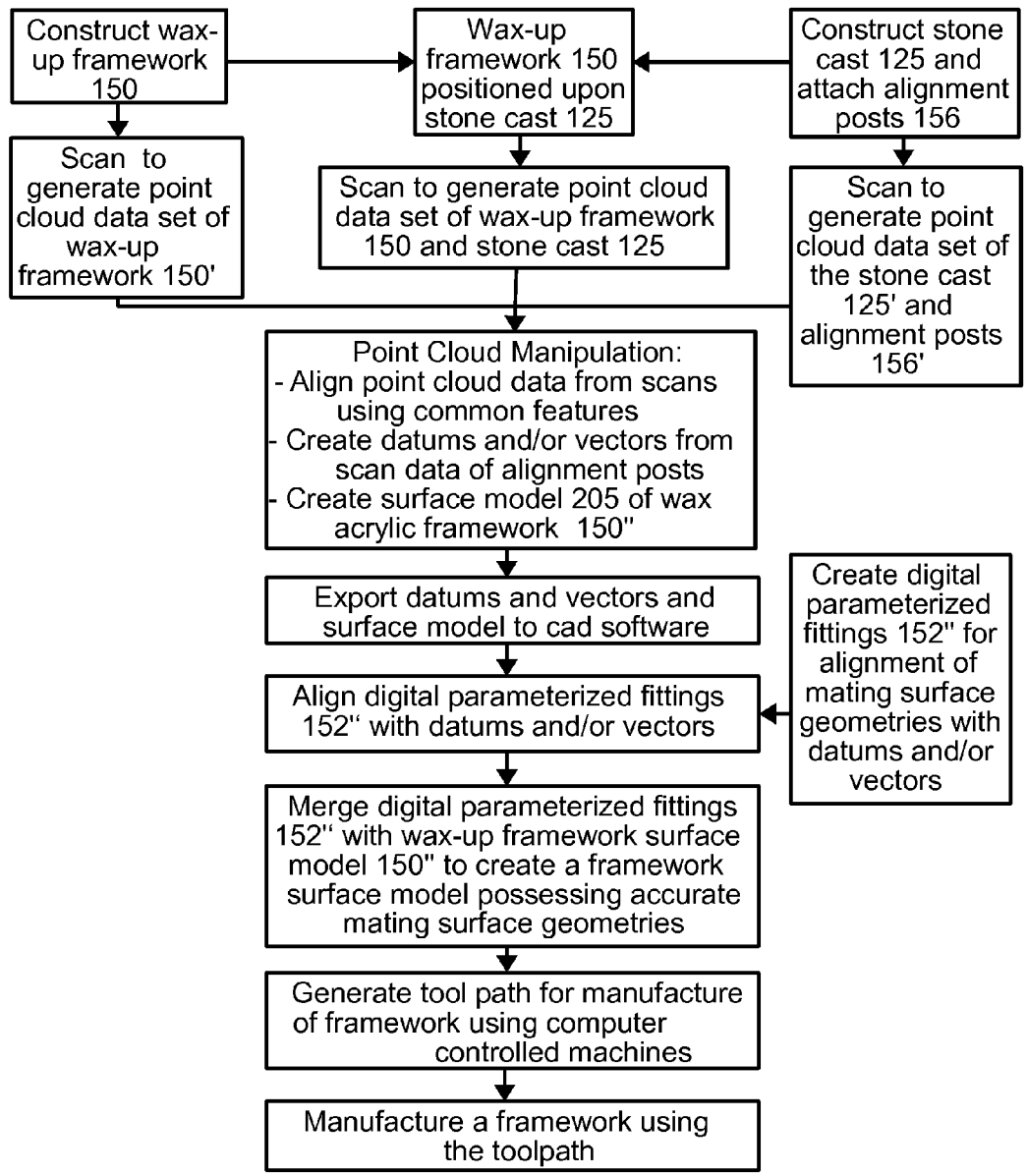
FIG. 37 is a flowchart of the process of manufacturing a denture framework having a general exterior shape nearly identical to the wax-up framework.

Similar to the procedures described in steps 220-226, digital parameterized fittings 152" which define in parametric form the location and orientation of the mating surfaces 160, 162, 172, 174 of the final manufactured framework fittings 152, are placed according to the point cloud data of the scan acquired from the stone cast 125 with alignment posts 156. In the preferred embodiment, the point cloud data of the alignment post surface extensions 176, 178, 180, 256, 258, 260, 268, 274, 286, 288, 290 is used to create datums 198, 199 as described above. A surface model 150" of the wax-up framework 150 is generated that defines the contours of the framework 150. Generally the datums (198, 199) are created after alignment of the scans, and prior to creation of the surface model 150", however the steps of creating the datums (198, 199), creation of the surface model 150" and alignment of the scans can be made in any order preferred by the operator. The digital parameterized fittings 152" are aligned and combined with the wax-up framework surface model 150" by aligning the digital parameterized fittings 152" using datums (198, 199) previously discussed. The digital parameterized fittings 152" and surface model of the wax-up framework 150" are combined, preferably by Boolean union. This model may then be subjected to other modifications. The subsequent surface model of the framework is manufactured as in step 212 or step 230. This process is shown in the flowchart in FIG. 37.

Figure 38:
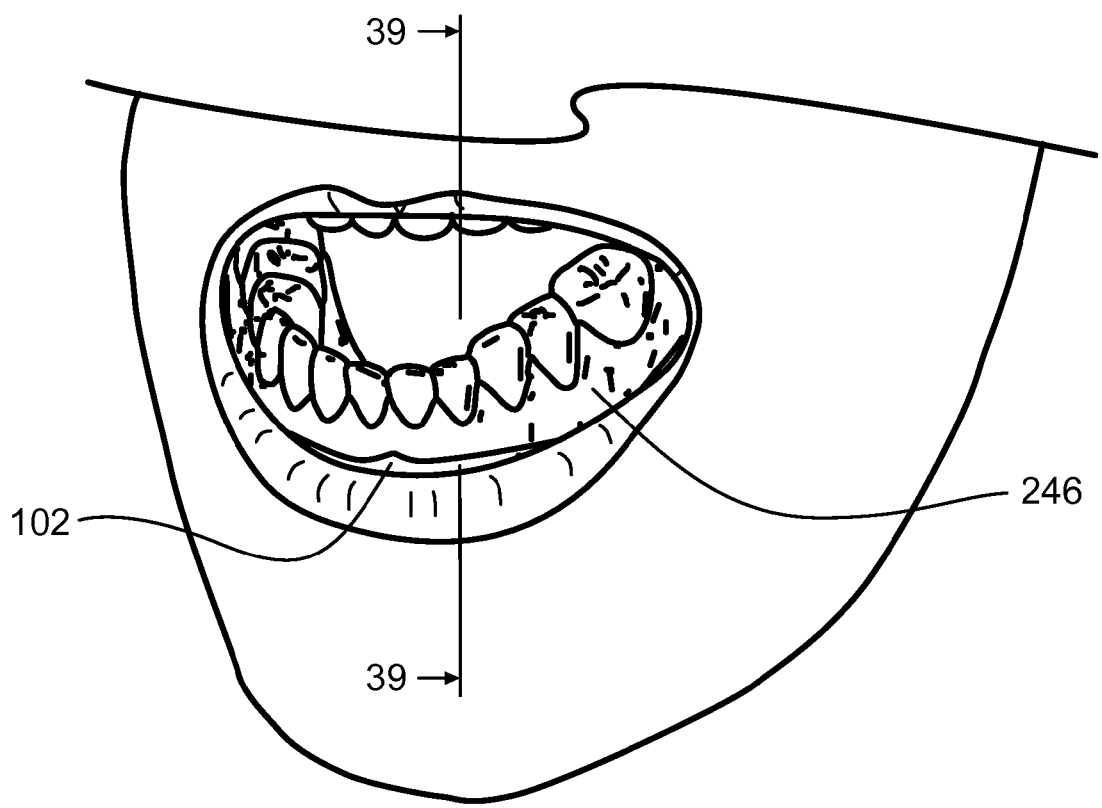
FIG. 38 is a fragmentary perspective view of a patient's open mouth with a finished denture mounted to the manufactured framework.
Figure 39:
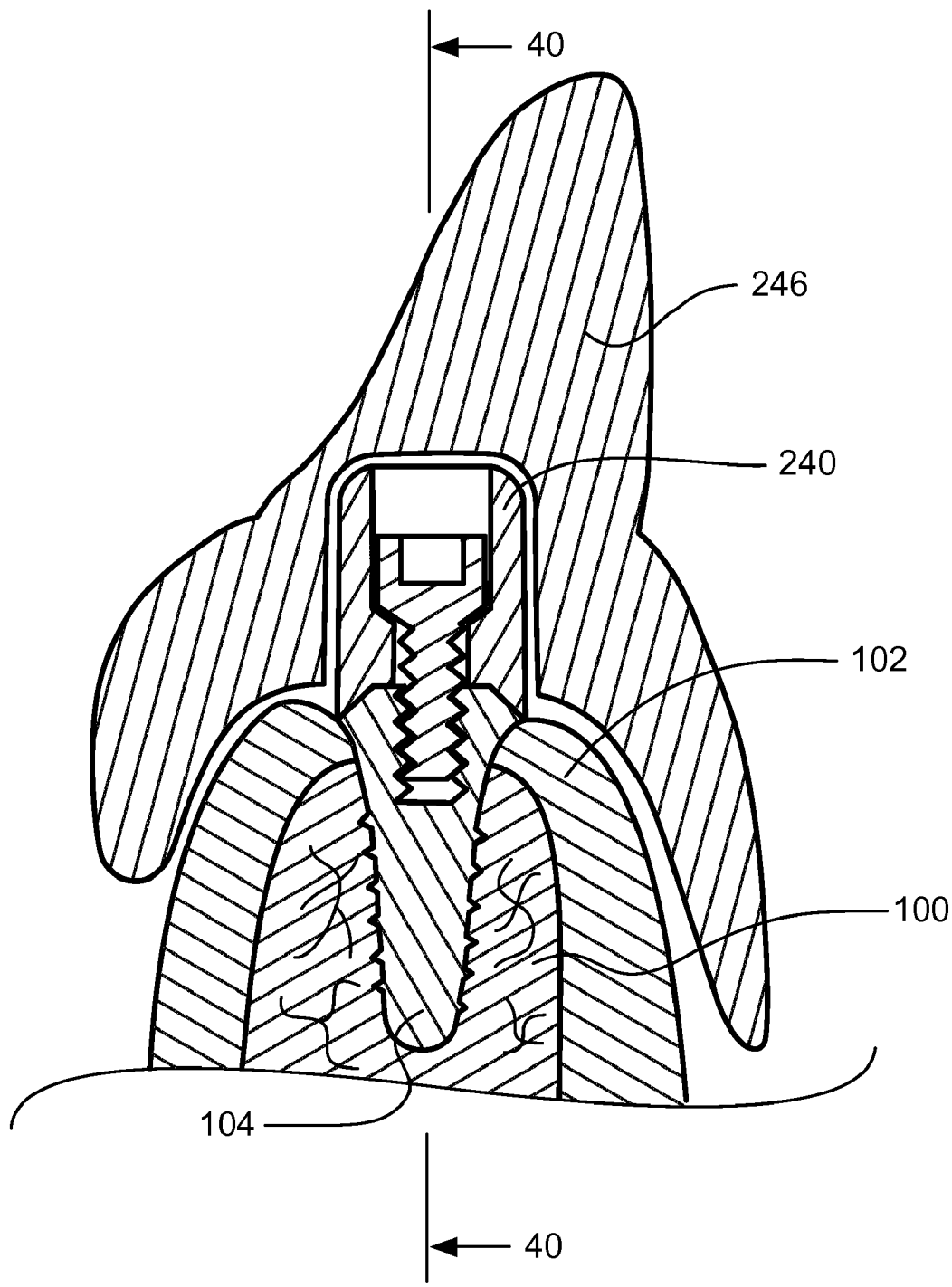
FIG. 39 is a cross sectional view on the line 39-39 in FIG. 38 showing the denture, framework and anchor embedded in the patient's jaw.
Figure 40:
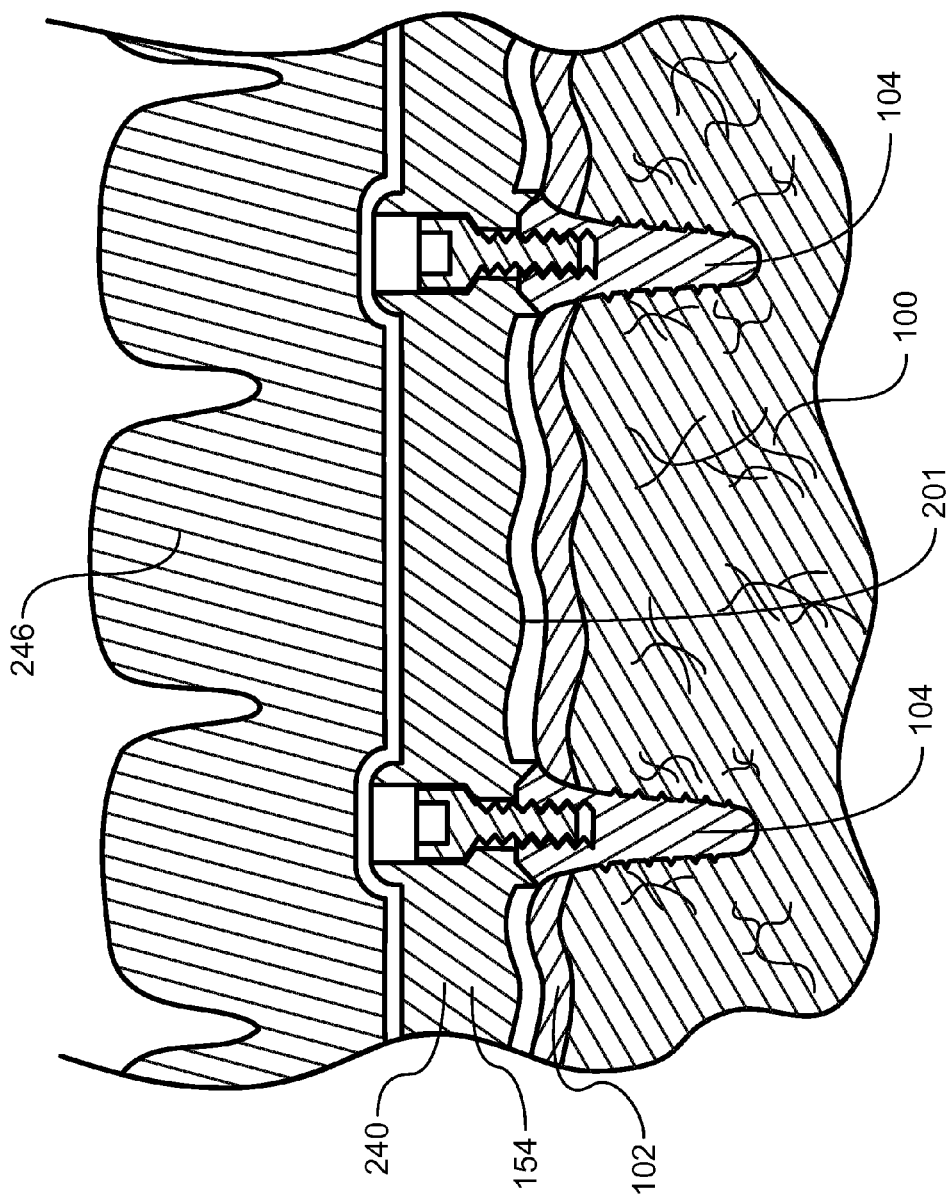
FIG. 40 is a cross sectional view on the line 40-40 in FIG. 39 showing a dental framework and an anchor embedded in the patient's jaw this view being perpendicular to the cross section shown in FIG. 39. The dental framework has a tissue confronting surface contoured to compliment the contours of the confronting soft tissue surface.
Figure 45A:
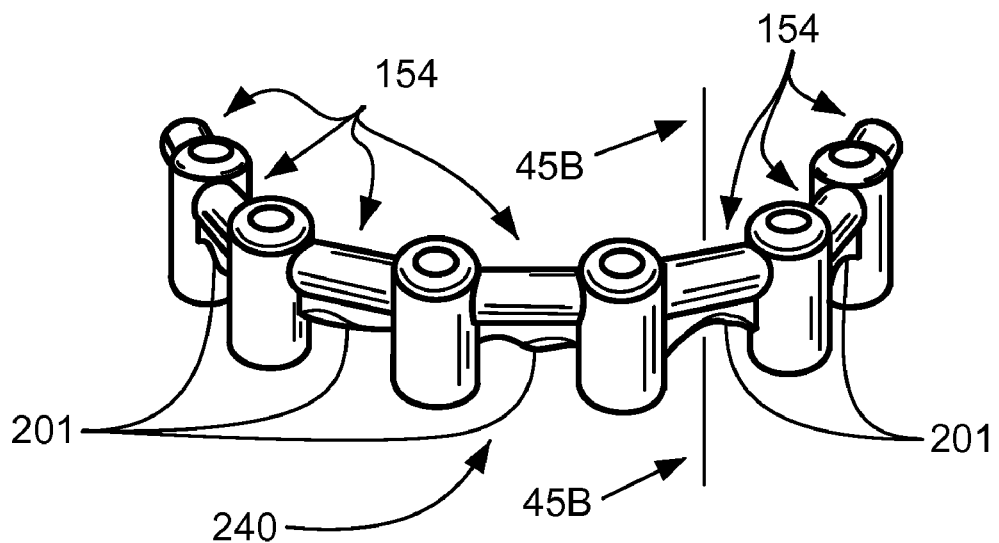
FIG. 45A is a perspective view of the final contoured dental framework.
Figure 48A:
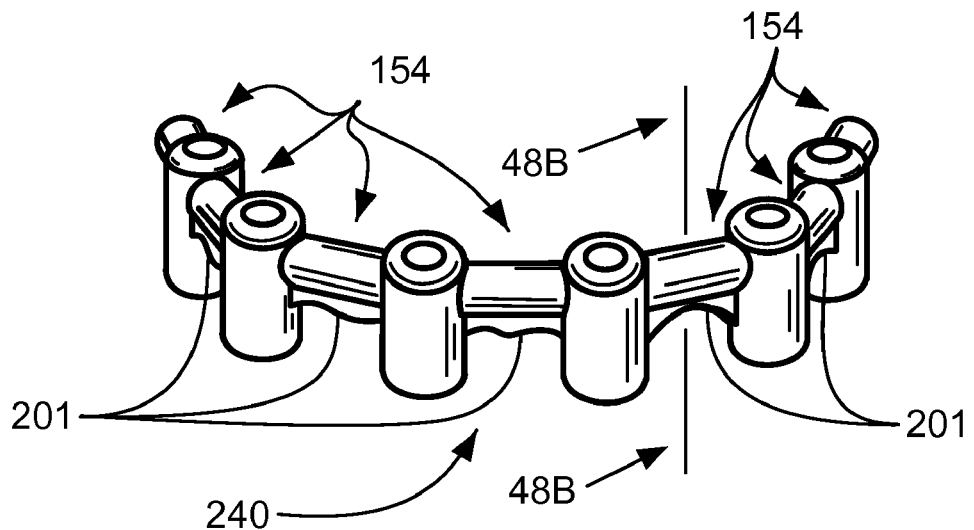
FIG. 48A is a perspective view of the final straight cut contoured dental framework.

A sixth alternative process is used for manufacturing a final contoured framework 240 which has a contoured bridging structure 154 that follows the contours of the patient's soft tissue. FIGS. 45A and 48A show the contoured framework 240. The contoured framework 240 is advantageous in that it reduces the potential for food particles to become trapped thereby reducing instances of bad breath, soft tissue irritation, infection, and gum disease. The contoured framework 240 also increases the patient's comfort and provides the patient with a more natural feeling denture. A bridging structure 154 follows the contours of the gum tissue also prevents excess air from traveling between the gum tissue and denture, improving the patient's phonetics. The final denture 246 and contoured framework 240 manufactured by this sixth alternative process is shown in the patient's mouth in FIG. 38. FIG. 39 shows a cross section of the denture 246, the contoured framework 240, the anchor 104, the mandible bone 100, and the soft gum tissue 102. FIG. 40 is a section taken line 40-40 in FIG. 39 along the length of the bridging structure 154 of the contoured framework 240 showing the undulating surface 201 of the bridging structure 154 confronting and following the contour of the surface of the soft tissue 102.

In a further embodiment of the method of manufacture of the dental framework, the dentist manufactures the stone cast 125 and either a wax-up framework 150, a diagnostic wax up 130 or a putty index 142 as hereinbefore described. Alignment posts 156 are coupled to the appropriate mating surfaces, these items are scanned, the location and orientation of the mounting surfaces determined, appropriate datums, vectors, surfaces, and/or planes are generated, surface models and/or point clouds of the appropriate objects created, digital parameterized fittings 152" imported and properly oriented, and a bridging structure 154' constructed in the processes as herein described.

A soft tissue surface model 125" of stone cast 125 is created which does not include the mating surfaces of the analogs 110. The soft tissue surface model 125" in this embodiment includes the contours of the patient's soft tissue 102 captured in impression 123 and recreated in stone cast 125. The contours of the patient's soft tissue may also include other contours of the patient's mouth confronting the bridging structure of the framework, including surfaces contours of other dental restorations or other prosthetic devices.

Figure 41:
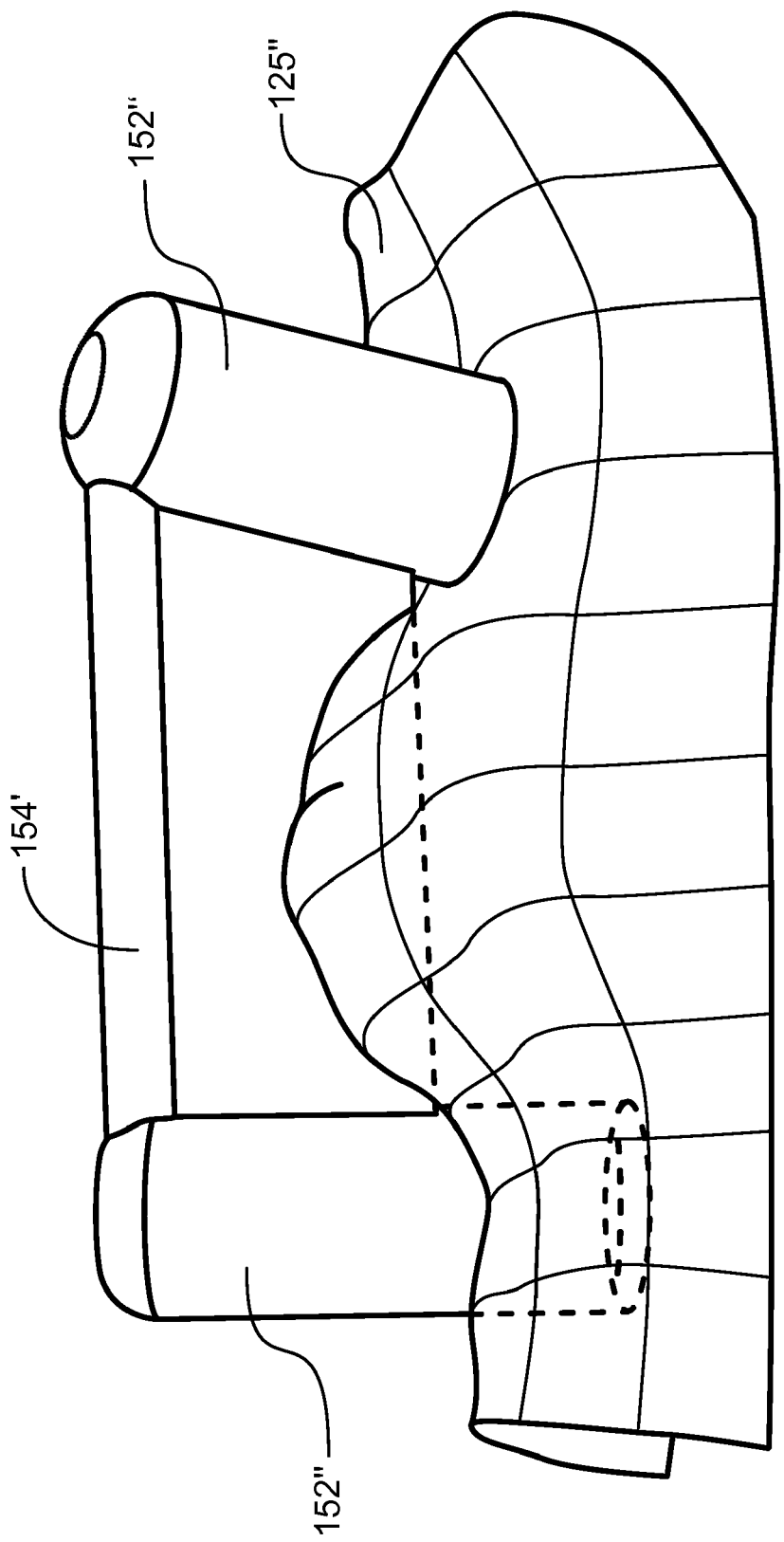
FIG. 41 is a facial view of a digital model of two fittings connected with a bridging structure positioned over a digital representation of the gum surface, the bridging structure passing through the digital representation of the gum surface.
Figure 42:
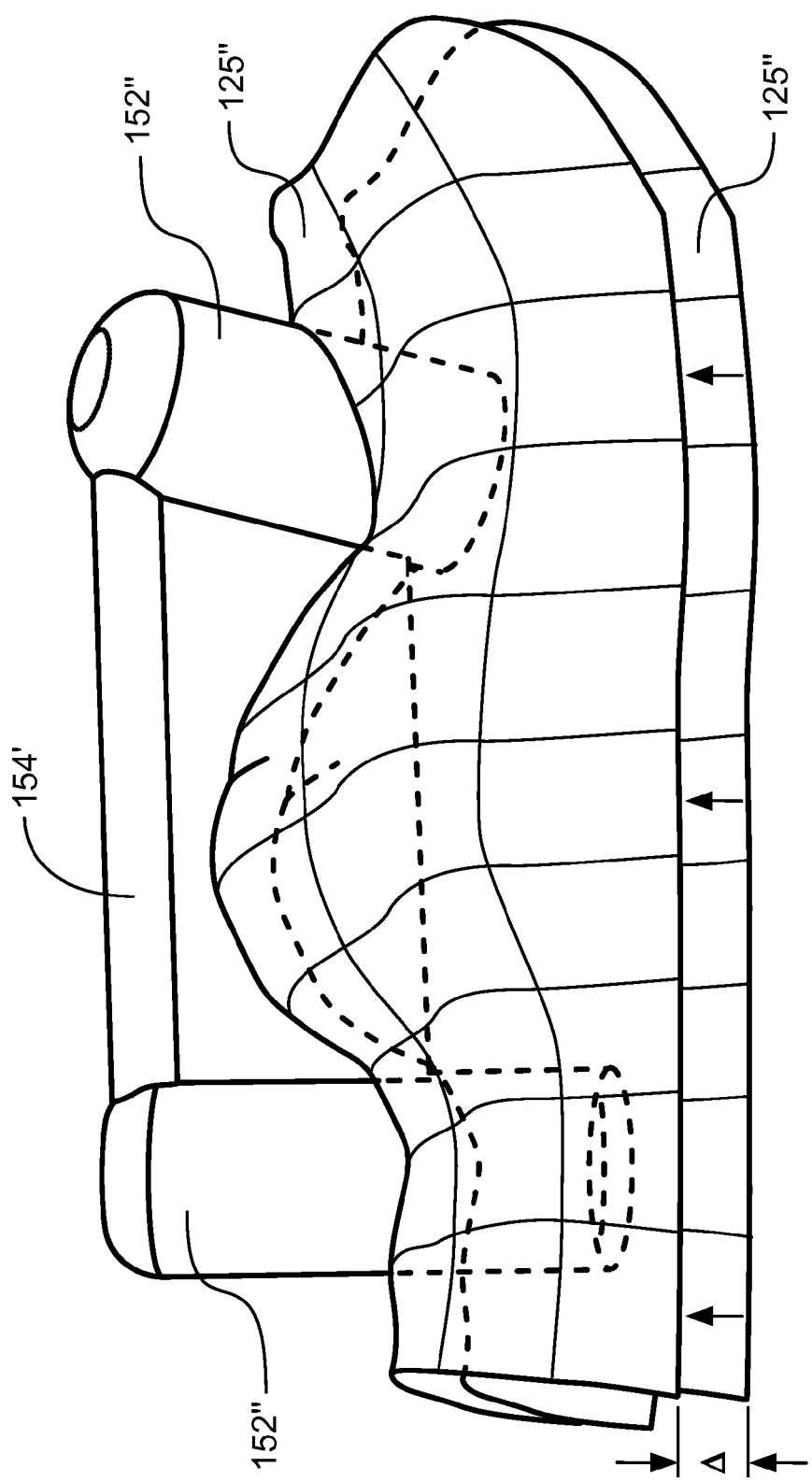
FIG. 42 is a facial view of a digital model of two fittings connected with a bridging structure positioned over a digital representation of the gum surface, the bridging structure passing through the digital representation of the gum surface. The arrows showing the operator's desired repositioning of digital gum surface representation in preparation for modification of the bridging structure.

Soft tissue surface model 125" of stone cast 125 is then used to accurately contour the soft tissue side of bridging structure 154' to the contours of the patient's soft tissue 102 and other structures in the patients mouth thereby forming a contoured framework digital model 238. Soft tissue surface model 125" is imported by computer 186 into it's original placement relative to the digital parameterized fittings 152" and the bridging structure 154' as shown in FIG. 41. The bridging structure 154' is modified to extend toward the gum surface. Generally, at this stage, a portion of the bridging structure 154' will extend below the soft tissue surface model 125". The soft tissue surface model 125" may then be displaced, rotated or otherwise oriented into an alignment requested by the customer determined automatically by a computer or chosen by the operator to provide an appropriate clearance between the patient's mucosal tissue 102 and the confronting surface of the bridging structure 154' as shown in FIG. 42. The operator may then proceed with creating a fully contoured or a straight cut confronting surface on the bridging structure. The operator may choose to shape a portion or all of the gum confronting surface of one or more bridging structures by the fully contoured method or straight cut method as described below.

Figure 43:
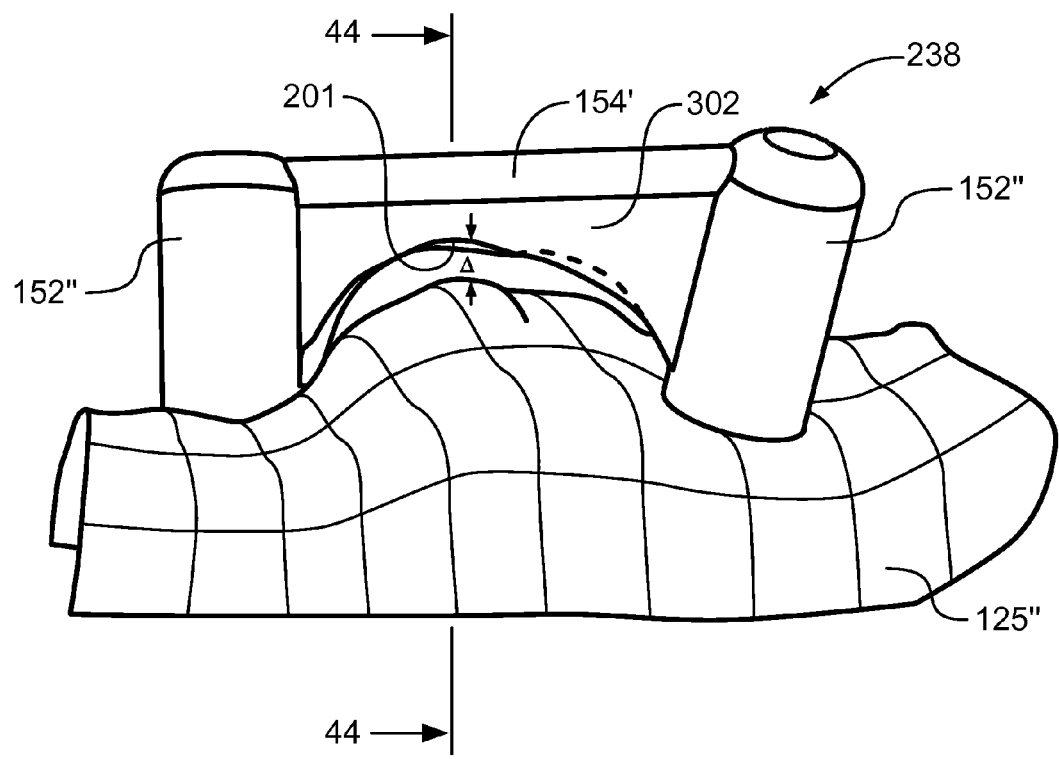
FIG. 43 is a facial view of a digital model of two fittings connected with a bridging structure positioned over a digital representation of the gum surface, the bridging structure's gum confronting surface cut to compliment the contours of the underlying gum surface.
Figure 44:
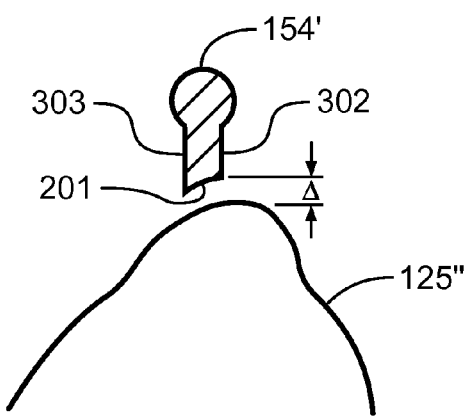
FIG. 44 is a cross sectional view on the line 44-44 in FIG. 43 showing the bridging structure and gum surface.
Figure 45B:
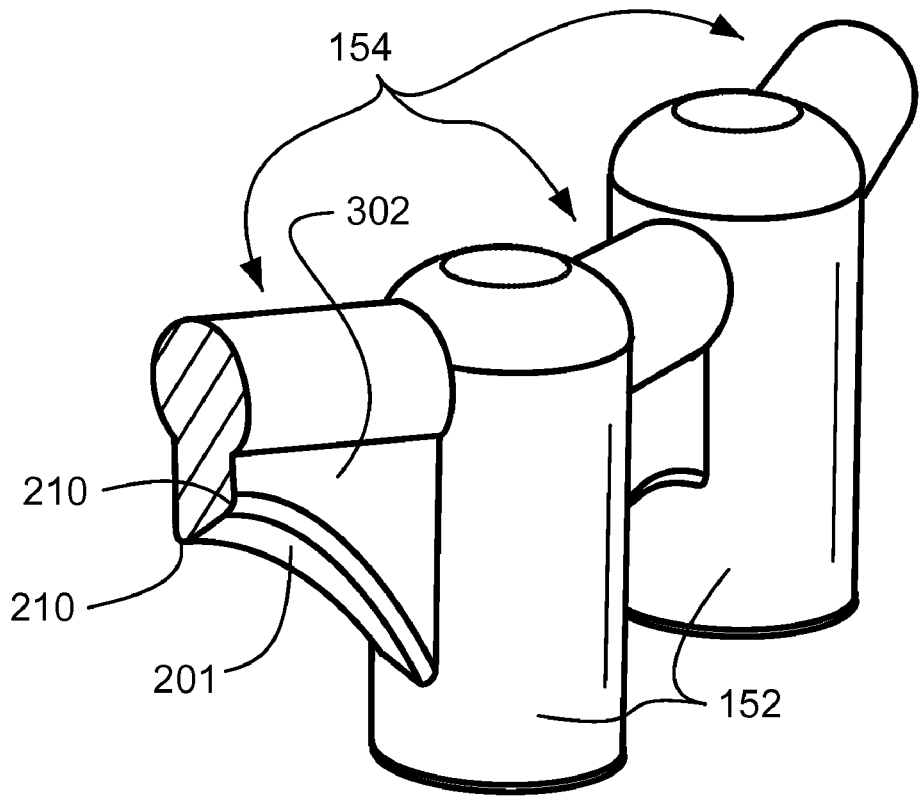
FIG. 45B is a fragmentary perspective view cut on the line 45B-45B in FIG. 45A of the contoured dental framework, the bridging structure cut to compliment the contour of the underlying gum surface.

FIG. 42 shows a bridging structure 154' and the soft tissue surface model 125" vertically displaced by distance A. The soft tissue surface model may also be displaced and rotated in other directions as desired by the customer or operator. In the preferred method, the volume of the bridging structure 154' that extends beyond the soft tissue surface model 125" is then removed. Soft tissue surface model 125" is used as a Boolean subtract tool to create a cut in the bridging structure 154'. The cut results in an undulating surface 201 of the bridging structure 154' confronting the soft tissue as shown in FIG. 43. FIG. 44 shows the cross-sectional profile of the undulating contoured surface 201 following the contours of the soft tissue surface model 125". While a Boolean subtraction is performed in the preferred embodiment, other software algorithms may be used to generate a bridging structure surface complimentary to the gum surface contours, including extrusion up to the surface of the soft tissue surface model and/or a Boolean addition. Alternatively the contoured surface 201 may have a cross-sectional profile surface shape generally following the contours of the soft tissue surface model 125". By having a gum confronting surface that generally follows the contours of the soft tissue surface model as opposed to following each undulation of the soft tissue, the gum confronting surface undulations can be reduced in number and curvature, thereby reducing the likelihood of food becoming trapped and simplifying manufacturing procedures. Any number of bridging structures 154' may be shaped to compliment the surface of the soft tissue confronting the bridging structure, allowing the operator to create one or more bridging structure 154' with a soft tissue confronting surface that does not compliment the contours of the soft tissue surface model 125". FIG. 45A shows a final contoured framework 240 possessing a contoured gum confronting surface 201 on the interior five bridging structures 154. These five interior bridging structures 154 are shaped to compliment the contours of the confronting gum tissue while the two outermost bridging structures 154 are not shaped to the compliment the confronting gum tissue contours. Also, a bridging structure 154 may not have the entire confronting surface 201 shaped to conform to the soft tissue model 125". In this alternative process, at least a portion of one of the bridging structures 154 in the final framework 240 is shaped to the contour of the confronting soft tissue. Vertices formed between the confronting surface 201, the facial surface 302, and lingual surface 303 of the bridging structure may create sharp angles that may otherwise be undesirable. FIG. 45B shows a fragmentary perspective view of the finished contoured dental framework 240 cut on the line 45B-45B in FIG. 45A. To reduce these sharp angles the cross-sectional profile may possess surface blends or edge rounds 210 as shown in FIG. 45B. Other cross-sectional cut profiles may include elliptical, rounded, multifaceted, chamfered, and nonplanar free-form profiles.

Figure 46:
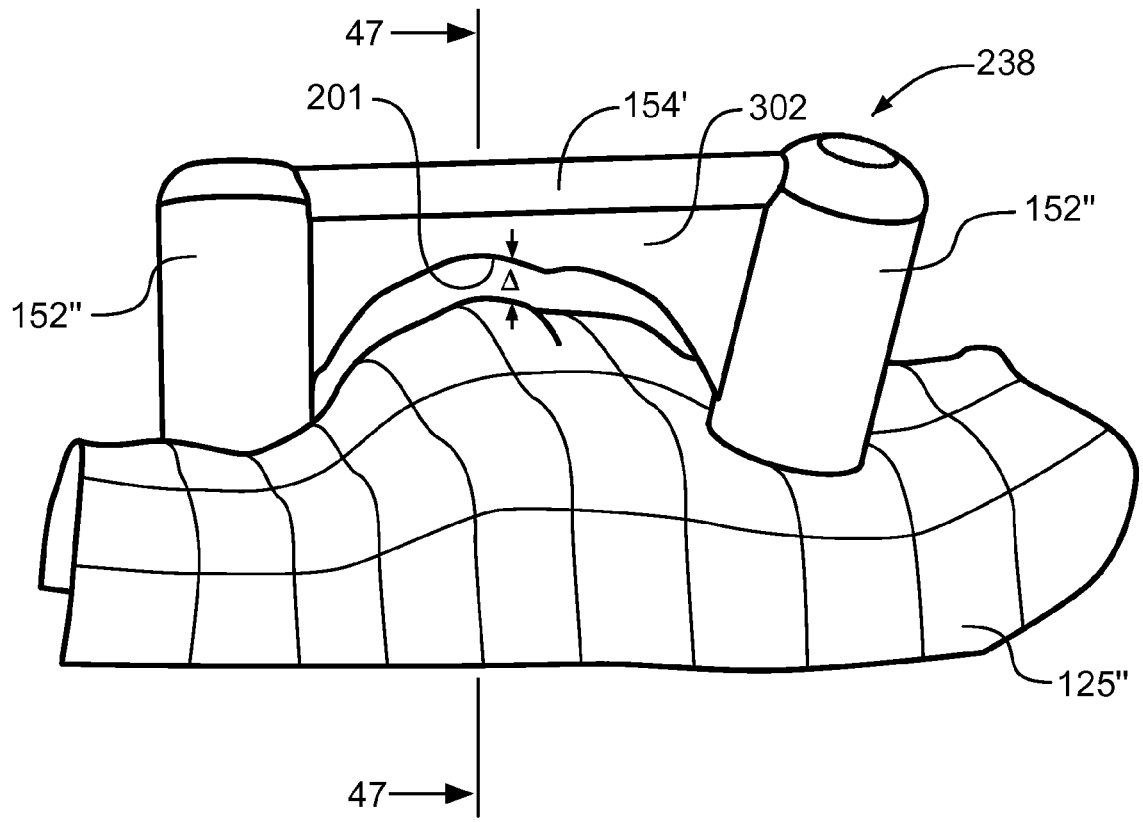
FIG. 46 is a facial view of a digital model of two fittings connected with a bridging structure positioned over a digital representation of the gum surface, the bridging structure's gum confronting surface straight cut to compliment the longitudinal contour of the underlying gum surface.
Figure 47:
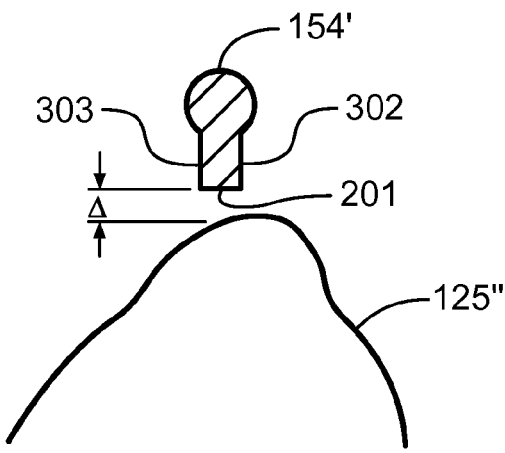
FIG. 47 is a cross sectional view on the line 47-47 in FIG. 46 showing the bridging structure and gum surface.
Figure 48B:
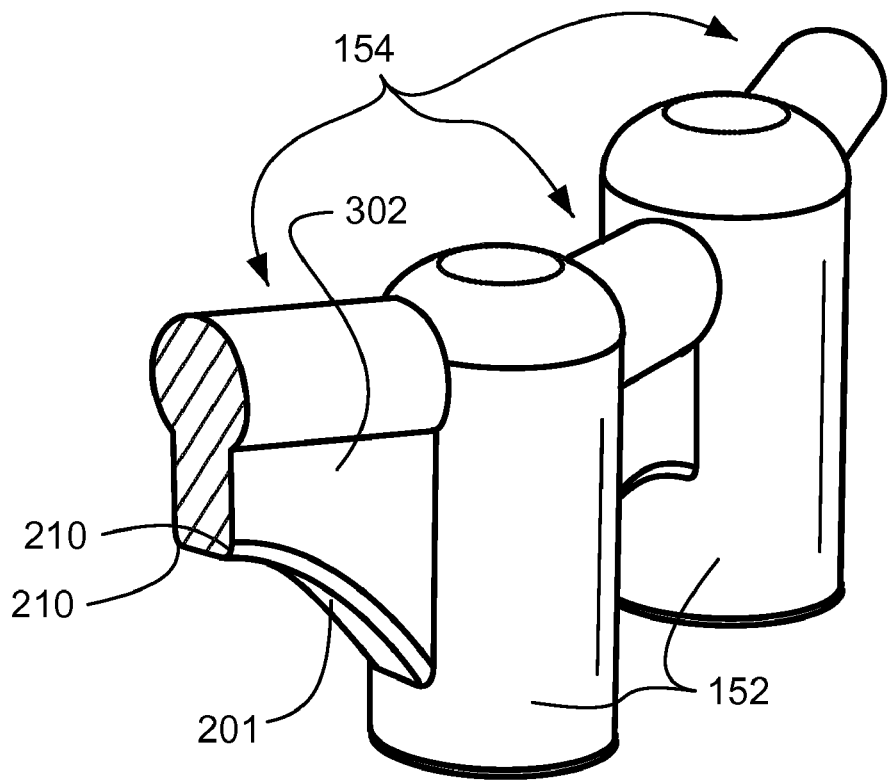
FIG. 48B is a fragmentary perspective view cut on the line 48B-48B in FIG. 48A of the contoured dental framework, the bridging structure straight cut to compliment the longitudinal contour of the underlying gum surface.

A further embodiment of the invention is shown in FIG. 46 in which the surface 201 of the bridging structure 154' of the contoured framework digital model 238 is straight cut. The straight cut results in a cross-sectional profile lower surface 201, as shown in FIG. 47, that is generally perpendicular to the facial and lingual sides 302, 303 of the bridging structure 154'. Similar to the fully contoured surface, the flat cut surface is created by offsetting the soft tissue surface model 125" by distance Δ as shown in FIG. 42. The soft tissue surface model may also be displaced and rotated in other directions to achieve the desired results. A path is then chosen along the soft tissue surface model 125" that lies below the bridging structure 154'. While the chosen path may follow the contour of the soft tissue surface model 125" exactly, the operator may choose to smooth the path such that each undulation of the soft tissue surface model 125" is not followed and a smoother straight cut contoured surface 201 is achieved. A cut profile is created that is generally perpendicular to the bridging structure sides 302, 303 and then swept across the chosen path. The cut results in a contoured surface 201 of the bridging structure 154' confronting the soft tissue as shown in FIG. 46. FIG. 47 shows the cross section of the contoured surface 201 following the contours of the soft tissue surface model 125" cut on the line 47-47 in FIG. 46. While a Boolean subtraction is performed in the preferred embodiment, other software algorithms may be used to generate a bridging structure straight cut surface complimentary to the gum surface contours 201. Alternatively, the straight cut surface can be formed by choosing a path along the soft tissue surface model 125" below the bridging structure 154', choosing a cut profile and sweeping the cut profile along the chosen path to create a contoured surface 201 followed by extrusion up to the contoured surface 201 from the bridging structure followed by a Boolean addition. Any number of bridging structures 154' may be straight cut to compliment the surface of the mouth confronting the bridging structure, allowing the operator to create some bridging structures 154' with a soft tissue confronting surface that does not compliment the contours of the soft tissue surface model 125". FIG. 48A shows a final contoured framework 240 having five interior bridging structures 154 shaped by the method of the straight cut to compliment the contours of the confronting gum tissues while the two outermost bridging structures 154 are not shaped to the contour of the confronting soft tissue. A bridging structure 154 may have only a portion of the confronting surface 201 shaped to conform to the soft tissue model 125". In this embodiment, at least a portion of one of the bridging structures 154 in the final framework 240 is shaped to the contour of the confronting soft tissue in accordance with the straight cut cross sectional profile. FIG. 48B shows a fragmentary perspective view of the finished straight cut contoured dental framework 240 cut on the line 45B-45B in FIG. 45A. The straight cut may have surface blends or edge rounds 210 as shown in FIG. 48B. Other cut profiles may be formed such that the lower gum confronting surface 201 has a cross sectional profile that is elliptical, rounded, multifaceted, chamfered, or a nonplanar free-form profile, or any combination thereof. The straight cut has the advantage of reducing the instances of sharp edges and concave recesses that may trap food particles and otherwise irritate or cut the soft tissue of the gums or tongue. The straight cut also reduces design and manufacturing time resulting in framework possessing the heretofore mentioned benefits at a reduced cost to the customer over framework having a fully contoured gum-confronting surface.

The straight cut profile generally follows the contours of the soft tissue surface model 125'' along the length of the bridging structure 154'. The profile of the straight cut is determined by selecting a path along the surface of the soft tissue surface model 125'' that confronts the bridging structure 154'. In the preferred embodiment the path lays directly in plane with either the lingual surface 303 or facial surface 302 of the bridging structure 154'. In such embodiment, the operator may examine the alternative paths and select the path lying closer to the bridging structure. In another embodiment, the operator selects a path along the contour of the gum tissue lying in a plane parallel to either the facial or lingual surface of the bridging structure including a path directly beneath the lateral midpoint of the surface of the bridging structure confronting the soft tissue. The lateral midpoint is the midpoint between the facial side 302 and lingual side 303 of the bridging structure 154. In yet another embodiment, the operator selects a nonlinear path bound by the planes of the lingual surface 303 and facial surface 302. When the operator selects a nonlinear path that lies closest to the bridging structure 154', it has the advantage of creating a uniform maximum gap along the length of the bridging structure 154' between the confronting surface of the soft tissue surface 125'' and the bridging structure 154'

The digital model of the contoured framework 238 may be accomplished with a bridging structure generated from scan data acquired from the stone cast 125 and the diagnostic wax-up 130, the stone cast 125 and the putty index 142 or the stone cast 125 and the wax-up framework 150. The digital model contoured framework 238 may have an bridging structure generated from a wax-up framework surface model 150'' such as accomplished in the fifth alternative process herein described.

In the discussion above, scans of surface extensions on the surface of alignment posts are used to provide a more accurate determination of the location of the objects to which they were attached. The position and orientation of these objects are determined by the position and orientation of the mounting surfaces of anchors embedded in the patient's maxilla or mandible. The scans therefore indicate, incorporate or encode the position and orientation of the anchors.

The alignment posts above are elongate members having spherical surface portions (e.g. the surface extensions) at various positions along their length. These are merely exemplary, however. FIGS. 31-36 illustrate alternative alignment posts 250, 252, 254 that provide scannable surface extensions that can be coupled to any of the structures indicate above to which the alignments posts of the foregoing figures were attached to serve the same function: to provide scannable surface extensions that are in predetermined locations with respect to the mounting surfaces to which the base of the alignment posts are coupled. FIGS. 31-32 show an alignment post that is configured to be attached to any one of fittings 152C-152F. Referring to FIGS. 31 and 32, alignment post 250 is shown. It has three spherical surface extensions 256, 258, 260 that are in a predetermined position with respect to the base 262 of the alignment post 250. In this embodiment, the centers 264 define a plane that extends perpendicular to the longitudinal axis 266 of the alignment post 250. This axis 266 intersects the plane at a point equidistant to all of centers 264. The point equidistant is a predetermined distance along axis 266 from base 262. Computer 186 is programmed with this parametric information and is configured to scan the surface extensions, determine the plane, determine the longitudinal axis and the position along the longitudinal axis where base 266 is located, a well as the location and orientation of the mounting surfaces of the structure to which the base is connected.

FIGS. 33-34 show another alignment post arrangement having a first spherical surface extension 268 lying on the longitudinal axis 272 of base 270. A second surface extension 274, shown here as a flat plane, is also disposed along and perpendicular to longitudinal axis 272 and a predetermined distance away from base 270. As in the previous examples, computer 186 is configured to scan the surface extensions, determine the center of spherical surface extension 268, determine the plane of surface extension 274, and determine the longitudinal axis 272 and the position along the axis where base 272 is located, as well as the location and orientation of the mounting surfaces of the structure on which the base 272 is connected.

FIGS. 35-36 show another alignment post arrangement having a first surface extension 280 forming a plane that is normal to the longitudinal axis 284 of base 282. A second surface extension 286, shown here as a flat plane, is disposed parallel to longitudinal axis 284 a first distance away from the axis. A third surface extension 288 shown here as a flat plane is also disposed parallel to longitudinal axis 284 the first distance away from the axis. A fourth surface extension 290 shown here as a flat plane is also disposed parallel to longitudinal axis 284 the first distance away from the axis. Each of the three surface extensions parallel to the longitudinal axis 284 are spaced equiangularly with respect to each other about the longitudinal axis to define an equilateral triangle in an end view (FIG. 36). As in the previous examples, computer 186 is configured to scan the surface extensions, determine the planes of the surface extensions center of spherical surface extension 268, determine the planes of the surface extensions determine the longitudinal axis 282 and the position along the axis where base 284 is located, as well as the location and orientation of the mounting surfaces of the structure on which the base 284 is connected.

What is claimed is:

1. A method of fabricating a dental framework conforming to the soft tissue of a patient, the dental framework for use in a dental prosthesis, the dental framework having a plurality of fittings interconnected by bridging structures, said fittings having mating surfaces that are configured to engage a corresponding plurality of anchors in said patient's jaw bone, and each of said bridging structures having a soft tissue confronting surface, the method comprising the steps of:
   creating a digital representation of a soft tissue surface of said patient's mouth associated with said jaw bone;
   creating a digital model of said dental framework;
   positioning, using a computer, said digital model of said dental framework and said digital representation of said soft tissue surface in relationship with one another; and
   making said dental framework conforming to the soft tissue of said patient in accordance with a toolpath including removing any material from said soft tissue confronting surface of said bridging structures of said framework extending through said digital representation of said soft tissue surface.

2. The method of claim 1, wherein said soft tissue surface of said patient includes a surface of at least one of a group consisting of soft tissue, gum tissue, other prosthesis and other restoration surface.

3. The method of claim 1, wherein said digital representation of said soft tissue surface is created by means of scanning a dental surface of at least one of a group consisting of an impression of said patient's mouth, a stone cast of said patient's mouth, a diagnostic wax-up and a wax-up framework.

4. The method of claim 1, wherein said material is removed from said bridging structure by exactly following said soft tissue surface contour of said digital representation of said patient's mouth.

5. The method of claim 1, wherein said digital representation of said soft tissue surface is created by taking an impression of said patient's mouth, manufacturing a stone cast of said patient's mouth from said impression and digitally scanning said stone cast.

6. The method of claim 5, wherein subsequent to manufacturing said stone cast, a diagnostic wax-up is created followed by creation of said digital model of said framework by means of scan data acquired from said stone cast and said diagnostic wax-up.

7. The method of claim 6, wherein said diagnostic wax-up is created from a material containing at least one material selected from a group consisting of wax, acrylic, and polymer material.

8. The method of claim 5 wherein subsequent to manufacturing said stone cast a putty index is created, then said digital model of said framework is created by using scan data acquired from said stone cast and said putty index.

9. The method of claim 5, wherein subsequent to manufacturing said stone cast a wax up framework is created, then said digital model of said framework is created using scan data acquired from said stone cast and said wax-up framework.

10. The method of claim 9, wherein said wax-up framework is created from at least one material selected from a group consisting of wax, acrylic, and polymer material.

11. The method of claim 5, wherein subsequent to manufacturing said stone cast a wax up framework is created, then said digital model of said framework is created using scan data acquired from said stone cast and said wax-up framework, said digital model having a shape substantially-identical to that of said wax-up framework scan data.

12. The method of claim 11, wherein said wax-up framework is created from a material selected from a group consisting of wax, acrylic, and polymer material.

13. The method of claim 5, wherein said stone cast is created by a method comprising the steps of:
    attaching a coping to each of said anchors;
    forming an impression of said patient's mouth in which said copings are embedded;
    attaching an analog to each of said copings; and
    forming a stone cast from said impression in which said analogs are embedded.

14. The method of claim 1, wherein said digital model of said framework is created by:
    creating a digital model of said bridging structures;
    creating a digital model of said fittings and
    combining said digital model of said bridging structures and said digital model of said fittings.

15. The method of claim 1, wherein said digital model of said framework is created by:
    creating a digital model of said fittings;
    importing a digital representation of the orientation and position of the mating surfaces of said anchors into a computer program;
    aligning said digital model of said fittings with said digital representation of the orientation and position of the mating surfaces of said anchors;
    creating bridging structures spanning between said fittings and
    combining said digital model of said bridging structures and said digital model of said fittings.

16. The method of claim 1, wherein said positioning said digital model of said dental framework and said digital representation of said soft tissue surface in relationship with one another is performed by:
    aligning said digital model of said framework with said digital representation of said soft tissue surface such that at least a portion of at least one of said bridging structures is extending through said digital representation of said soft tissue surface.

17. The method of claim 1, wherein at least a portion of said soft tissue confronting surface of at least one of said bridging structures is straight cut following a profile conforming to the contour of the confronting soft tissue beneath said at least one of said bridging structures during said step of removing any material.

18. The method of claim 17, wherein said profile follows a path complimentary to the soft tissue surface constrained in one direction by the facial side of said at least one of said bridging structures and constrained in another direction by the lingual side of said at least one of said bridging structures.

19. The method of claim 17, wherein said profile follows a path complimentary to said soft tissue surface beneath the facial surface edge of said soft tissue confronting surface of said at least one of said bridging structures.

20. The method of claim 17, wherein said profile follows a path complimentary to said soft tissue surface beneath the lingual surface edge of said soft tissue confronting surface of said at least one of said bridging structures.

21. The method of claim 17, wherein said profile follows a path complimentary to the contour of the soft tissue of said patient beneath the lateral midpoint of the surface of said at least one of said bridging structures confronting said soft tissue surface.

22. The method of claim 1, further comprising forming edges of said soft tissue confronting surface to be beveled.

23. The method of claim 1, further comprising forming edges of said soft tissue confronting surface to be rounded.

24. The method of claim 1, further comprising forming said soft tissue confronting surface to possess at least one cross-sectional profile selected from a group consisting of elliptical, rounded, multifaceted, chamfered and nonlinear freeform.

25. A method of creating a dental framework having a plurality of mating surfaces configured to engage a corresponding plurality of anchors in a patient's jaw bone, the method comprising the steps of:
    attaching a coping to each of said anchors;
    forming an impression of said patient's mouth in which said copings are embedded;
    attaching an analog to each of said copings;
    forming a stone cast from said impression in which said analogs are embedded;
    attaching a fitting to each of said analogs;
    connecting said fittings with a bridging structure of at least one material to form a wax-up framework, said wax-up framework representing a physical model of a finished framework;
    digitally scanning said wax-up framework coupled to said stone cast with said fittings attached to said analogs to generate a wax-up framework and stone cast point cloud dataset;
    digitally scanning said wax-up framework to generate a wax-up framework point cloud dataset;
    attaching alignment posts having surface extensions to each of said analogs embedded in said stone cast;

digitally scanning said surface extensions and said stone cast to generate an alignment post and stone cast point cloud dataset;

aligning said point cloud datasets using features common to said point cloud datasets;

creating a first digital surface model of said wax-up framework from said wax-up framework point cloud dataset; deriving the relative positions and orientations of said mating surfaces from said point cloud datasets; combining said first digital surface model of said wax-up framework and said mating surfaces to generate a second digital surface model of said framework;

creating a tool path based on said second digital surface model for manufacture of said framework; and manufacturing said framework in accordance with said toolpath.

26. The method of claim 25, wherein said at least one material used to form said wax-up framework is selected from a group consisting of wax, acrylic, and polymer material.

27. The method of claim 25, wherein said toolpath is a computer instruction and said dental framework is manufactured by computer controlled machinery in accordance with said instruction.

28. The method of claim 25, wherein at least one of the features common to said point cloud datasets is selected from a group consisting of window pane fixtures, alignment posts, and calibration fixtures.

29. The method of claim 25, wherein the features common to said point cloud datasets include datums created from said point cloud datasets.

30. A method of creating a dental framework having a plurality of anchor mating surfaces configured to engage mating surfaces of a corresponding plurality of anchors in a jaw bone of a patient from a stone cast of the patient's mouth and a wax-up framework, the stone cast having analogs embedded therein representing the exact positions and orientations of the anchor mating surfaces, the method comprising the steps of:

creating a digital representation of said patient's mouth including soft tissue contours associated with said jaw bone and further including the position and orientation of each said anchor mating surface in relation to each other and further in relation to said soft tissue contours;

said position and orientation obtained from said stone case of said patient;

creating a digital representation of the surface of said framework based upon said wax-up framework;

creating a digital representation of the surface of said wax-up framework coupled with said stone cast;

aligning said digital representations using features common to said digital representations;

aligning a digital parameterized fitting to said digital representation of the position and orientation of each anchor mating surface;

combining said digital parameterized fitting with said digital representation of said wax-up framework to form a final digital representation of said framework;

creating a tool path based on said final digital representation of said framework for manufacture of said framework; and manufacturing said framework in accordance with said toolpath.

31. The method of claim 30, wherein said wax-up framework is created from a material selected from a group consisting of wax, acrylic, and polymer material.

32. The method of claim 30, wherein said digital representation of said soft tissue contours and said anchor mating surfaces are created from said stone cast by a method comprising the steps of:

attaching alignment posts having surface extensions to each of said analogs and digitally scanning said surface extensions and said stone cast to create said digital representation in the form of a point cloud dataset.

33. The method of claim 30, wherein creation of said digital representation of said framework includes the steps of:

attaching a fitting to each of the plurality of analogs;

forming a wax-up framework in which said fittings are coupled together with a bridging structure to hold them in their relative positions;

removing said wax-up framework from said analogs; and digitally scanning said wax-up framework to create said digital representation in the form of a point cloud dataset.

34. The method of claim 30, wherein said digital representation of said framework is created by digitally scanning said wax-up framework to create said digital representation in the form of a point cloud dataset.

35. The method of claim 30, wherein the creation of said digital representation of the surface of said framework coupled with said stone cast includes the steps of:

coupling said wax-up framework with said stone cast and digitally scanning said framework coupled to said stone cast to create said digital representation in the form of a point cloud dataset.

* * * * *